(12) United States Patent
Vorobiev et al.

(10) Patent No.: US 9,056,887 B2
(45) Date of Patent: Jun. 16, 2015

(54) MINOR GROOVE BINDER PHOSPHORAMIDITES AND METHODS OF USE

(75) Inventors: Alexei Vorobiev, Redmond, WA (US); Eugeny A. Lukhtanov, Bothell, WA (US)

(73) Assignee: Elitech Holding B.V., Spankeren (NL)

( * ) Notice: Subject to any disclaimer, the term of this patent is extended or adjusted under 35 U.S.C. 154(b) by 323 days.

(21) Appl. No.: 13/556,513

(22) Filed: Jul. 24, 2012

(65) Prior Publication Data
US 2013/0030166 A1 Jan. 31, 2013

Related U.S. Application Data

(60) Provisional application No. 61/511,733, filed on Jul. 26, 2011.

(51) Int. Cl.
| | |
|---|---|
| *C07H 21/00* | (2006.01) |
| *C07F 9/02* | (2006.01) |
| *C07D 403/00* | (2006.01) |
| *C07F 9/547* | (2006.01) |
| *C07F 9/6506* | (2006.01) |
| *C07F 9/6558* | (2006.01) |
| *C07F 9/6561* | (2006.01) |
| *C07D 235/18* | (2006.01) |
| *C07D 403/04* | (2006.01) |
| *C07D 519/00* | (2006.01) |

(52) U.S. Cl.
CPC ............ *C07H 21/00* (2013.01); *C07F 9/65068* (2013.01); *C07F 9/65583* (2013.01); *C07F 9/6561* (2013.01); *C07D 235/18* (2013.01); *C07D 403/04* (2013.01); *C07D 519/00* (2013.01)

(58) Field of Classification Search
CPC ........... C07F 90/65068; C07F 9/65583; C07F 9/6561; C07F 9/65068; C07D 519/00; C07D 403/04; C07D 435/18; C07H 21/00
See application file for complete search history.

(56) References Cited

U.S. PATENT DOCUMENTS

| | | | |
|---|---|---|---|
| 4,835,263 A | 5/1989 | Nguyen et al. | |
| 5,419,966 A | 5/1995 | Reed et al. | |
| 5,512,677 A | 4/1996 | Chern et al. | |
| 5,585,481 A | 12/1996 | Arnold, Jr. et al. | |
| 5,696,251 A | 12/1997 | Arnold, Jr. et al. | |
| 5,736,626 A | 4/1998 | Mullah et al. | |
| 5,801,155 A | 9/1998 | Kutyavin et al. | |
| 5,942,610 A | 8/1999 | Nelson et al. | |
| 5,955,590 A | 9/1999 | Levina et al. | |
| 6,084,102 A * | 7/2000 | Kutyavin et al. | 548/100 |
| 6,312,894 B1* | 11/2001 | Hedgpeth et al. | 435/6.11 |
| 6,312,984 B1 | 11/2001 | Dennison | |
| 6,426,408 B1* | 7/2002 | Kutyavin et al. | 536/22.1 |
| 6,486,308 B2* | 11/2002 | Kutyavin et al. | 536/23.1 |
| 6,492,346 B1* | 12/2002 | Hedgpeth et al. | 514/44 R |
| 6,884,584 B2* | 4/2005 | Hedgpeth et al. | 435/6.1 |
| 6,949,367 B1 | 9/2005 | Dempcy et al. | |
| 7,045,610 B2 | 5/2006 | Dempcy et al. | |
| 7,205,105 B2* | 4/2007 | Afonina et al. | 435/6.1 |
| 7,381,818 B2 | 6/2008 | Lokhov et al. | |
| 7,485,442 B2* | 2/2009 | Afonina et al. | 435/91.1 |
| 7,556,923 B1* | 7/2009 | Hedgpeth et al. | 435/6.11 |
| 7,582,739 B2 | 9/2009 | Lukhtanov et al. | |
| 7,794,945 B2* | 9/2010 | Hedgpeth et al. | 435/6.11 |
| 7,799,926 B2 | 9/2010 | Gall | |
| 7,851,606 B2* | 12/2010 | Lukhtanov et al. | 536/23.1 |
| 8,465,921 B2* | 6/2013 | Hedgpeth et al. | 435/6.1 |
| 2006/0166223 A1 | 7/2006 | Reed et al. | |
| 2011/0172289 A1 | 7/2011 | Khvorova et al. | |

FOREIGN PATENT DOCUMENTS

| | | |
|---|---|---|
| WO | 2005/082894 | 9/2005 |
| WO | 2007/016455 | 2/2007 |

OTHER PUBLICATIONS

Beaucage, S.L, et al; Advances in the Synthesis of Oligonucleotides by the Phosphoramidite Approach; Tetrahedron, vol. 48, No. 12, 2223-2311, 1992.
Reddy, B.S. Praveen, et al; Synthetic DNA Minor Groove-Binding Drugs; Pharmacology & Therapeutics 84, 1-111, 1999.
Walker, W.L., et al; Progress in the Design of DNA Sequence-Specific Lexitropsins; Biopolymers, 44, 323-334, 1997.
Wemmer, D.E., et al; Targeting the Minor Groove of DNA, Current Opinion in Structural Biology, 7, 355-361, 1997.
Zimmer, Christopher ,et al; Nonintercalating DNA-Binding Ligands: Specificity of the Interaction and Their Use As Tools in Biophysical, Biochemical and Biological Investigations of the Genetic Material; Prog. Biophys. Molec. Bio. 47, 31-112, 1986.

(Continued)

*Primary Examiner* — Lawrence E Crane
(74) *Attorney, Agent, or Firm* — Jackson Walker L.L.P.

(57) ABSTRACT

Minor groove binder phosphoramidites having the formula M-L-PA, wherein M is a minor groove binder comprising a protected heteroaromatic amine, L is a linker, and PA is a phosphoramidite group, have been synthesized. Preferred methods of synthesis include synthesizing a minor groove binder intermediate containing a transiently protected hydroxyl group, protecting heteroaromatic amines of the corresponding minor groove binder intermediate as carbamate intermediates, reacting the carbamate intermediate to remove the transient protecting group to yield carbamate-protected minor groove binder agent as an intermediate with a free hydroxyl group, and converting the intermediate with a free hydroxyl group to the desired minor groove binder phosphoramidite. These minor groove binder phosphoramidites are useful in the preparation of oligonucleotide conjugates, particularly those for use as probes and primers. In preferred methods, an oligonucleotide sequence is synthesized using nucleoside phosphoramidites and the minor groove binder phosphoramidite is incorporated into the oligonucleotide sequence to form a protected oligonucleotide-minor groove binder conjugate. Then, deprotection produces the oligonucleotide-minor groove binder.

7 Claims, 5 Drawing Sheets

(56) References Cited

OTHER PUBLICATIONS

Afonina et al., Primers With 5' Flaps Improve Real-Time PCR; Biotechniques, 43: 770, 772, 774; (Dec. 2007).
Afonina et al., Sequence-Specific Arrest of Primer Extension on Single-Stranded DNA by an Oligonucleotide-Minor Groove Binder Conjugate; PNAS, 93: 3199-3204 (Apr. 1996).
Amishiro et al., New Water Soluble Duocarmycin Derivatives: Synthesis and Antitumor Activity of A-Ring Pyrrole Compounds Bearing B-Heteroarylacryloyl Groups; J. Med. Chem., 42: 669-676 (1999).
Basel, Yochai and Alfred Hassner, Di-Tert-Butyl Dicarbonate and 4-(Dimethylamino)Pyridine Revisited. Their Reactions With Amines and Alcohols; J. Org. Chem., 65 (20), 6368-6380 (2000).
Boger et al., Parallel Synthesis and Evaluation of 132(+)-1, 2,9,9a-Tetrahydrocyclopropa[c] Benz[e]Indol-4-One (CBI) Analogues of CC-1065 and the Duocarmycins Defining the Contribution of the DNA-Binding Domain; J. Org. Chem., 66: 6654-6661 (2001).
Boger et al, CC-1065 and the Duocarmycins: Synthetic Studies; Chem. Rev., 97, 787-828 (1997).
Boger et al., CBI-TMI: Synthesis and Evaluation of a Key Analog of the Duocarmycins; JACS,116: 7996-8006 (1994).
Boger et al., CC-1065 Partial Structures: Enhancement of Noncovalent Affinity for DNA Minor Groove Binding Through Introduction of Stabilizing Electrostatic Interactions; J. Org. Chem., 57:1277-1284 (1992).
Boger et al., Studies on the Total Synthesis of CC-1065 ETC.; J. Org. Chem., 52: 1521-1530 (1987).
Bostock-Smith & Searle, DNA Minor Groove Recognition by Bis-Benzimidazole Analogues of Hoechst 33258; Nucl. Acids. Res., 27(7): 1619-1624 (1999).
Greene, T. W. and P. G. Wuts, Protective Groups in Organic Chemistry, (Wiley, 2nd ed. 1991).
Howard et al., Novel Furano Analogues of Duocarmycin C1 and C2 etc.; Bioorg. & Medicin. Chem., 10: 2941-2952 (2002).
Levina et al., Conjugates of Minor Groove DNA Binders With Oligodeoxynucleotides: Synthesis and Properties; Antisense & Nucleic Acid Drug Dev., 6: 75-85 (1996).
MacMillan et al., An Additional Spirocyclization for Duocarmycin SA; JACS,130: 16521-16523 (2008).
O'Donnell et al., Synthesis and Properties of a Hoechst-Like Minor-Groove Binding Agent Tethered to an Oligodeoxynucleotide; Bioorg. & Med. Chem., 6: 743-750 (1995).
Rajur et al., Hoechst 33258 Tethered by a Hexa(Ethylene Glycol) Linker to the 5'-Termini of Oligodeoxynucleotide 15-Mers Etc.; J. Org. Chem., 62: 523-529 (1997).
Robles et al., A Parallel-Stranded DNA Triple Tethering a Hoechst 33258 Analogue Results in Complex Stabilization etc; J. Am. Chem. Soc.,118: 5820-5821 (1996).
Hodgson; The Sandmeyer Reaction; Ber.17, 1633, 2650 (1884), Chem. Rev., 40: 251-277 (1947).
Smith et al., The Structural Basis for in Situ Activation of DNA Alkylation by Duocarmycin SA, J. Mol. Biol., 300: 1195-1204 (2000); Abstract only.
Tanada et al, Design of New Bidentate Ligands Constructed of Two Hoechst 33258 Units for Discrimination of the Length of Two A3T3 Binding Motifs; J. Org. Chem., 71: 125-134 (2006).
Tichenor et al., Systematic Exploration of the Structural Features of Yatakemycin Impacting DNA Alkylation and Biological Activity; JACS, 129(35), 10858-10869 (2007).
Tichenor et al, Rational Design, Synthesis, and Evaluation of Key Analogues of CC-1065 and the Duocarmycins; JACS, 129: 14092-14099 (2007).
Tichenor et al., Asymmetric Total Synthesis of (+)- and Ent(−)-Yatakemycin and Duocarmycin SA etc., JACS, 128: 15683-15696 (2006).
Wiederholt et al., Oligonucleotides Tethering Hoeschst 33258 Derivatives: Effect of the Conjugation Site on Duplex Stabilization and Fluorescence Properties; Bioconjug. Chem., 8: 119-126 (1997).
Wiederholt et al, DNA-Tethered Hoechst Groove-Binding Agents: Duplex Stabilization and Fluorescence Characteristics; J. Am. Chem. Soc., 118: 7055-7062 (1996).
Xu et al., Ethyl Trifluoroacetate: A Power Reagent for Differentiating Amino Groups; Tetrahedron Lett., 36(41), 7357-7360 (1995).
Yamada et al., Total Synthesis of the Duocarmycins; JACS, 125: 6630-6631 (2003).
Ichumura et al., Duocarmycin SA, A New Antitumor Antibiotic From *Streptomyces* SP., The J. of Antibiot., 43: 1037-1038 (1990).
The International Bureau of WIPO, International Preliminary Report on Patentability; PCT Application No. PCT/US2012/047943; Feb. 6, 2014.
European Patent Office, International Search Report and Written Opinion; PCT Application No. PCT/US2012/047943; Nov. 14, 2012.
Chenna, A., et al; Large Scale Synthesis of P-Benzoquinone-2'-Deoxyadenosine Adducts and Their Site-Specific Incorporation Into DNA Oligonucleotides; Chem. Res. Toxicol., vol. 8, No. 6, 865-874, Jan. 1, 1995.
Christov, P.P., et al; the C8-2'-Deoxyguanosine Adduct of 2-Amino-3-Methylimidazo[1,2-d]Naphthalene, a Carbocyclic Analogue of the Potent Mutagen 2-Amino-3-Methylimidazo[4,5-f]Quinoline, is a Block to Replication In Vitro; Chem. Res. Toxicol., vol. 23, No. 6, 1076-1088, Jun. 21, 2010.
Elmquist, C.E., et al; Site-Specific Synthesis and Properties of Oligonucleotides Containing C8-Deoxyguanosine Adducts of the Dietary Mutagen 10; Journal of the American Chemical Society; vol. 126, No. 36, 11189-11201, Sep. 1, 2004.
Guianvarc'h, D., et al; Synthesis, Incorporation Into Triplex-Forming Oligonucleotide, and Binding Properties of a Novel 2'-Deoxy-C-Nucleoside Featuring a 6-(Thiazolyl-5) Benzimidazole Nucleobase; Organic Letters, vol. 4, No. 24, 4209-4212, Nov. 1, 2002.
Inohara, H., et al; 2', 4'-BNA Derivatives Bearing an Unnatural Nucleobase: Synthesis and Application to Triplex-Forming Oligonucleotides; Nucleic Acids Symposium Series, No. 48, 63-64, 2004.
Stover, J.S., et al; Synthesis of Oligonucleotides Containing the N2-Deoxyguanosine Adduct of the Dietary Carcinogen 2-Amino-3-Methylimidazo[4,5-f]Quinoline; Chem. Res. Toxicol., vol. 20, No. 12, 1972-1979, Dec. 1, 2007.
Wamberg, et al; Intercalating Nucleic Acids (INAS) Containing Insertions of 6H-Indolo[2,3-b]Quinoxaline, Tetrahedron, vol. 62, No. 48, 11187-11199, Nov. 27, 2006.

\* cited by examiner

MINOR GROOVE BINDER PHOSPHORAMIDITES AND METHODS OF USE

This application claims priority to U.S. Provisional Patent Application Ser. No. 61/511,733, filed Jul. 26, 2011, entitled "Minor Groove Binder Phosphoramidites and Methods of Use," the entire contents of which are hereby incorporated by reference.

BACKGROUND

This disclosure relates to minor groove binder ("MGB") phosphoramidites, their synthesis, and their use in the synthesis of oligonucleotide conjugates. The phosphoramidites are useful, for example, for the automated synthesis of oligonucleotide conjugates on solid supports.

Oligonucleotide conjugates have been developed and applied widely in molecular biology in hybridization-based procedures as primers, probes, antagomers and the like. Use of these reagents in molecular biology procedures often requires modification to improve resistance to nuclease susceptibility, improve duplex stabilization of conjugate target duplexes, and allow detection or improve conjugate solubility. This then led to the inclusion of one or more non-isotopic labels such as fluorescent dyes, quenchers, intercalators, biotin, bead particles, enzymes, antibodies, antigens, hydrophobic compounds such as cholesterol, ionic compounds such as spermine, and the like. Additional modifications have been introduced in the oligonucleotide to the backbone to increase stability or nuclease resistance. These modifications include the introduction of locked nucleic acids, 2'-O-alkyl ribose units, methyl phosphonate- or phosphorothioate-, or phosphorodithoate-linkages and peptide nucleic acids. The naturally occurring bases in nucleic acids are routinely substituted with modified bases to tailor the properties of the oligonucleotide conjugate (U.S. Pat. No. 6,949,367). Minor groove binders (U.S. Pat. No. 5,801,155) and intercalators (U.S. Pat. No. 4,835,263) have been used to stabilize duplex formation. With widespread application of these compounds in diagnostics and therapeutics, there exists a need to improve reagents to satisfy the increasing demand for covalently attached minor groove binder oligonucleotide conjugates.

Minor groove binders can be attached to oligonucleotides using post synthesis conjugation (U.S. Pat. No. 5,955,590) or MGB-modified DNA synthesis solid supports (U.S. Pat. No. 5,801,155). Reagents and methods to synthesize minor groove binder conjugates are also described in U.S. Pat. No. 6,084,102. One example is a tetrafluorophenyl ester of the tripeptide 3-carbornyl-1,2-dihydro-3H-pyrrolo[3,2,-e]indole-7-carboxylic acid residues (TFP-DPI₃ carboxylate), which is an analog of the naturally occurring antibiotic CC-1065. TFP-DPI₃ carboxy late can be used to synthesize a solid support for automated manufacturing of MGB-oligonucleotide conjugates. Alternatively, TFP-DPI₃ can be used post synthetically to attach the MGB ligand.

Other minor groove binder oligonucleotide conjugates have been reported. Hoechst 33258 analogs with a bromoacetamide tether were coupled to oligonucleotides bearing alkyl thiol functionality (Wiederbolt et al., J. Am. Chem. Soc., 7055-7062 (1997). The same method was used to conjugate a DAPI analog to an oligonucleotide (O'Donnell et al., 1995). Hoechst 33258 can be tethered by a hexa(ethylene glycol) linker to a solid support through a cleavable linker. This solid support can then be used to synthesize the Hoechst 33258 oligonucleotide conjugate (Rajur et al., *The Journal of Organic Chemistry* 62: 523-529 (1997). Rajur and co-workers attempted to synthesize a Hoechst 33258-hexa(ethylene glycol) phosphoramidite but reported no success, suggesting that the benzimidazole groups of the minor groove binder competed with hydroxyl group for the phosphitylating reagent or, perhaps, were involved in other side reactions.

For some minor groove binders, phosphoramidite preparation may present challenges not only due to the presence of unwanted reactions, but also because of their very low solubility in oligonucleotide synthesis solvents such as acetonitrile. Solubility, for example, is a very pronounced problem (Boger et al., J. Org. Chem., 1521-1530 (1987)) for dihydropyrroloindole ("DPI")-containing MGB agents belonging to the CC-1065 and duocarmycin family.

A need exists for minor groove binder phosphoramidites in the synthesis of oligonucleotide conjugates that will eliminate laborious post-synthesis attachment and, therefore, facilitate automation and scale-up. In order to achieve this goal, a need exists for an MGB protecting strategy that would be compatible with automated oligonucleotide synthesis, eliminate side reactions related to the presence of heteroaromatic amines and improve solubility in suitable organic solvents.

SUMMARY

The present disclosure pertains to minor groove binder phosphoramidites, including their structure, methods of synthesis, and their use in oligonucleotide conjugates.

Generally, the minor groove binder phosphoramidites disclosed herein are compounds of the following formula:

$$M\text{-}L\text{-}PA \qquad \text{Formula I}$$

wherein M is a minor groove binder ("MGB") comprising a protected heteroaromatic amine, L is a linker; and PA is a phosphoramidite group. L may be acyclic, cyclic, aromatic or a combination thereof, and may have from 4 to 50 atoms, exclusive of hydrogen atoms that fill available valences, selected from a group consisting of C, N, O, P, and S. The M portion of the phosphoramidites described herein is optionally substituted to introduce additional functionalities or modulate the MGB's properties. The introduction of additional functionalities is demonstrated in Table 1 to 3 and further discussed below. Additional examples of modulation of the MGB's properties are disclosed in U.S. Pat. No. 7,582,739.

In a preferred embodiment the heteroaromatic amine protection is essentially stable during oligonucleotide assembly and removed during oligonucleotide deprotection. In another preferred embodiment the heteroaromatic amine protecting group is a carbamate group. In another preferred embodiment the heteroaromatic group is an indole or benzimidazole ring. In yet another preferred embodiment the minor groove binder is selected from the group including analogs of CC-1065, duocarmycin and Hoechst 33258.

More specifically, the minor groove binder phosphoramidites may include compounds of the following formulas II and III:

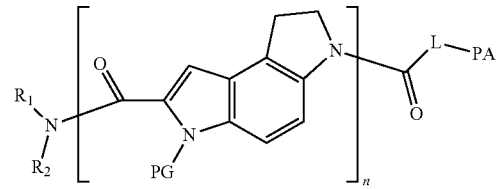

Formula II

Formula III

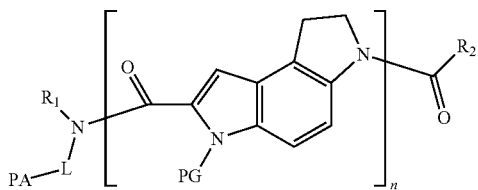

wherein $R^1$ and $R^2$ are each independently PG, L, $C_{1-8}$ alkyl, $C_{1-8}$ heteroalkyl, protected $C_{1-8}$ heteroalkyl, —(CH$_2$CH$_2$O)$_n$CH$_2$CH$_3$ where n=1 to 8, or $R^1$ and $R^2$ form a 5 or 6 member ring structure which may contain 0, 1 or 2 hetero atoms selected from O, S and N; n=1 to 4; L is a linker which is acyclic, cyclic, aromatic or a combination thereof, having from 4 to 50 atoms, exclusive of hydrogens that fill available valences, selected from a group consisting of C, N, O, P, and S; PG is a protecting group; and PA is a phosphoramidite group.

The minor groove binder phosphoramidites may also include compounds of the following formulas IV and V:

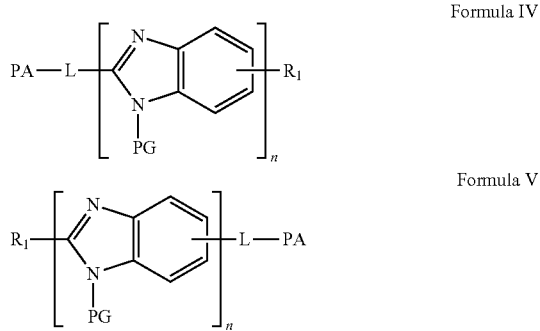

Formula IV

Formula V wherein $R_1$ is L, $C_{1-8}$ alkyl, $C_{1-8}$ heteroalkyl, protected $C_{1-8}$ heteroalkyl, —(CH$_2$CH$_2$O)$_n$CH$_2$CH$_3$ where n=1 to 8, substituted or unsubstituted aryl and heteroaryl; n=1 to 4; L is a linker which is acyclic, cyclic, aromatic or a combination thereof, having from 4 to 50 atoms, exclusive of hydrogens that fill available valences, selected from a group consisting of C, N, O, P, and S; PG is a protecting group; and PA is a phosphoramidite group.

Preferred methods for the synthesis of the current minor groove binder phosphoramidites include a method comprising the steps of:

synthesizing a minor groove binder intermediate containing a transiently protected hydroxyl group;

protecting heteroaromatic amines of said corresponding minor groove binder intermediate as carbamate intermediates;

reacting said carbamate intermediate to remove the transient protecting group to yield carbamate-protected minor groove binder agent as an intermediate with a free hydroxyl group, and converting said intermediate with a free hydroxyl group to the desired minor groove binder phosphoramidite.

In some embodiments, the minor groove binder intermediate is an intermediate assembled from monomeric building units. In the case of CC 1065 analogs the starting monomeric units, which are based on 1,2-dihydro-3H-pyrrolo[3,2-e]indole-7-carboxylic acid, (DPI carboxylic acid) can be made according to procedures described in the chemical literature (Boger, D., Coleman, R and Invergo. B., J. Org. Chem., 52: 1521-1530 (1987)). The assembly of the DPI units into minor groove binders (DPI trimer), which is used in this disclosure, is described in U.S. Pat. No. 5,801,155. Methods for the synthesis of Hoechst 33258 analogs from monomeric subunits requires the systematic assembly of the different subunits as described in Wiederholt, K., Rajur, S., Giuliana, J., O'Donnell, M., and BcLaughlin, L., J. Am. Chem. Soc., 118: 7055-7062 (1996). The synthesis of Duocarmycin analogs from different monomeric units is also known in the art (Tichenor et al., 2006; Tichenor et al. 2007). The preferred protecting groups for the heteroaromatic amines of the minor groove binder phosphoramidites of this invention are stable during the automated oligonucleotide assembly steps and can be removed during the final deprotection. In further embodiments, the desired protected minor groove binder phosphoramidites obtained are used in the synthesis of oligonucleotide-minor groove binder conjugates.

DETAILED DESCRIPTION

I. Definitions

Figure 1:
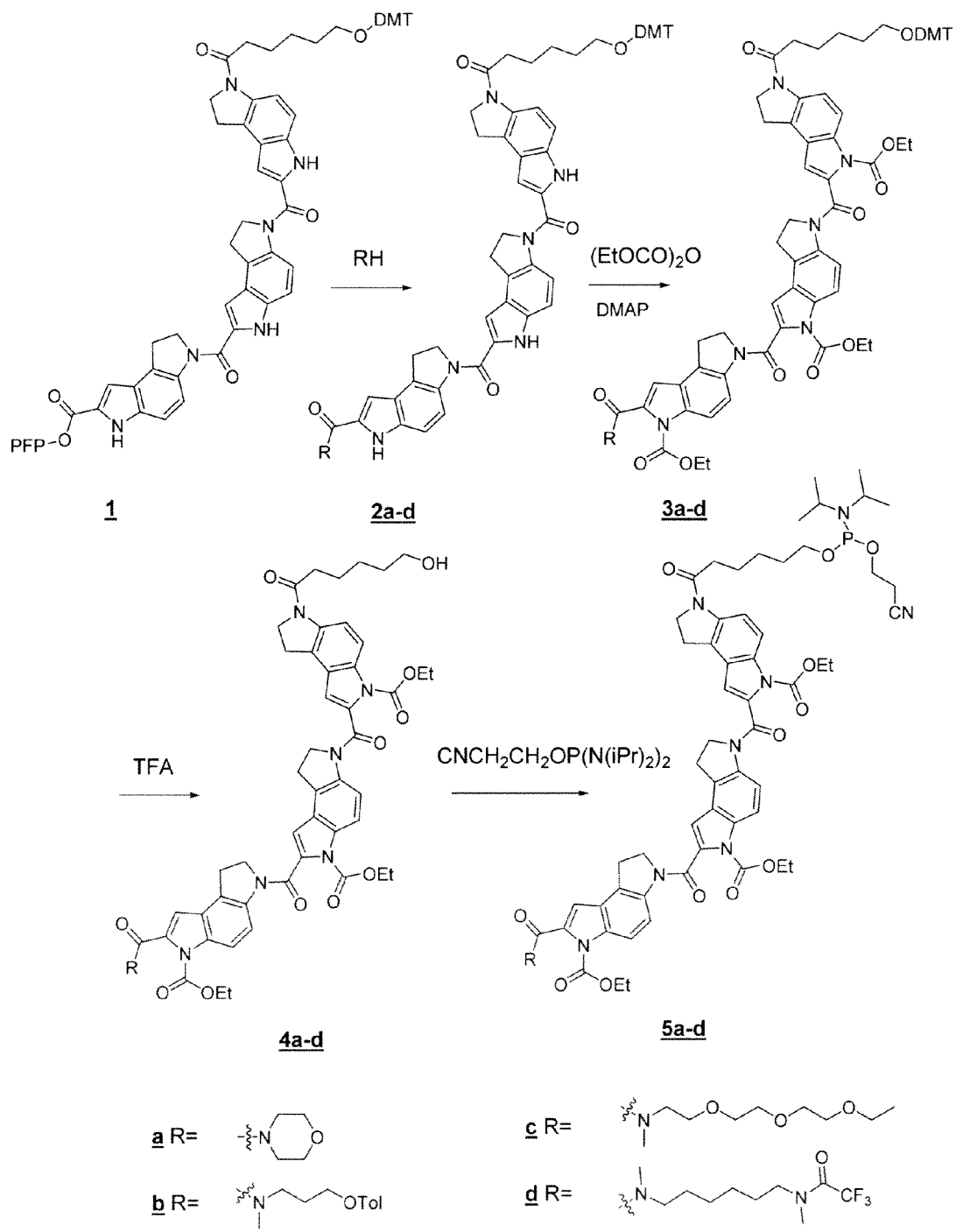
FIG. 1 shows a reaction scheme for the synthesis of DPI$_3$ type minor groove binder phosphoramidites.

The term "minor groove binder" refers to a compound binding to a nucleic acid in a non-intercalating mode (U.S. Pat. No. 5,901,155). For the purpose of this disclosure, "minor groove binders" comprise a heteroaromatic amine. Preferred minor groove binders are analogs of CC-1065, duocarmycin and Hoechst 33258.

The term "heteroaromatic amines" refers to aromatic heterocycles containing at least one —NH— group in the ring. Examples of "heteroaromatic amines" are pyrrole, indole, imidazole, benzimidazole, triazole, benzotriazole, purine, and the like.

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, (C$_1$-C$_8$)alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, arylalkyloxy), when a prefix is not included to indicate the number of main chain carbon atoms in an alkyl portion, the radical or portion thereof will have eight or fewer main chain carbon atoms.

The term "heteroalkyl" refers to an alkyl radical as defined herein with one, two or three substituents independently selected from cyano, —OR$^a$, —NR$^b$R$^c$, and —S(O)$_n$R$^d$ (where n is an integer from 0 to 2), with the understanding that the point of attachment of the heteroalkyl radical is through a carbon atom of the heteroalkyl radical. $R^a$ is hydrogen, alkyl, aryl, arylalkyl, alkoxycarbonyl, aryloxycarbonyl carboxamido, or mono- or di-alkylcarbamoyl. $R^b$ is hydrogen, alkyl, aryl or arylalkyl. $R^c$ is hydrogen, alkyl, aryl, arylalkyl, alkoxycarbonyl, aryloxycarbonyl, carboxamido, mono- or di-alkylcarbamoyl or alkylsulfonyl. $R^d$ is hydrogen (provided that n is 0), alkyl, aryl, arylalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^a$, $R^b$, $R^c$, and $R^d$ can be further substituted by $NH_2$, fluorine, alkylamino, di-alkylamino, OH or alkoxy. Additionally, the prefix indicating the number of carbon atoms (e.g. $C_1$-$C_{10}$) refers to the total number of carbon atoms in the portion of the heteroalkyl group exclusive of the cyano, —$OR^a$, —$NR^bR^c$, and —$S(O)_nR^d$ portions.

"Protecting group" refers to a moiety, except alkyl or cycloalkyl group, that when attached to a reactive group in a molecule masks, reduces or prevents that reactivity. A "protected" molecule has one or more reactive groups protected by protecting groups. Examples of protecting groups can be found in T. W. Greene and P. G. M. Wuts, Protective Groups in Organic Synthesis, 3$^{rd}$ edition, John Wiley & Sons, New York, 1999, Harrison and Harrison et al. Compendium of Synthetic Organic Methods, Vols. 1-8 (John Wiley and Sons, 1971-1996), and "Protection of Nucleosides for Oligonucleotide Synthesis," Current Protocols in Nucleic Acid Chemistry, ed. by Boyle, A. L., John Wiley & Sons, Inc., 2000, New York, N.Y., all of which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

The term "linker" refers to a moiety that is used to assemble various portions of the molecule or to covalently attach the molecule (or portions thereof) to a solid support. Typically a linker or linking group has functional groups that are used to interact with and form covalent bonds with functional groups in the ligands or components (e.g., fluorophores, oligonucleotides, minor groove binders, or quenchers) of the conjugates described and used herein. Examples of functional groups on the linking groups (prior to interaction with other components) include —$NH_2$, —$NHNH_2$, —$ONH_2$, NHC=(O) $NHNH_2$, —OH, —COOH or —SH. The linking groups are also those portions of the molecule that connect other groups (e.g. phosphoramidite moieties and the like) to the conjugate. Additionally, a linker can include linear or acyclic portions, cyclic portions, aromatic rings or combinations thereof. A linking group can be a bifunctional linker, trifunctional linker or polyfunctional linker, for example, di- and tri-functional linkers described in detail in the literature, as well as a 3'-alkylamine linker (U.S. Pat. No. 5,419,966) or a prolinol-based linker (U.S. Pat. No. 5,512,667). Tri- and tetrafunctional linkers have also been described (U.S. Pat. Nos. 5,451,463, 5,942, 610 and 5,696,251). Photocleavable linking groups for use in solid phase synthesis have been described (U.S. Pat. No. 5,739,386). Trifunctional linkers are also available commercially (Glen Research, Sterling, Va.). Additionally, the linking group can be acyclic, cyclic, aromatic or a combination thereof, having from 4 to 50 atoms selected from the group consisting of C, N, O, P and S and exclusive of hydrogen atoms that fill available valences, and further having a nitrogen atom directly connected to the adjacent carbonyl group.

The term "phosphoramidite" refers to a trivalent phosphorus group typically used in oligonucleotide synthesis. Detailed descriptions of the chemistry used to form oligonucleotides by the phosphoramidite method are provided in Caruthers et al., U.S. Pat. Nos. 4,458,066 and 4,415,732; Caruthers et al., Genetic Engineering, 4:1-17 (1982); Users Manual Model 392 and 394 Polynucleotide Synthesizers, pages 6-1 through 6-22, Applied Biosystems, Part No. 901237 (1991), each of which are incorporated by reference in their entirety.

The term "conjugate" refers to a molecule formed by the covalent attachment of two or more components such as oligonucleotides, fluorophores, quenchers, minor groove binders, and the like.

"Oligonucleotide" and "polynucleotide" are used interchangeably and refer to a polymer of nucleotides, either natural or synthetic, including but not limited to those nucleotides having modified bases, sugar analogs, and the like. In certain cases, the oligonucleotide may include a 2'-OMe-ribonucleic acid unit or a locked nucleic acid ("LNA") unit, alone or in combination with each other or other components. Modified bases and locked nucleic acids are further discussed in U.S. Pat. No. 7,045,610, which is incorporated by reference. An oligonucleotide conjugate can refer to an oligonucleotide as defined, having at least one covalently attached fluorophore, quencher, minor groove binder ("MGB") or other useful fragments, as well as combinations of the recited components.

II. Synthesis

Activated pentafluorophenyl ester 1 of the $DPI_3$ type of minor groove bindinding ligands was prepared as previously described (U.S. Pat. No. 7,381,818) and coupled with four secondary amine-containing terminal functions generatin trimers 2(a-d), (Reaction Scheme 1, FIG. 1) suitable for following protection and phosphoramidite preparation. The use of secondary amino function prevents the possibility of the formation of acyclic side-product (Basel and Hassner 2000) during the following protection step. The trimers 2(a-d) were reacted with diethyl pyrocarbonate in the presence of DMAP to protect the three heteroaromatic indolamino groups and afford carbomates 3(a-d). Methyl and tert-butyl dicarbonates were also tested and produced the respective carbamates with good yields. However, the methylcarbamate-protected phosphoramidites were only sparingly soluble in acetonitrile, standard solvent for on-line oligosynthesis; whereas, the BOC-carbamate protection could not be completely removed during the standard deprotection step (conc. $NH_4OH$, +70° C., 2 h). Therefore, the ethylcarbamate protection was concluded to be optimal allowing fast deprotection and providing the required solubility in acetonitrile. Removal of the dimethoxytrityl protection group gave primary alcohols 4(a-d) which were then converted to final phosphoramidites 5(a-d) by phosphitylation with 2-cyanoethyl tetraisopropylphosphordiamidite.

In one embodiment, 1 can be substituted either on the phenyl ring or on the 5 member rings or alternatively on both (Boger et al, 1997; Boger et al., 1992; U.S. Pat. No. 7,799, 926, all incorporated by reference). These substitutions include one or more OH, $OR^1$ where $R^1$ is alkyl, —$OC(O)R^2$ where $R^2$ is alkyl or phenyl, —$NH_2$, $N(CH_3)_3$, $NO_2$, alkyl and $AsO_3H_2$ groups. The introduction of other substituents into phenyl, pyrrolidine or pyrrole rings is also possible, which would be understood to those skilled in the art. Phosphonate and sulfonate groups have been introduced into phenyl rings containing dyes (U.S. Pat. No. 7,671,218 and U.S. Pat. No. 6,130,101, both incorporated by reference). Halogen- and cyano-groups can also be introduced via an amino group with the Sandmeyer reaction (Sandmeyer, 1947, incorporated by reference).

The attachment point of the phosphoramidite could be in an alternate position of $DPI_3$ molecule, for example, as represented by Formula VI below:

Formula VI

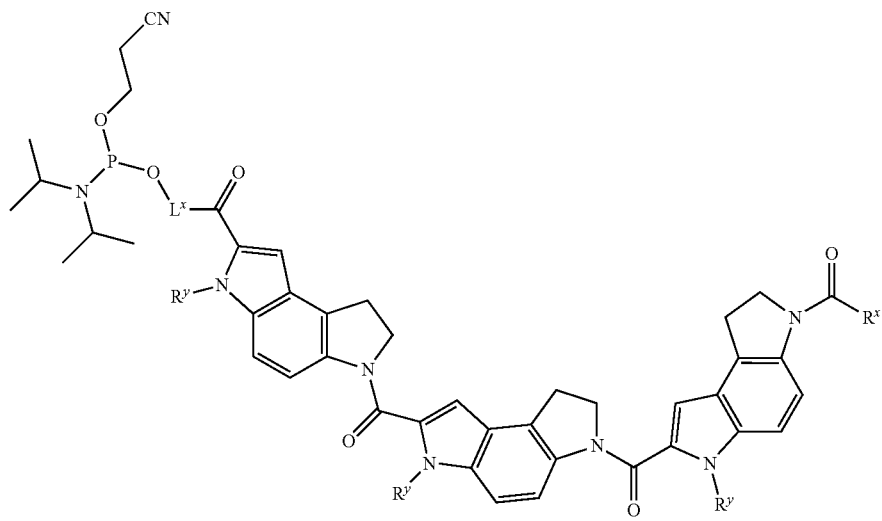

In Formula $V^1$, $L^x$ is a linker which is acyclic, cyclic, aromatic or a combination thereof, having from 4 to 50 atoms, exclusive of hydrogens that fill available valences, selected from group consisting of C, N, O, P, and S. $R^y$ is a protecting group with compatible solubility for oligonucleotide synthesis and is de-protected efficiently and $R^x$ is $C_{1-8}$ alkyl, $C_{1-8}$ heteroalkyl, protected $C_{1-8}$ heteroalkyl, or —$(CH_2CH_2O)_n$ $CH_2CH_3$ where n=1 to 8.

Figure 2:
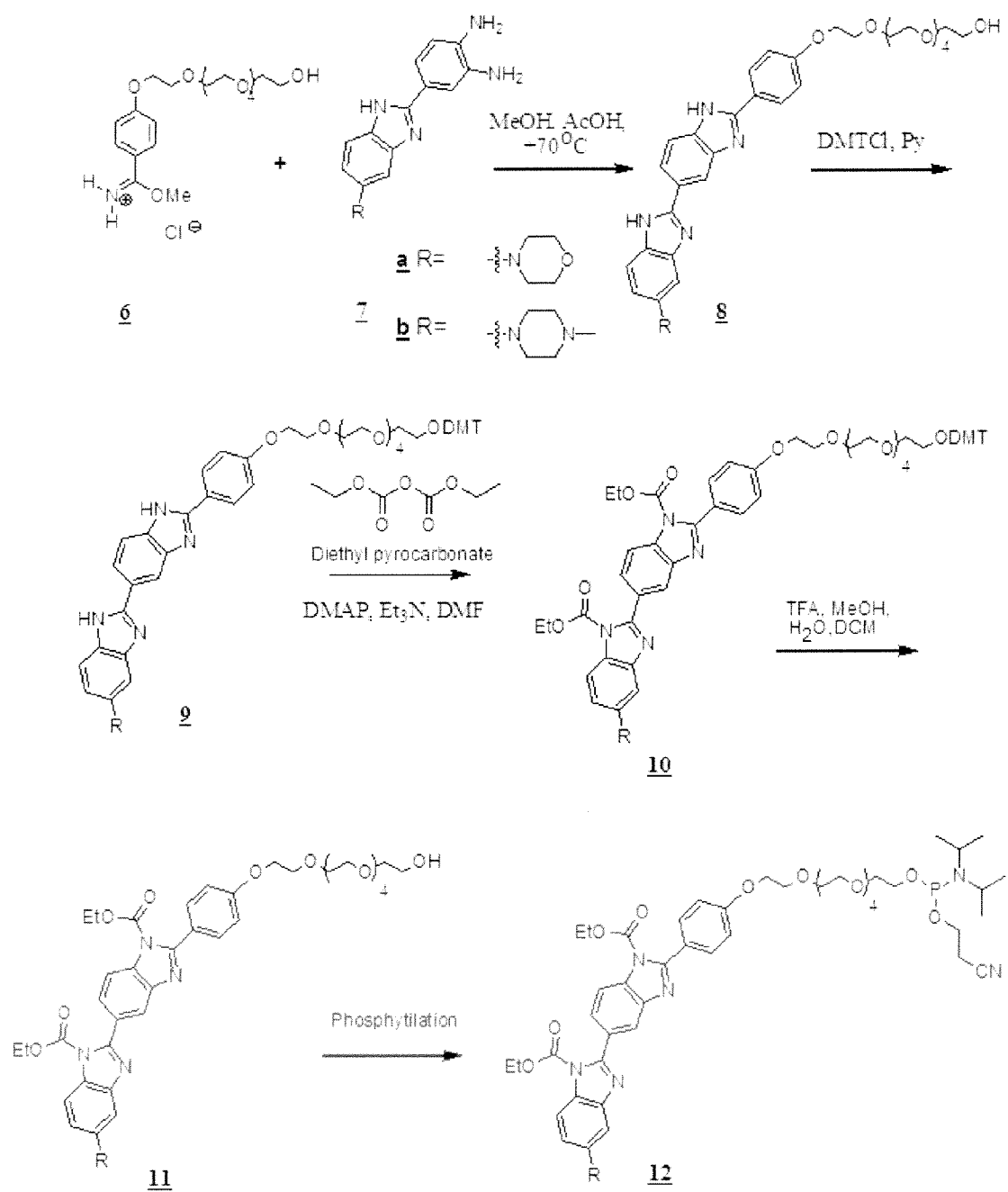
FIG. 2 shows a reaction scheme for the synthesis of di-benzimidazole type minor groove binder phosphoramidites.

A synthetic scheme for the preparation of di-benzimidazole-based minor groove binder phosphoramidites is shown in FIG. 2. Compound 8b was prepared as previously described starting from intermediates 6 and 7b (Hoechst 33258 Tethered by a Hexa(ethylene glycol) Linker to the 5'-Termini of Oligodeoxynucleotide 15-Mers: Duplex Stabilization and Fluorescence Properties. Sharanabasava B. Rajur, Jordi Robles, Kristin Wiederholt, Robert G. Kuimelis, and Larry W. McLaughlin. J. Org. Chem., 1997, 62 (3), pp 523-529). Similarly, compound 8a was synthesized from compound 7a (PCT Int. Appl. (2011). WO 2011123890 A1. Preparation of benzimidazole derivatives as radioprotector compounds. By Martin, Roger Francis; White, Jonathan; Lobachevsky, Pavel; Winkler. David; Skene, Colin; Marcuccio, Sebastian). Intermediates 8a and 8b were treated with DMTCl to temporarily block the hydroxy group and then with diethyl pyrocarbonate to protect the benzimidazole nitrogens and afford fully protected intermediates 10. The transient DMT protection was removed by treatment with dilute TFA to give primary alcohols 11, which were then converted to final phosphoramidites 12 by phosphitylation with 2-cyanoethyl tetraisopropylphosphordiamidite.

Figure 3:
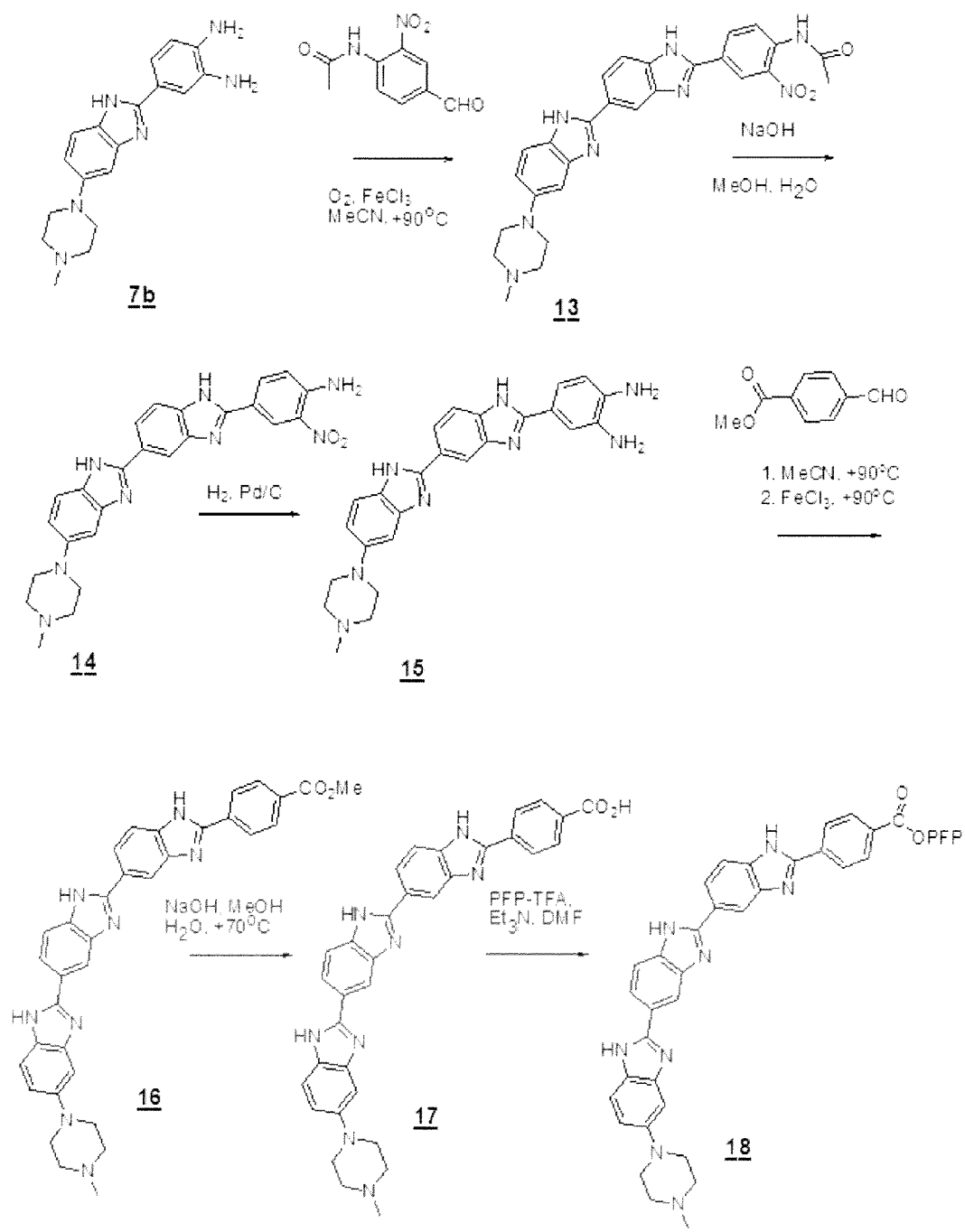
FIG. 3 shows a reaction scheme for the synthesis of an activated ester tri-benzimidazole type of minor groove binding agent.

FIG. 3 shows the preparation of a minor groove binder activated (PFP) ester, which can be used to synthesize tri-benzimidazole type minor groove binder phosphoramidites. Oxy dative cyclization (Synthetic Utility of Catalytic Fe(III)/Fe(II) Redox Cycling Towards Fused Heterocycles: A Facile Access to Substituted Benzimidazole, Bisbenzimidazole and Imidazopyridine Derivatives. Malvinder P. Singh*, Sanjita Sasmal, Wei Lu, Manashi N. Chatterjee. Synthesis, 2000(10): 1380-1390) of compound 7b and N-(4-formyl-2-nitrophenyl) acetamide gave compound 13. Deacetylation with NaOH afforded intermediate 14, which was then catalytically hydrogenated to yield diamine 15. Oxydative cyclization with methyl 4-formylbenzoate led to ester 16, which was then saponified and the resultant carboxy group of free acid 17 converted to pentafluorophenyl ester to give the desired activated minor groove binder 18. The PFP ester 18 can be reacted with various aminoalcohols to introduce linkers suitable for subsequent protection of the imidazole amines and phosphoramidite preparation.

Figure 4:
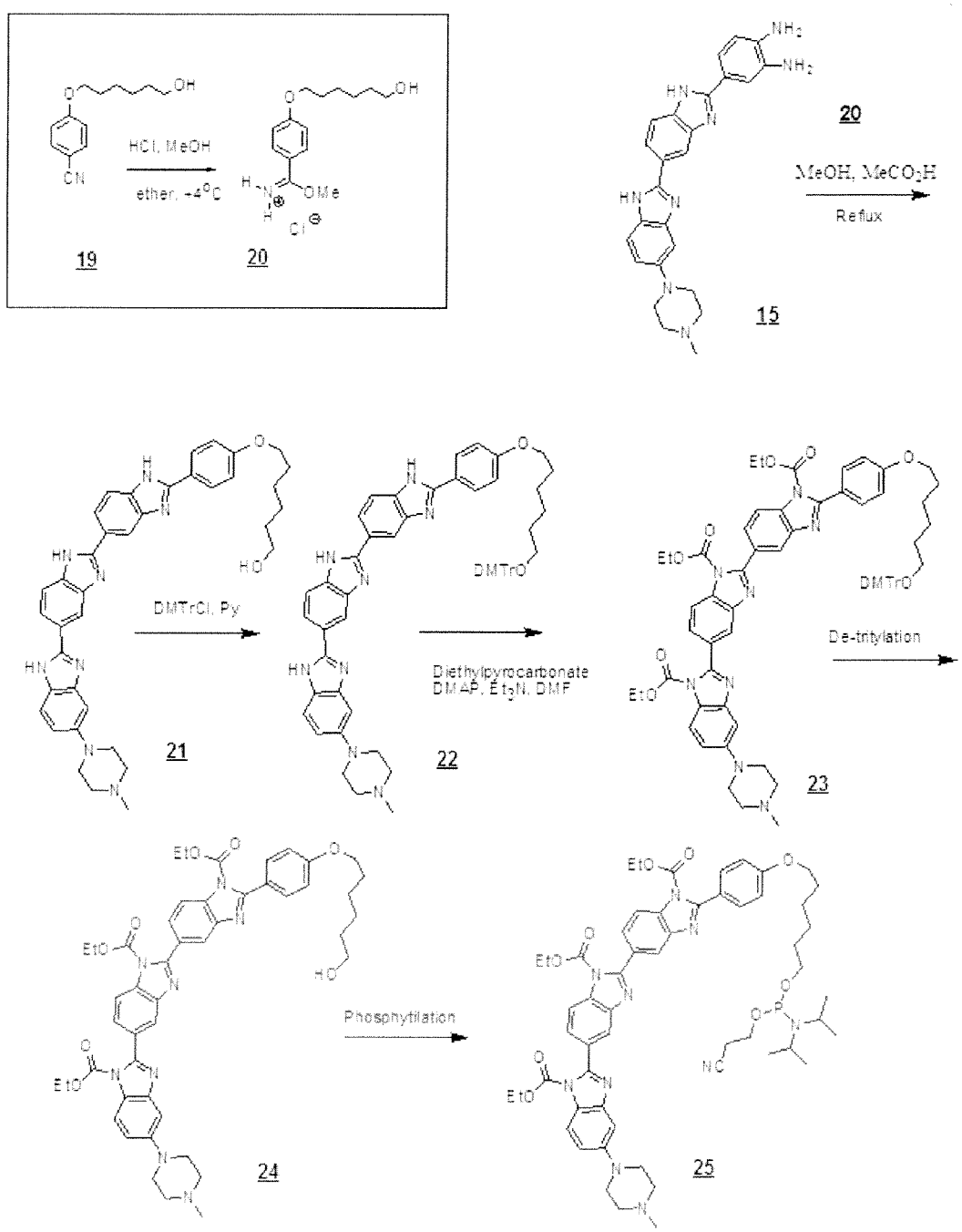
FIG. 4 shows a reaction scheme for the synthesis of tri-benzimidazole type minor groove binder phosphoramidites.

A tri-benzimidazole minor groove binder phosphoramidite was also prepared as shown in FIG. 4. The previously described (Fixed or Invertible Calixarene-Based Directional Shuttles. Teresa Pierro, Carmine Gaeta, Carmen Talotta, Agostino Casapullo, and Placido Neri Org. Lett. 2011, 13(10), 2650-2653.) compound 19 was converted to imidoester 20 in acidic methanol and condensed with diamine 15 forming 21 under acidic conditions according to Rajur et al (Hoechst 33258 Tethered by a Hexa(ethylene glycol) Linker to the 5'-Term ini of Oligodeoxynucleotide 15-Mers: Duplex Stabilization and Fluorescence Properties. Sharanabasava B. Rajur, Jordi Robles, Kristin Wiederholt, Robert G. Kuimelis, and Larry W. McLaughlin. J. Org. Chem., 1997, 62 (3), pp 523-529). The resulting free hydroxyl group of compound 21 was temporarily blocked by converting it into a DMT derivative (compound 22). This allowed subsequent protection of benzimidazole amines as ethylcarbamates (compound 23). The transient DMT group was removed by a treatment with dilute TFA to regenerate the free hydroxyl group, which was subsequently converted into desired phosphoramidite 25 by a reaction with 2-cyanoethyl tetraisopropylphosphordiamidite.

In certain embodiments a protecting group is employed that has a solubility which is compatible with oligonucleotide synthesis and allows efficient deprotection. As used herein a "protecting group" or "protected form thereof" refers to a grouping of atoms that when attached to a reactive group in a molecule masks, reduces or prevents that reactivity. Examples of protecting groups can be found in Greene and Wuts, 1991, Beaucage and Iyer, 1992, and Harrison and Harrison et al. 1971-1996. Representative amino protecting groups include formyl, acetyl, trifluoroacetyl, benzyl, benzyloxycarbonyl(CBZ), tert-butoxy carbonyl (Boc), ethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like (see also Boyle, 2000). Representative hydroxy protecting groups include those where the hydroxy group is either acylated or alkylated such as benzyl and trityl ethers as well as alkyl ethers, tetrahydropyranyl ethers, trialkylsilyl ethers and allyl ethers. Additionally, hydroxy groups can be protected by photoremovable groups such as alpha-methyl-6-nitopiperonyloxycarbonyl (McGall, 2001; Boyle, 2000).

In certain embodiments the phosphoramidites 5(a-d), 12(a-b) and 25 can be incorporated into an oligonucleotide on an automated synthesizer using standard oligonucleotide synthesis and deprotection protocols.

The practice of the present subject matter will employ, unless otherwise indicated, conventional techniques in organic chemistry, biochemistry, oligonucleotide synthesis and modification, bioconjugate chemistry, nucleic acid hybridization and related fields as are within the skill of the art. These techniques are fully explained in the literature (Ausubel, et al., 1987-1996; Gait, 1984; Eckstein, 1991).

The present methods of synthesizing minor groove binder phosphoramidites are amendable for use with other minor groove binders known in the art. Examples of known minor groove binding compounds of the prior art, which can, in accordance with the present methods, be converted to phosphoramidite derivatives include naturally occurring compounds and their synthetic analogs such as CC-1065, Duocarmycin SA, Duocarmycin A and Hoescht 33258 shown in Table 1 below. Additional analogs of Hoechst 33258 and Duocarmycin that can be converted to phosphoramidite derivatives according to the present methods are shown in Tables 2 and 3 below, respectively. Hoechst 3328 analogs have been disclosed by Reddy et al, 1999: Robles et al., 1996: Wiederholt et al, 1996; Bostock-Smith & Searle, 1999; Dasari et al. 2010; Sando et al., 2007; International Patent Publication No. WO 2007/016455; Jan et al., 2006; U.S. Publication No. 2006/166223; Tanada et al, 2006: and International Patent Publication No. WO 2005/082894. Duocarmycin analogs have been disclosed by Ichumura et al. 1990; Smith et al., 2000; Amishiro et al., 1999: Howard et al., 2002; Boger et al., 1994: Boger et al., 2001; Robertson, et al., 2010; MacMillan et al., 2008; Tichenor et al., 2V07; and Yamada et al., 2003. Although some of the analogs in Table 2 were synthesized as precursors to reactive intermediates, detailed synthetic methods are available in the art for their construction which could be modified to introduce non-reactive substituents. Two particular useful approaches are Tichenor et al, 129: 14092-14099 (2007) and Tichenor et al., 2006.

A variety of suitable CC-1065, Hoechst 33258 and duocarmycin, minor groove binders ("MGBs") have been described in the literature. See, for example, U.S. Pat. No. 5,801,155; Wemmer, et al. 1997; Walker, et al. 1997; Zimmer, & Wahnert, 1986; and Reddy, et al. 1999.

Suitable methods for introducing different linkers for attachment to MGBs are described in, for example, U.S. Pat. Nos. 5,512,677; 5,419,966; 5,696,251; 5,585,481; 5,942,610 and 5,736,626. Minor groove binder phosphoramidites with different linkers are also described.

Preferred minor groove binders are those selected from CC1065-, Hoechst 33258 and Duocarmycin-analogs. These analogs are representative of indole- and benzimidazole-based minor groove binders.

Particularly preferred minor groove binders include a dimer of 1,2-dihydro-(3H)-pyrrolo[3,2-e]indole-7-carboxylate (DPI$_2$), a trimer of 1,2-dihydro-(3H)-pyrrolo[3,2-e]indole-7-carboxylate (DPI$_3$), a tetramer of 1,2-dihydro-(3H)-pyrrolo[3,2-e]indole-7-carboxylate (DPI$_4$), and other minor groove binders. Additional MGB moieties that will find use in the practice of the present disclosure are disclosed in U.S. Pat. No. 5,801,155. In certain embodiments, the MGBs can have attached water solubility-enhancing groups (e.g., sugars or amino acids).

Other preferred minor groove binders are selected from the Hoechst 33258-analogs shown in Table 2 and Duocarmycin-analogs shown in Table 3. Those skilled in the art will appreciate that an appropriate linker can be introduced into these analogs suitable for the synthesis of a phosphoramidite. The current phosphoramidites are used to react on an automated oligonucleotide synthesizer to yield an oligonucleotide conjugate. Methods are known in the art to introduce halogen, cyano, amino, hydroxyl, —O-alkyl, alkyl, heteroalkyl, trifluoromethyl, carboxyl, heteroalkenyl, heteroalkynyl groups and the like into aryl rings.

More specifically, in Table 1 are examples where CC-1065, Duocannycin A, SA and Hoechst 33258 are substituted with —OH, —OCH$_3$, —CH$_3$ and —COOCH$_3$ groups. Similarly in Table 2 there are examples where Hoechst 33258 analogs are substituted with -tBu, —OH, —OCH$_3$, —CH$_3$, —NO$_2$, —OEt, —CH$_2$Cl, —Fl, —Br, —Cl, —I and —COOCH$_3$. Examples of substituted Duocannycin analogs in Table 3 include those substituted with —OH, —OCH$_3$, —CH$_3$, —NO$_2$, —CH$_2$Cl, —CH$_2$OH, —CH$_2$Br, —CH$_2$OS(=O)$_2$CH$_3$, —COOH, and —COOCH$_3$. The substitutions illustrated in Tables 1-3 are examples of substitutions capable of modulating the activity of a minor groove binder.

TABLE 1

Structures of CC-1065, Duocarmycin A, SA and Hoechst 33258

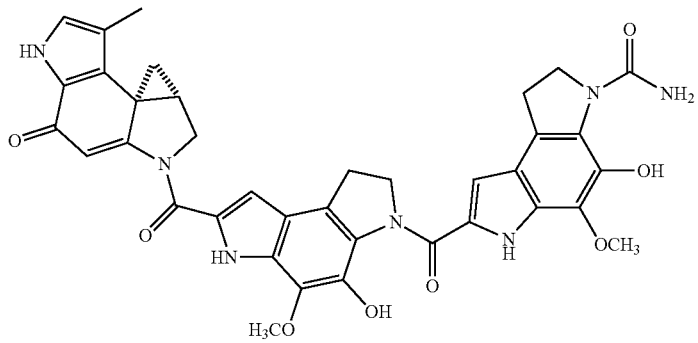

CC-1065

TABLE 1-continued
Structures of CC-1065, Duocarmycin A, SA and Hoechst 33258
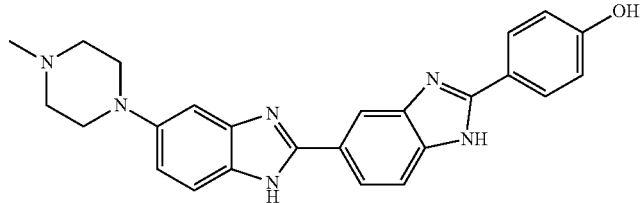 [SMILES: CN1CCN(c2ccc3[nH]c(-c4ccc5[nH]c(-c6ccc(O)cc6)nc5c4)nc3c2)CC1]
Hoechst 33258
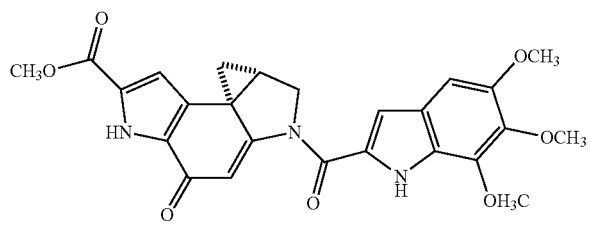
Duocarmycin SA
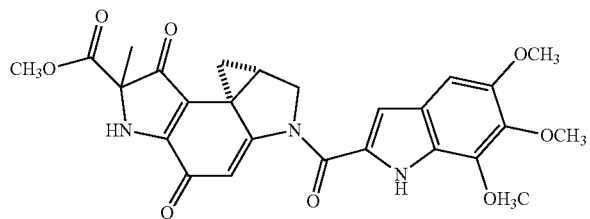
Duocarmycin A
TABLE 2
Hoechst 33258 Analogs
Analogs
Registry Number: 1185291-75-1
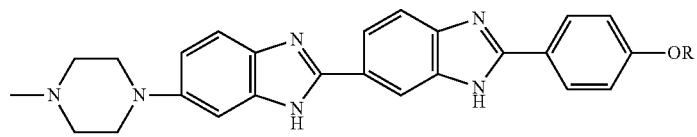
R = H, Hoechst 33258
R = $(CH_2CH_2O)_2CH_2CH_2NH_2$
R = $(CH_2CH_2O)_5CH_2CH_2NH_2$
R = $(CH_2)_6NH_2$
R = $(CH_2)_3COOH$ TABLE 2-continued
Hoechst 33258 Analogs
Analogs
Registry Number: 23623-06-5
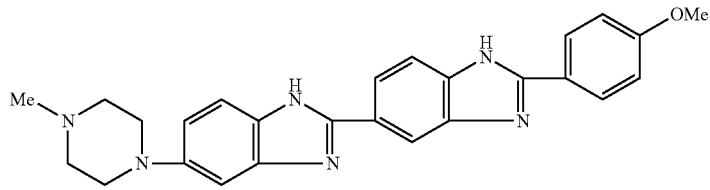 [SMILES: COc1ccc(-c2nc3cc(-c4nc5cc(N6CCN(C)CC6)ccc5[nH]4)ccc3[nH]2)cc1]
Registry Number: 1095815-04-5
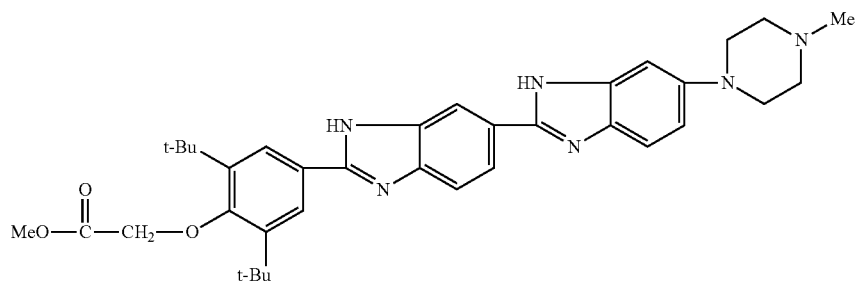 [SMILES: COC(=O)COc1c(C(C)(C)C)cc(-c2nc3ccc(-c4nc5ccc(N6CCN(C)CC6)cc5[nH]4)cc3[nH]2)cc1C(C)(C)C]
Registry Number: 126824-07-5
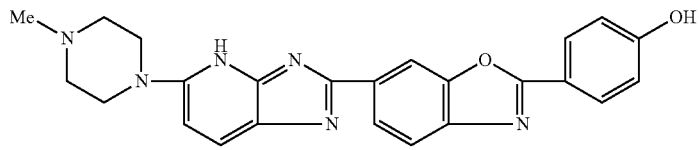 [SMILES: CN1CCN(c2ccc3nc(-c4ccc5nc(-c6ccc(O)cc6)oc5c4)nc-3[nH]2)CC1]
Registry Number: 158617-28-8
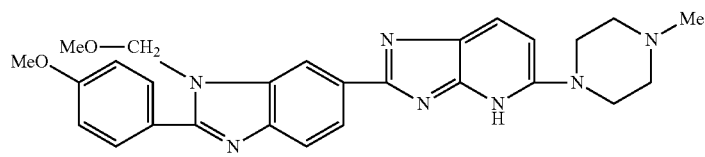 [SMILES: COCn1c(-c2ccc(OC)cc2)nc2ccc(-c3nc4ccc(N5CCN(C)CC5)[nH]c-4n3)cc21]
Registry Number: 126824-08-6
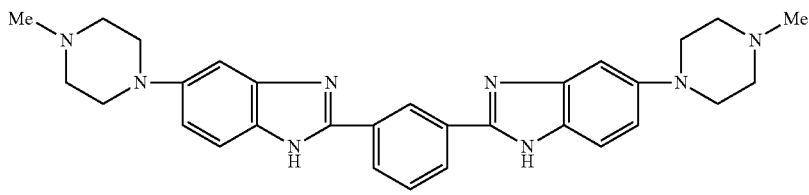 [SMILES: CN1CCN(c2ccc3[nH]c(-c4cccc(-c5nc6cc(N7CCN(C)CC7)ccc6[nH]5)c4)nc3c2)CC1]
Registry Number: 126824-04-2
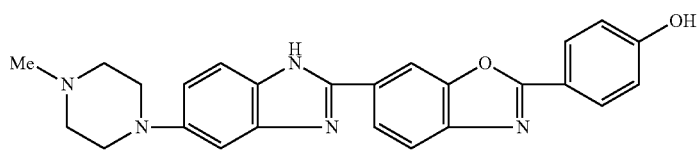 [SMILES: CN1CCN(c2ccc3[nH]c(-c4ccc5nc(-c6ccc(O)cc6)oc5c4)nc3c2)CC1]

TABLE 2-continued
Hoechst 33258 Analogs
Analogs
Registry Number: 126824-08-6
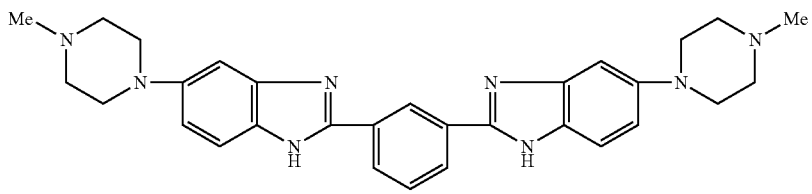 [SMILES: CN1CCN(c2ccc3[nH]c(-c4cccc(-c5nc6cc(N7CCN(C)CC7)ccc6[nH]5)c4)nc3c2)CC1]
Registry Number: 1196688-95-5
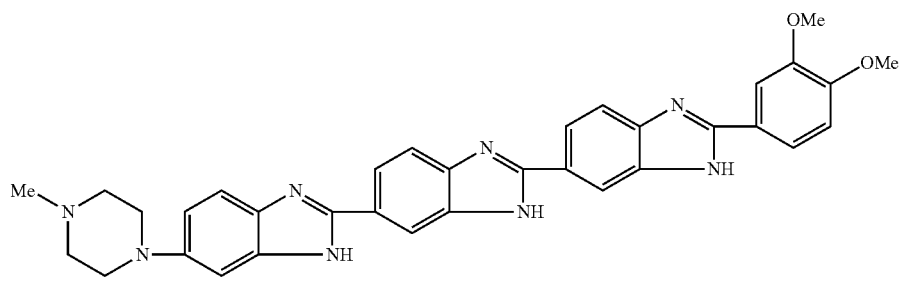 [SMILES: COc1ccc(-c2nc3ccc(-c4nc5ccc(-c6nc7ccc(N8CCN(C)CC8)cc7[nH]6)cc5[nH]4)cc3[nH]2)cc1OC]
Registry Number: 1195161-65-9
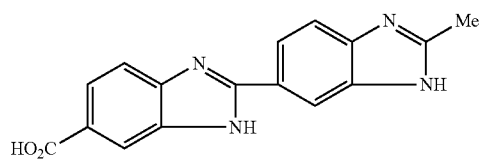
•2 HCl
Registry Number: 1186195-36-7
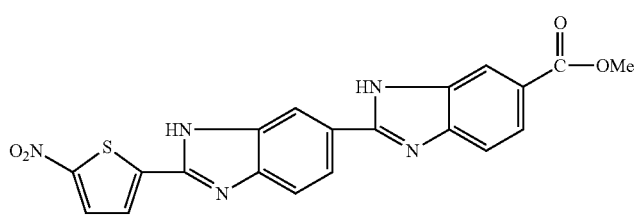 [SMILES: COC(=O)c1ccc2nc(-c3ccc4nc(-c5ccc([N+](=O)[O-])s5)[nH]c4c3)[nH]c2c1]
Registry Number: 1027786-29-3
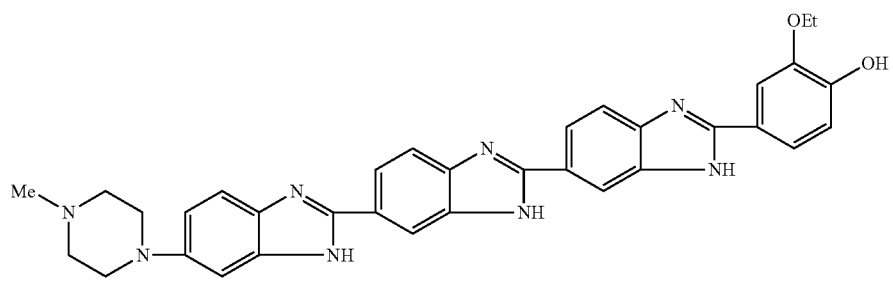 [SMILES: CCOc1cc(-c2nc3ccc(-c4nc5ccc(-c6nc7ccc(N8CCN(C)CC8)cc7[nH]6)cc5[nH]4)cc3[nH]2)ccc1O]

TABLE 2-continued
Hoechst 33258 Analogs
Analogs
Registry Number: 1108199-19-4
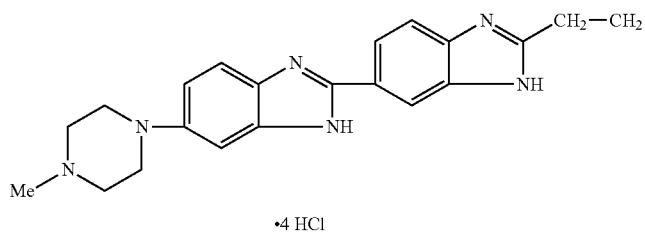 [SMILES: CCc1nc2ccc(-c3nc4ccc(N5CCN(C)CC5)cc4[nH]3)cc2[nH]1]
•4 HCl
Registry Number: 807310-26-5
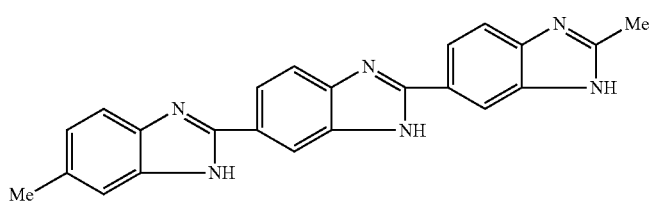 [SMILES: Cc1ccc2nc(-c3ccc4nc(-c5ccc6nc(C)[nH]c6c5)[nH]c4c3)[nH]c2c1]
Registry Number: 807310-25-4
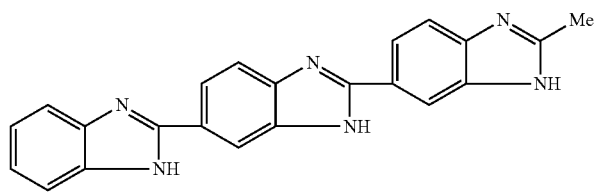 [SMILES: Cc1nc2ccc(-c3nc4ccc(-c5nc6ccccc6[nH]5)cc4[nH]3)cc2[nH]1]
Registry Number: 763140-28-9
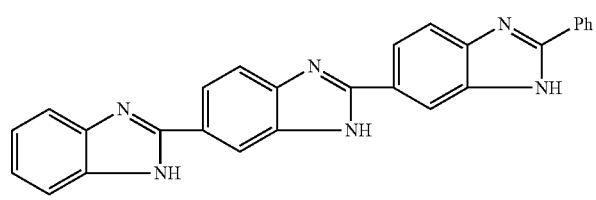 [SMILES: c1ccc(-c2nc3ccc(-c4nc5ccc(-c6nc7ccccc7[nH]6)cc5[nH]4)cc3[nH]2)cc1]
Registry Number: 502173-54-8
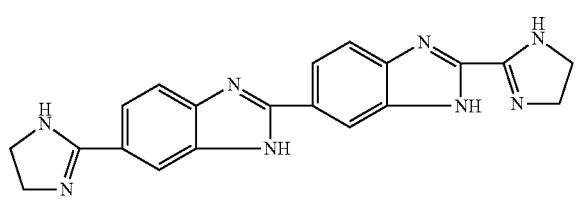 [SMILES: c1cc2nc(-c3ccc4nc(C5=NCCN5)[nH]c4c3)[nH]c2cc1C1=NCCN1]
Registry Number: 392287-23-9
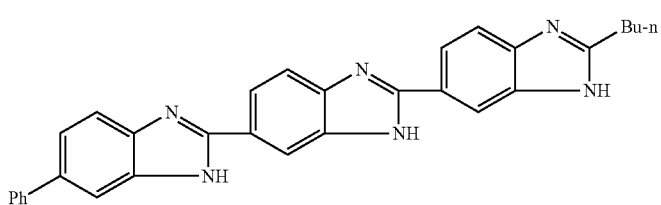

TABLE 2-continued
Hoechst 33258 Analogs
Analogs
Registry Number: 392287-22-8
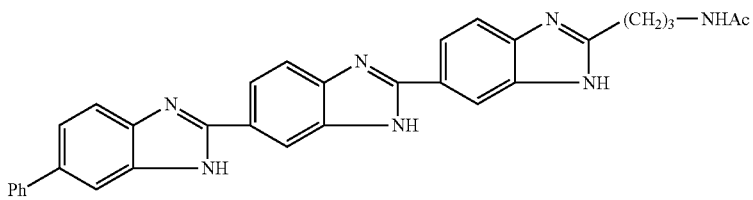
Registry Number: 392287-21-7
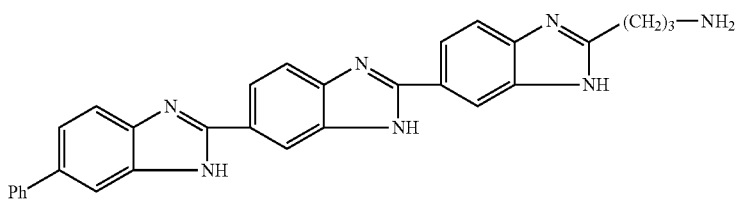
Registry Number: 392287-20-6
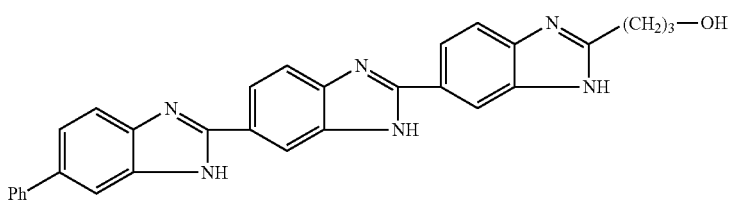
Registry Number: 392287-17-1
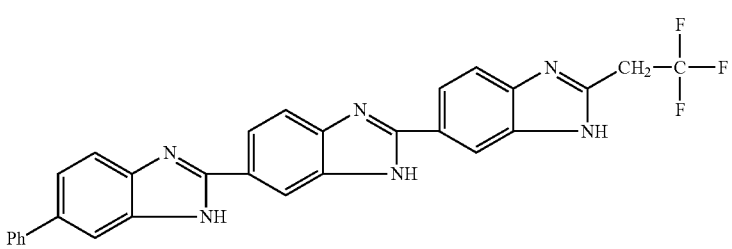 [SMILES: FC(F)(F)Cc1nc2ccc(-c3nc4ccc(-c5nc6ccc(-c7ccccc7)cc6[nH]5)cc4[nH]3)cc2[nH]1]
Registry Number: 392287-16-0
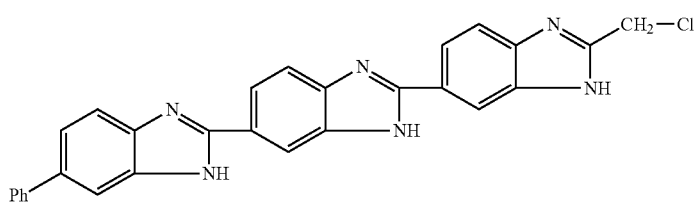 [SMILES: ClCc1nc2ccc(-c3nc4ccc(-c5nc6ccc(-c7ccccc7)cc6[nH]5)cc4[nH]3)cc2[nH]1]
Registry Number: 392287-15-9
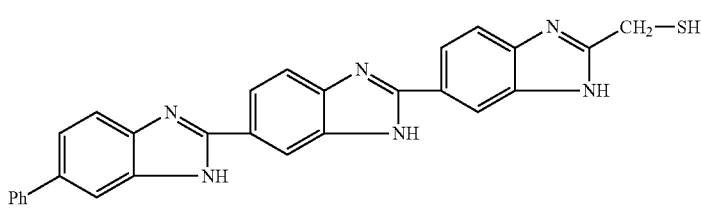 [SMILES: SCc1nc2ccc(-c3nc4ccc(-c5nc6ccc(-c7ccccc7)cc6[nH]5)cc4[nH]3)cc2[nH]1]

TABLE 2-continued
Hoechst 33258 Analogs
Analogs
Registry Number: 391903-25-6
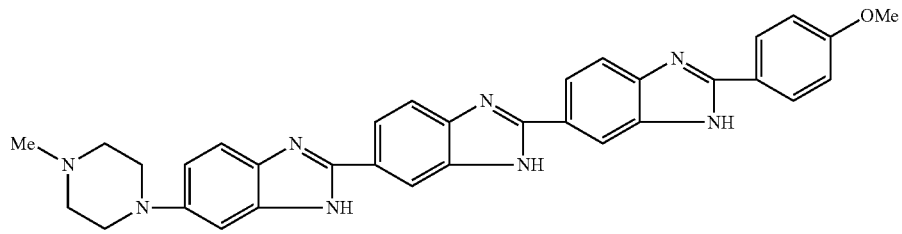 [SMILES: COc1ccc(-c2nc3ccc(-c4nc5ccc(-c6nc7ccc(N8CCN(C)CC8)cc7[nH]6)cc5[nH]4)cc3[nH]2)cc1]
Registry Number: 391903-25-6
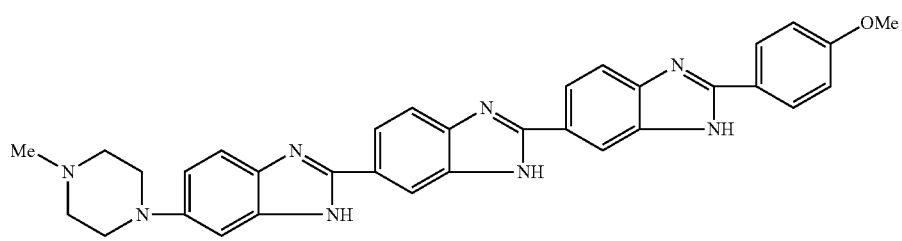 [SMILES: COc1ccc(-c2nc3ccc(-c4nc5ccc(-c6nc7ccc(N8CCN(C)CC8)cc7[nH]6)cc5[nH]4)cc3[nH]2)cc1]
Registry Number: 351335-08-5
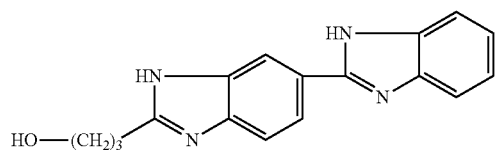
Registry Number: 351335-07-4
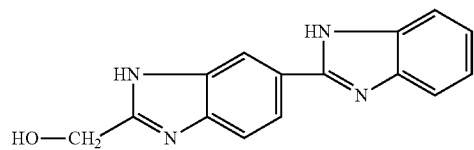 [SMILES: OCc1nc2ccc(-c3nc4ccccc4[nH]3)cc2[nH]1]
Registry Number: 334685-29-9
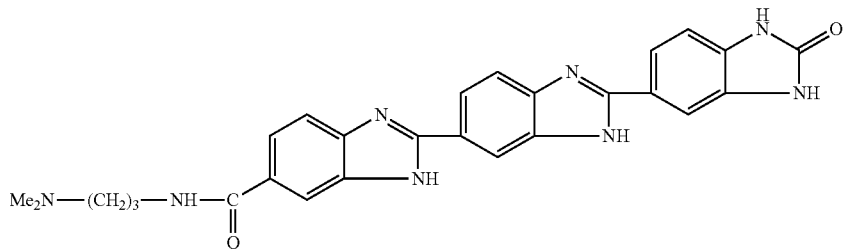
Registry Number: 334685-27-7
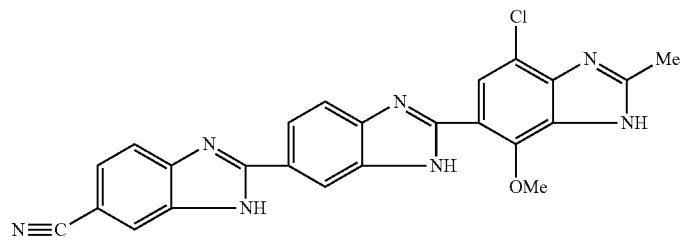 [SMILES: COc1c(-c2nc3ccc(-c4nc5ccc(C#N)cc5[nH]4)cc3[nH]2)cc(Cl)c2nc(C)[nH]c12]

TABLE 2-continued
Hoechst 33258 Analogs
Analogs
Registry Number: 334685-25-5
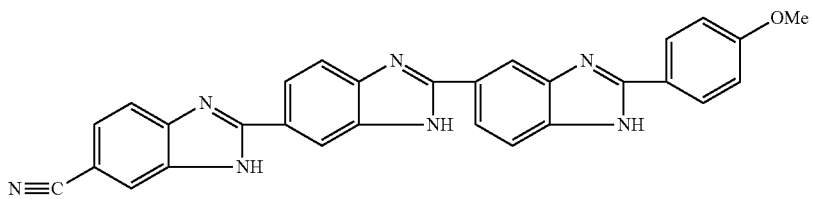 [SMILES: COc1ccc(-c2nc3cc(-c4nc5ccc(-c6nc7ccc(C#N)cc7[nH]6)cc5[nH]4)ccc3[nH]2)cc1]
Registry Number: 334685-21-1
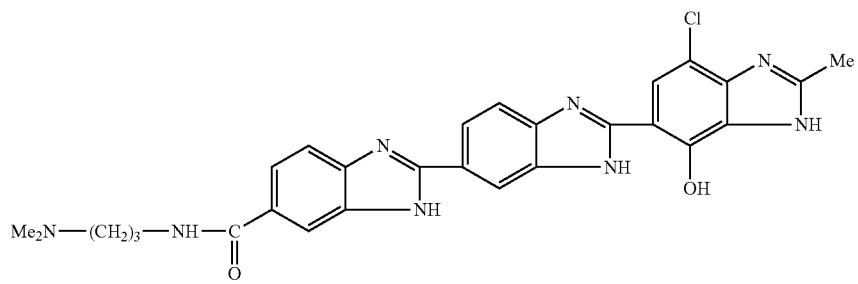
Registry Number: 304854-73-7
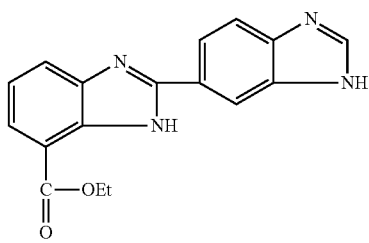 [SMILES: CCOC(=O)c1cccc2nc(-c3ccc4nc[nH]c4c3)[nH]c12]
Registry Number: 319916-61-5
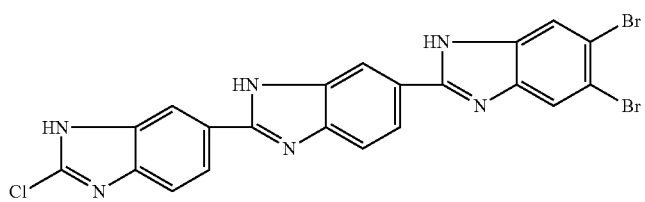 [SMILES: Clc1nc2ccc(-c3nc4ccc(-c5nc6cc(Br)c(Br)cc6[nH]5)cc4[nH]3)cc2[nH]1]
Registry Number: 319916-61-5
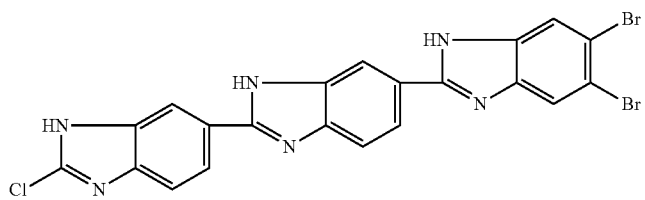 [SMILES: Clc1nc2ccc(-c3nc4ccc(-c5nc6cc(Br)c(Br)cc6[nH]5)cc4[nH]3)cc2[nH]1]
Registry Number: 308362-22-3
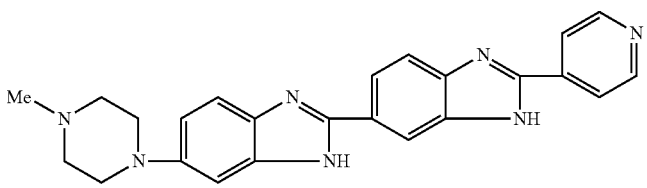 [SMILES: CN1CCN(c2ccc3nc(-c4ccc5nc(-c6ccncc6)[nH]c5c4)[nH]c3c2)CC1]

TABLE 2-continued
Hoechst 33258 Analogs
Analogs
Registry Number: 308362-21-2
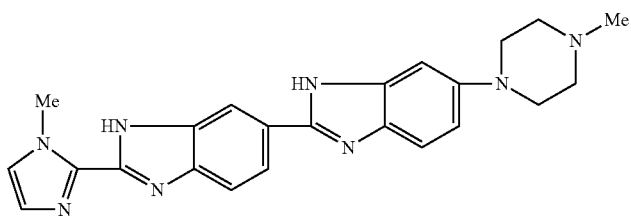 [SMILES: CN1CCN(c2ccc3nc(-c4ccc5nc(-c6nccn6C)[nH]c5c4)[nH]c3c2)CC1]
Registry Number: 288579-81-7
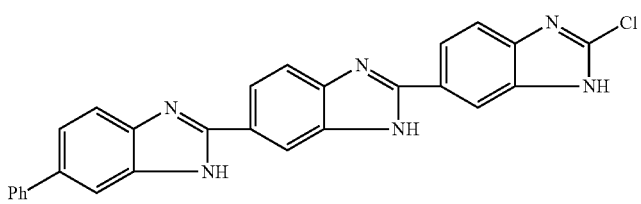 [SMILES: Clc1nc2ccc(-c3nc4ccc(-c5nc6ccc(-c7ccccc7)cc6[nH]5)cc4[nH]3)cc2[nH]1]
Registry Number: 263707-97-7
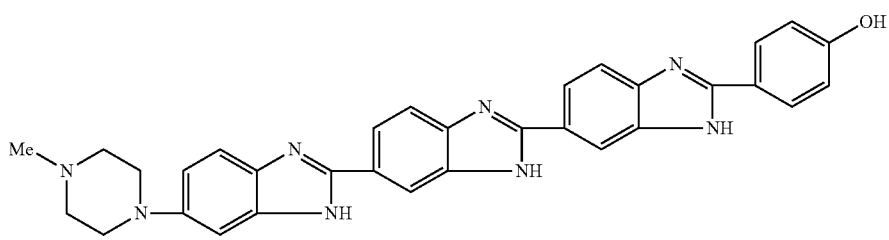 [SMILES: CN1CCN(c2ccc3nc(-c4ccc5nc(-c6ccc7nc(-c8ccc(O)cc8)[nH]c7c6)[nH]c5c4)[nH]c3c2)CC1]
Registry Number: 263707-96-6
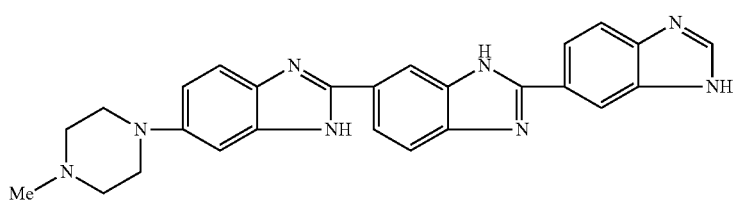 [SMILES: CN1CCN(c2ccc3nc(-c4ccc5nc(-c6ccc7nc[nH]c7c6)[nH]c5c4)[nH]c3c2)CC1]
Registry Number: 237429-72-0
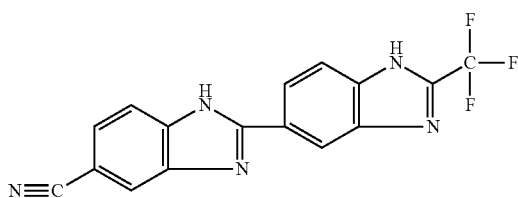 [SMILES: N#Cc1ccc2[nH]c(-c3ccc4[nH]c(C(F)(F)F)nc4c3)nc2c1]
Registry Number: 237429-59-3
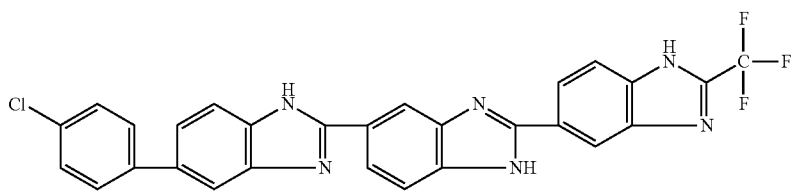 [SMILES: FC(F)(F)c1nc2cc(-c3nc4cc(-c5nc6cc(-c7ccc(Cl)cc7)ccc6[nH]5)ccc4[nH]3)ccc2[nH]1]

TABLE 2-continued
Hoechst 33258 Analogs
Analogs
Registry Number: 237429-58-2
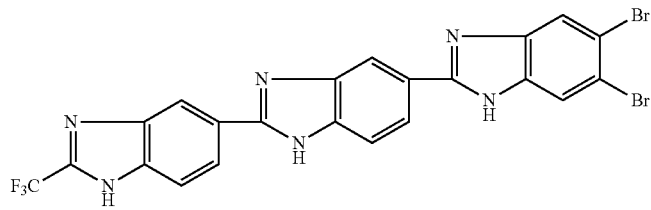 [SMILES: FC(F)(F)c1nc2cc(-c3nc4cc(-c5nc6cc(Br)c(Br)cc6[nH]5)ccc4[nH]3)ccc2[nH]1]
Registry Number: 237429-57-1
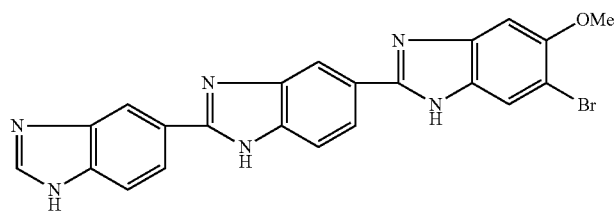 [SMILES: COc1cc2nc(-c3ccc4[nH]c(-c5ccc6[nH]cnc6c5)nc4c3)[nH]c2cc1Br]
Registry Number: 237429-55-9
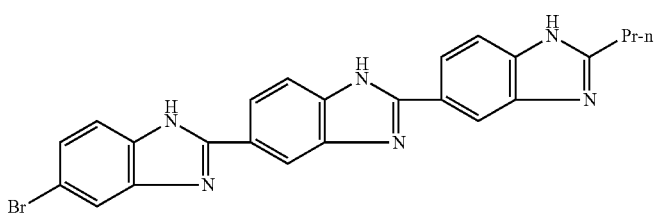
Registry Number: 237429-53-7
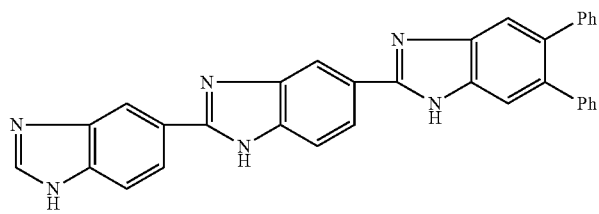 [SMILES: c1ccc(-c2cc3nc(-c4ccc5[nH]c(-c6ccc7[nH]cnc7c6)nc5c4)[nH]c3cc2-c2ccccc2)cc1]
Registry Number: 237429-52-6
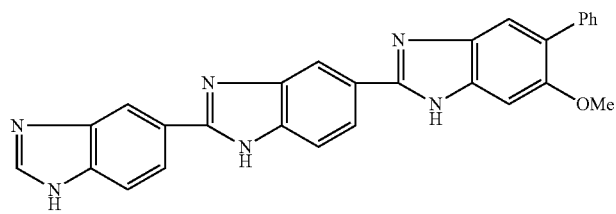 [SMILES: COc1cc2[nH]c(-c3ccc4[nH]c(-c5ccc6[nH]cnc6c5)nc4c3)nc2cc1-c1ccccc1]
Registry Number: 237429-51-5
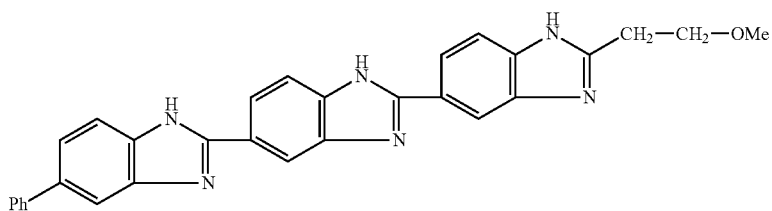 [SMILES: COCCc1nc2cc(-c3nc4cc(-c5nc6cc(-c7ccccc7)ccc6[nH]5)ccc4[nH]3)ccc2[nH]1]

TABLE 2-continued
Hoechst 33258 Analogs
Analogs
Registry Number: 237429-50-4
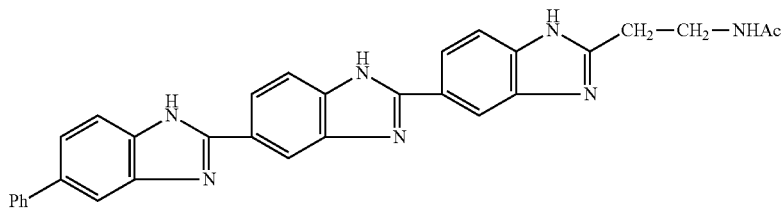 [SMILES: CC(=O)NCCc1nc2cc(-c3nc4cc(-c5nc6cc(-c7ccccc7)ccc6[nH]5)ccc4[nH]3)ccc2[nH]1]
Registry Number: 237429-49-1
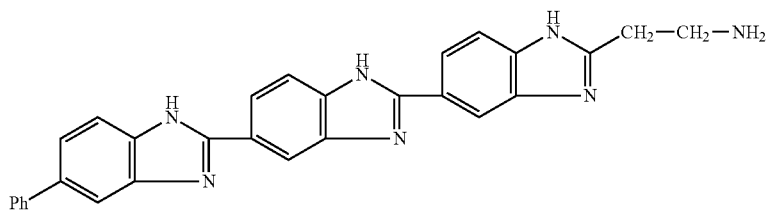 [SMILES: NCCc1nc2cc(-c3nc4cc(-c5nc6cc(-c7ccccc7)ccc6[nH]5)ccc4[nH]3)ccc2[nH]1]
Registry Number: 237429-48-0
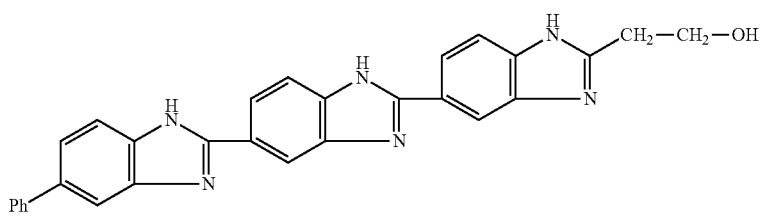 [SMILES: OCCc1nc2cc(-c3nc4cc(-c5nc6cc(-c7ccccc7)ccc6[nH]5)ccc4[nH]3)ccc2[nH]1]
Registry Number: 237429-46-8
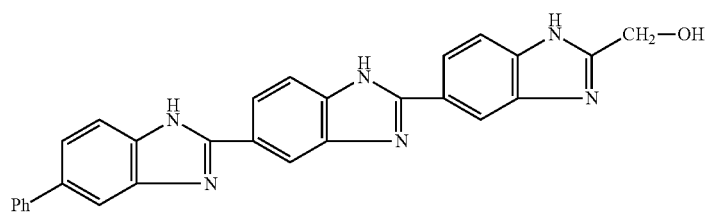 [SMILES: OCc1nc2cc(-c3nc4cc(-c5nc6cc(-c7ccccc7)ccc6[nH]5)ccc4[nH]3)ccc2[nH]1]
Registry Number: 213137-22-5
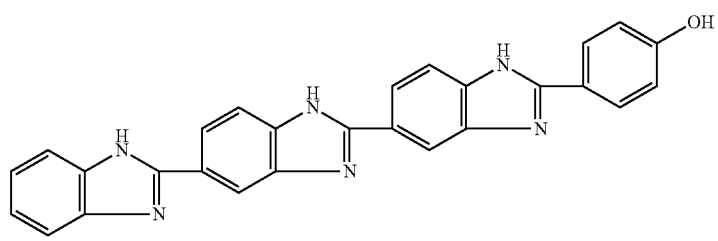 [SMILES: Oc1ccc(-c2nc3cc(-c4nc5cc(-c6nc7ccccc7[nH]6)ccc5[nH]4)ccc3[nH]2)cc1]
Registry Number: 205749-96-8
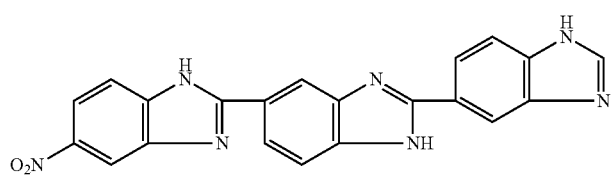 [SMILES: O=[N+]([O-])c1ccc2[nH]c(-c3ccc4[nH]c(-c5ccc6[nH]cnc6c5)nc4c3)nc2c1]

TABLE 2-continued
Hoechst 33258 Analogs
Analogs
Registry Number: 208774-56-5
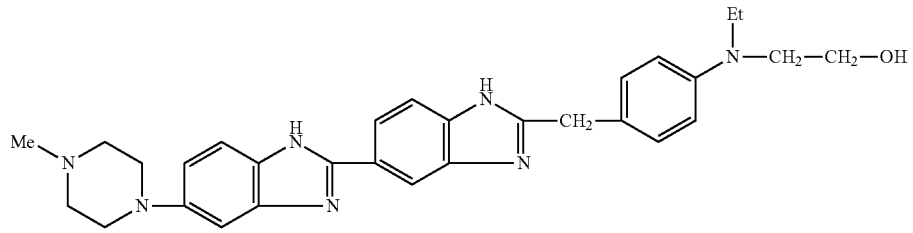 [SMILES: CCN(CCO)c1ccc(Cc2nc3cc(-c4nc5cc(N6CCN(C)CC6)ccc5[nH]4)ccc3[nH]2)cc1]
Registry Number: 205749-98-0
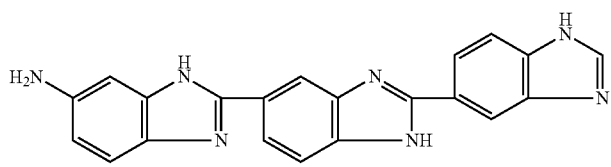 [SMILES: Nc1ccc2nc(-c3ccc4[nH]c(-c5ccc6[nH]cnc6c5)nc4c3)[nH]c2c1]
Registry Number: 205749-97-9
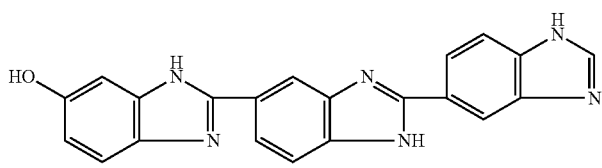 [SMILES: Oc1ccc2nc(-c3ccc4[nH]c(-c5ccc6[nH]cnc6c5)nc4c3)[nH]c2c1]
Registry Number: 205749-94-6
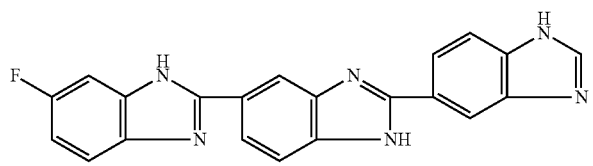 [SMILES: Fc1ccc2nc(-c3ccc4[nH]c(-c5ccc6[nH]cnc6c5)nc4c3)[nH]c2c1]
Registry Number: 205749-95-7
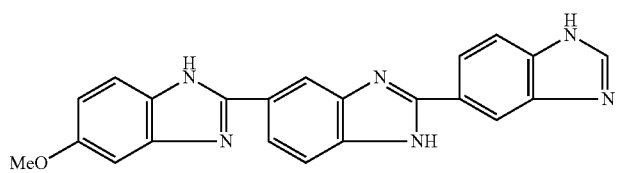 [SMILES: COc1ccc2[nH]c(-c3ccc4[nH]c(-c5ccc6[nH]cnc6c5)nc4c3)nc2c1]
Registry Number: 205749-93-5
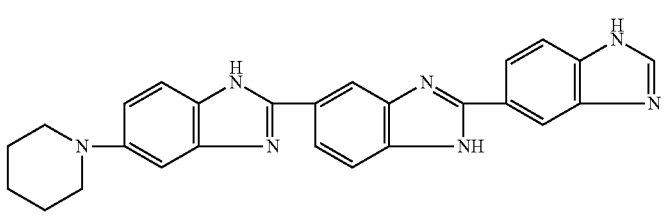 [SMILES: c1nc2cc(-c3nc4cc(-c5nc6cc(N7CCCCC7)ccc6[nH]5)ccc4[nH]3)ccc2[nH]1]
Registry Number: 192879-69-9
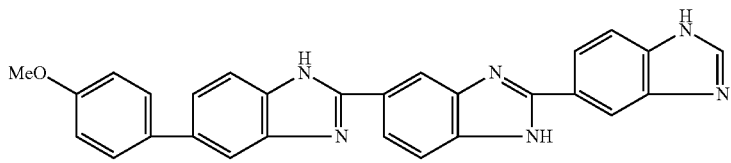 [SMILES: COc1ccc(-c2ccc3[nH]c(-c4ccc5[nH]c(-c6ccc7[nH]cnc7c6)nc5c4)nc3c2)cc1]

TABLE 2-continued
Hoechst 33258 Analogs
Analogs
Registry Number: 182496-22-6
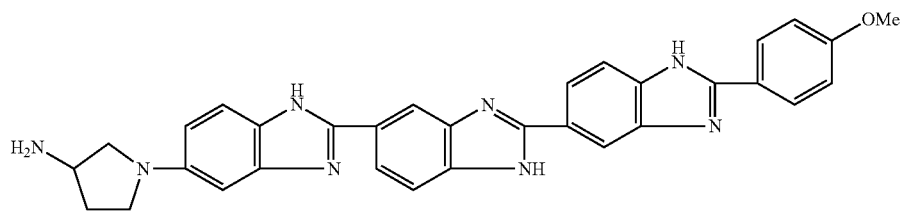 [SMILES: COc1ccc(-c2nc3cc(-c4nc5cc(-c6nc7cc(N8CCC(N)C8)ccc7[nH]6)ccc5[nH]4)ccc3[nH]2)cc1]
Registry Number: 192879-69-9
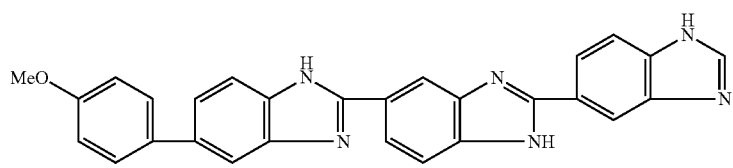 [SMILES: COc1ccc(-c2ccc3[nH]c(-c4ccc5[nH]c(-c6ccc7[nH]cnc7c6)nc5c4)nc3c2)cc1]
Registry Number: 182496-21-5
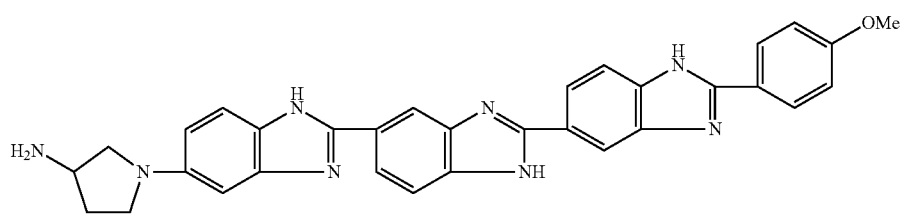 [SMILES: COc1ccc(-c2nc3cc(-c4nc5cc(-c6nc7cc(N8CCC(N)C8)ccc7[nH]6)ccc5[nH]4)ccc3[nH]2)cc1]
Registry Number: 178481-76-0
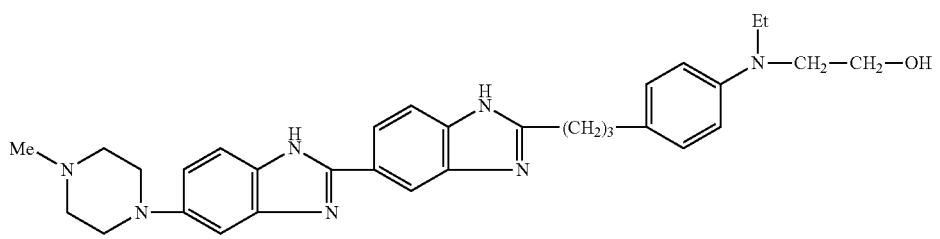
Registry Number: 167959-27-5
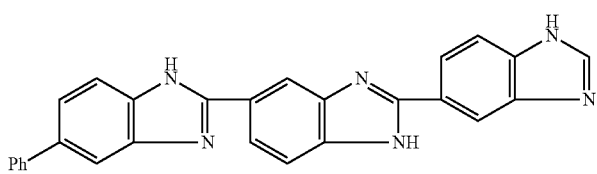 [SMILES: c1ccc(-c2ccc3[nH]c(-c4ccc5[nH]c(-c6ccc7[nH]cnc7c6)nc5c4)nc3c2)cc1]
Registry Number: 178481-76-0
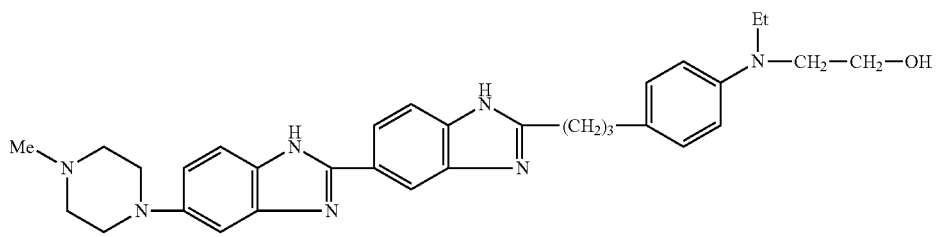

TABLE 2-continued
Hoechst 33258 Analogs
Analogs
Registry Number: 167959-26-4
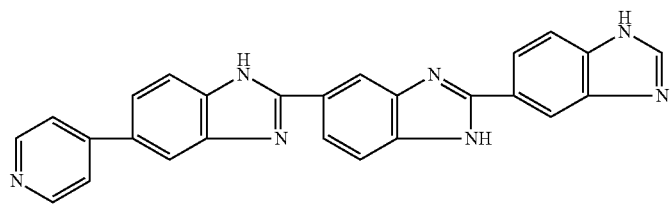 [SMILES: c1cc(-c2ccc3[nH]c(-c4ccc5[nH]c(-c6ccc7[nH]cnc7c6)nc5c4)nc3c2)ccn1]
Registry Number: 167959-24-2
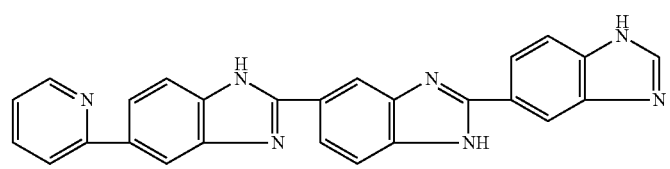 [SMILES: c1ccc(-c2ccc3[nH]c(-c4ccc5[nH]c(-c6ccc7[nH]cnc7c6)nc5c4)nc3c2)nc1]
Registry Number: 167959-17-3
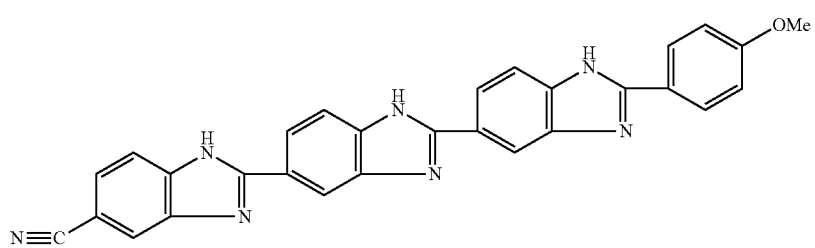 [SMILES: COc1ccc(-c2nc3cc(-c4nc5cc(-c6nc7cc(C#N)ccc7[nH]6)ccc5[nH]4)ccc3[nH]2)cc1]
Registry Number: 167959-22-0
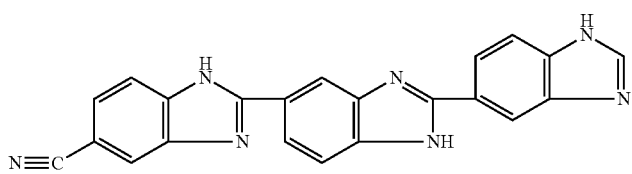 [SMILES: N#Cc1ccc2[nH]c(-c3ccc4[nH]c(-c5ccc6[nH]cnc6c5)nc4c3)nc2c1]
Registry Number: 23491-53-4
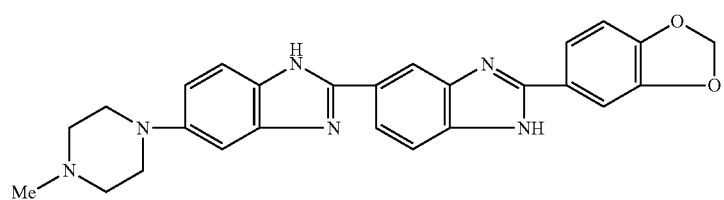 [SMILES: CN1CCN(c2ccc3[nH]c(-c4ccc5[nH]c(-c6ccc7c(c6)OCO7)nc5c4)nc3c2)CC1]
Registry Number: 167959-13-9
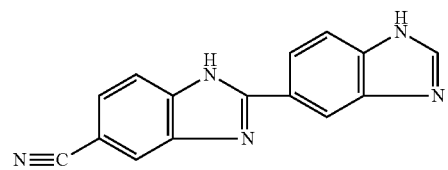 [SMILES: N#Cc1ccc2[nH]c(-c3ccc4[nH]cnc4c3)nc2c1]

TABLE 3
Duocarmycin Analogs
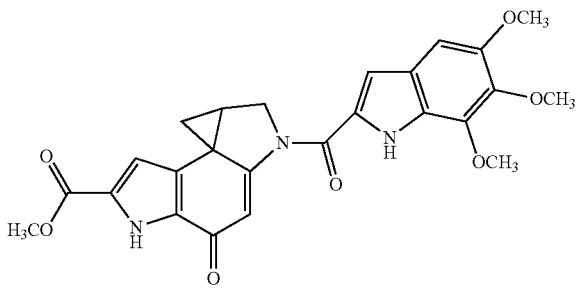 [SMILES: COC(=O)c1cc2c([nH]1)C(=O)C=C1N(C(=O)c3cc4cc(OC)c(OC)c(OC)c4[nH]3)CC3CC123]
Duocarmycin SA
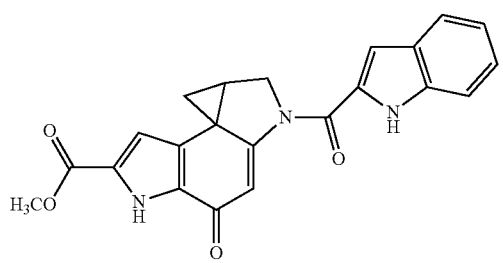 [SMILES: COC(=O)c1cc2c([nH]1)C(=O)C=C1N(C(=O)c3cc4ccccc4[nH]3)CC3CC123]
Duocarmycin SA indole
Registry Number: 502170-52-7
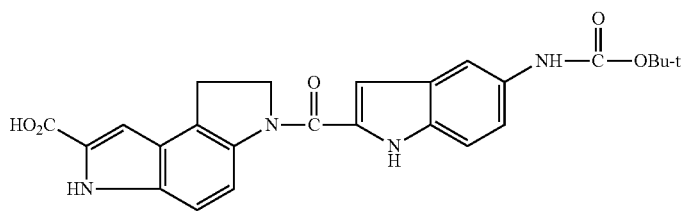
Registry Number: 1132799-23-5
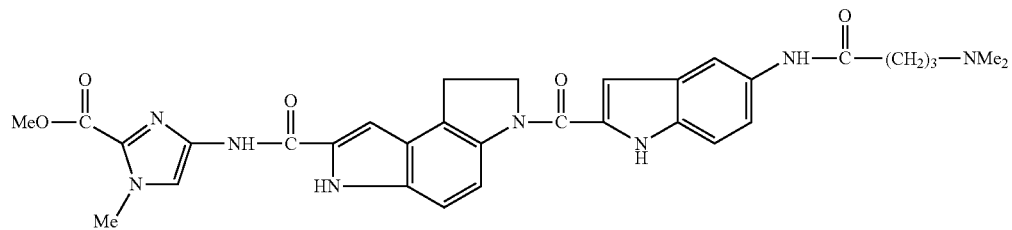
Registry Number: 502170-52-7
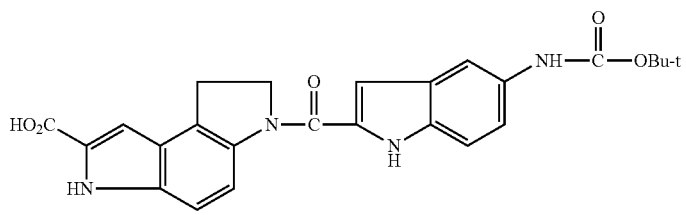

TABLE 3-continued
Duocarmycin Analogs
Registry Number: 454691-95-3
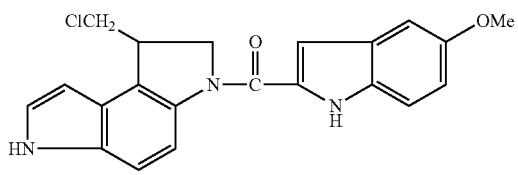
Registry Number: 454691-87-3
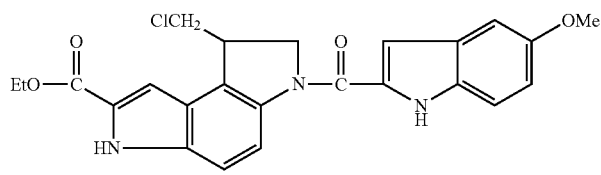
Registry Number: 372953-90-7
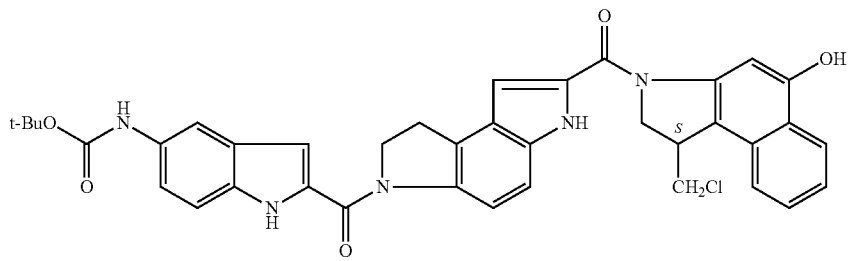
Absolute stereochemistry.
Registry Number: 292071-20-6
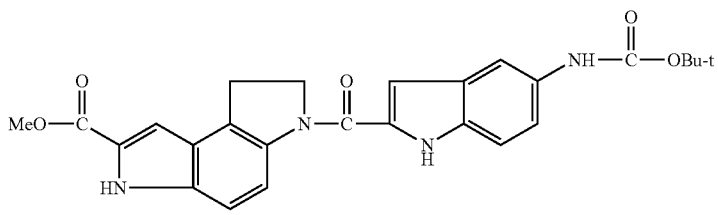
Registry Number: 292069-78-4
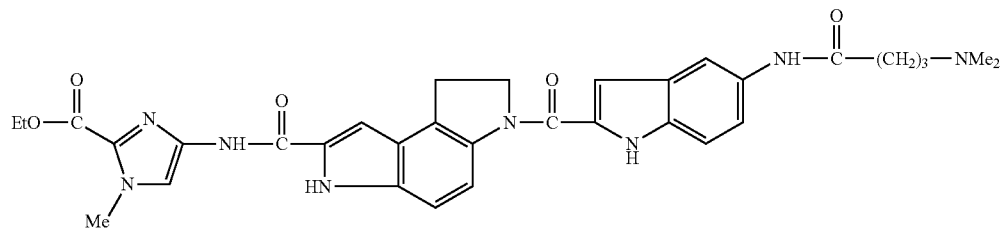
Registry Number: 292069-56-8
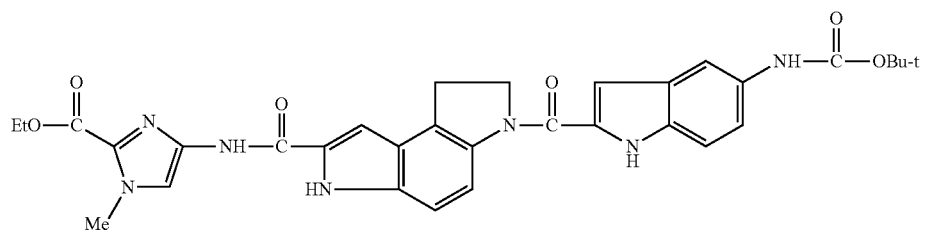

TABLE 3-continued
Duocarmycin Analogs
Registry Number: 129368-61-2
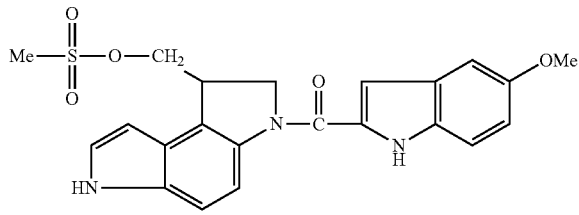 [SMILES: COc1ccc2[nH]c(C(=O)N3CC(COS(C)(=O)=O)c4c3ccc3[nH]ccc43)cc2c1]
Registry Number: 123194-36-5
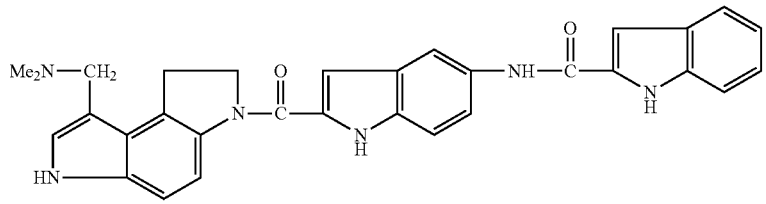 [SMILES: CN(C)Cc1c[nH]c2ccc3c(c12)CCN3C(=O)c1cc2cc(NC(=O)c3cc4ccccc4[nH]3)ccc2[nH]1]
Registry Number: 1106759-80-1
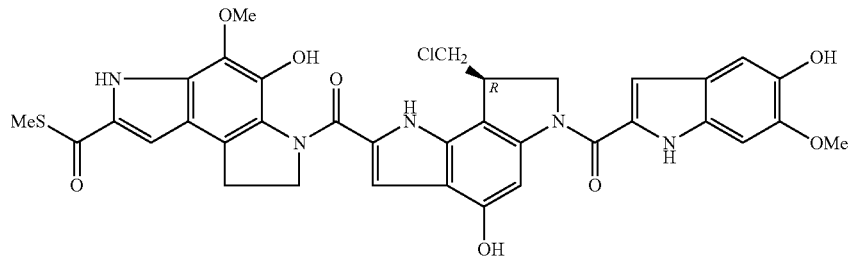
Absolute stereochemistry. Rotation (−).
Registry Number: 1106759-60-7
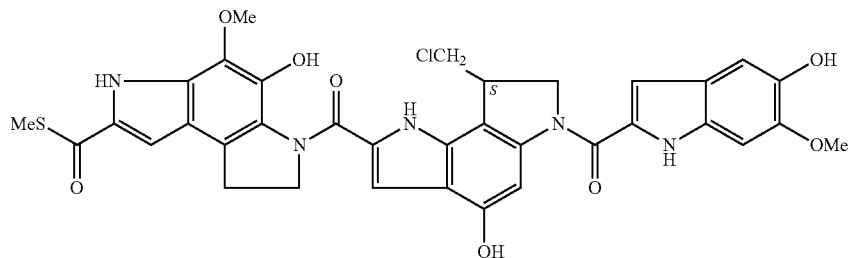
Absolute stereochemistry. Rotation (+).
Registry Number: 1026693-48-0
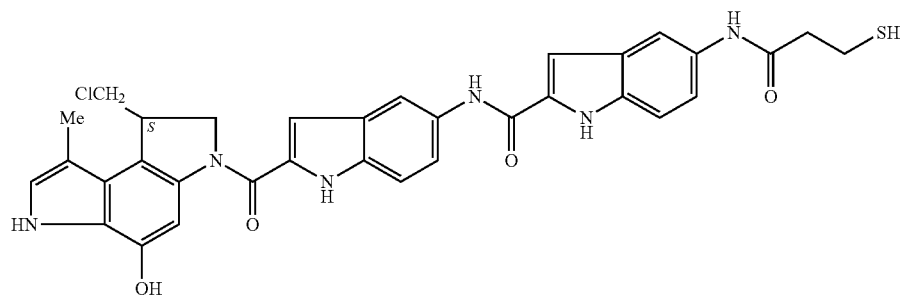
Absolute stereochemistry.

TABLE 3-continued
Duocarmycin Analogs
Registry Number: 277318-27-1
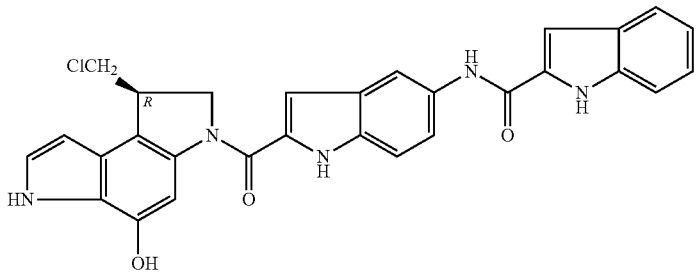
Absolute stereochemistry. Rotation (−).
Registry Number: 277317-81-4
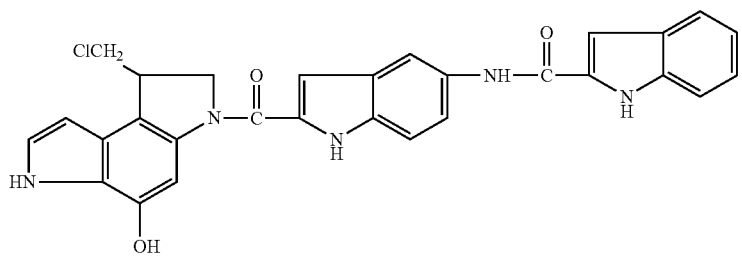
Registry Number: 224321-47-5
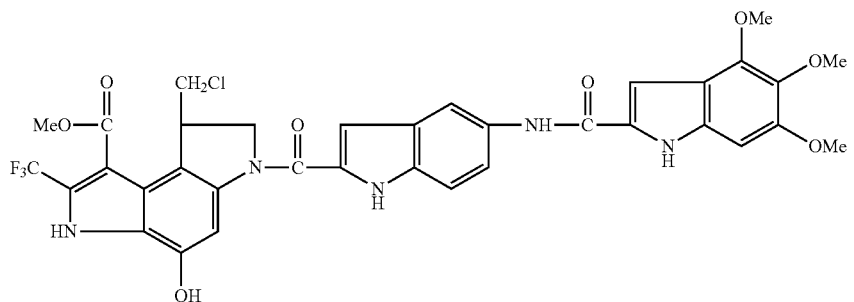
Registry Number: 190060-44-7
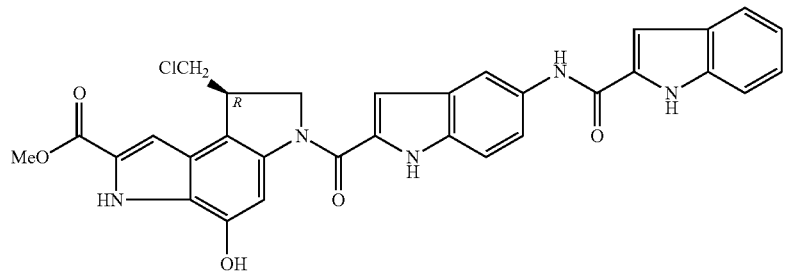
Absolute stereochemistry. Rotation (−).

TABLE 3-continued
Duocarmycin Analogs
Registry Number: 157822-97-4
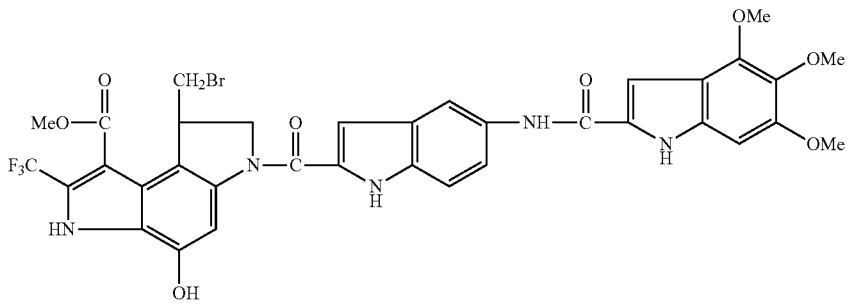
Registry Number: 138761-90-7
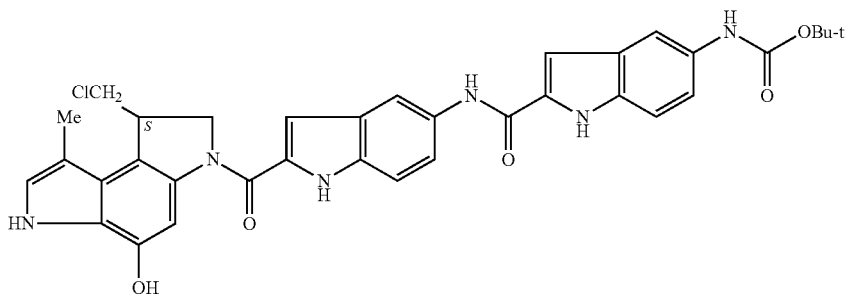
Absolute stereochemistry.
Registry Number: 138730-89-9
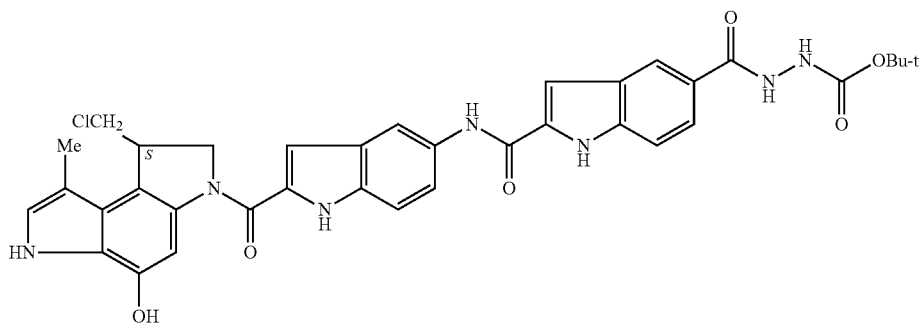
Absolute stereochemistry.
Registry Number: 138730-86-6
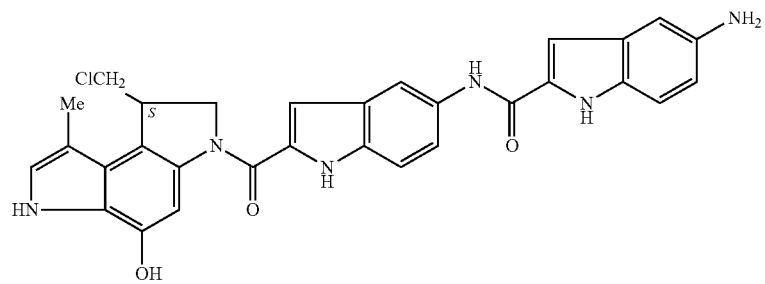
Absolute stereochemistry.

TABLE 3-continued
Duocarmycin Analogs
Registry Number: 137548-34-6
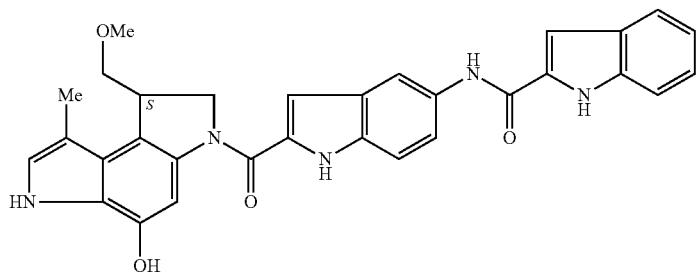
Absolute stereochemistry.
Registry Number: 108833-16-5
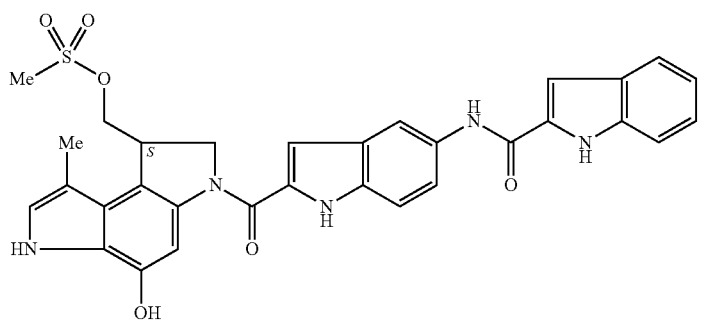
Absolute stereochemistry.
Registry Number: 101134-75-2
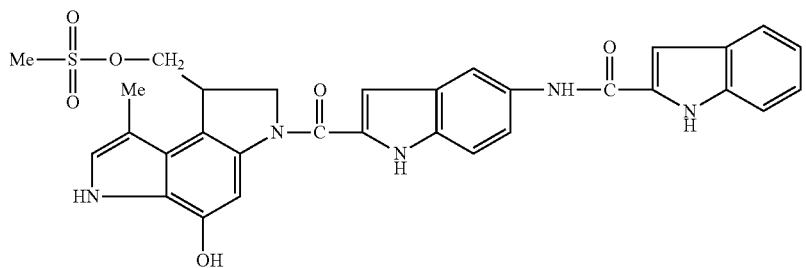 [SMILES: Cc1c[nH]c2c(O)cc3c(c12)C(COS(C)(=O)=O)CN3C(=O)c1cc2cc(NC(=O)c3cc4ccccc4[nH]3)ccc2[nH]1]
Registry Number: 157141-36-1
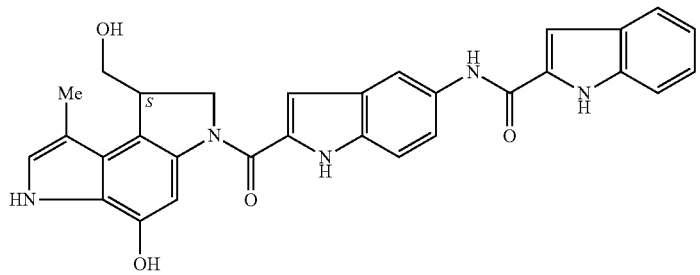
Absolute stereochemistry.

TABLE 3-continued

Duocarmycin Analogs

Registry Number: 182360-44-7

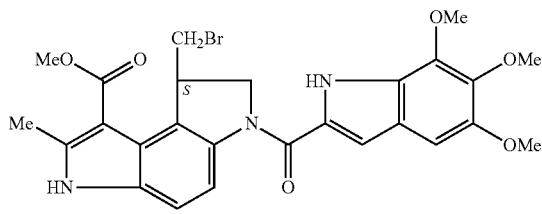

Absolute stereochemistry.

Registry Number: 182360-46-9

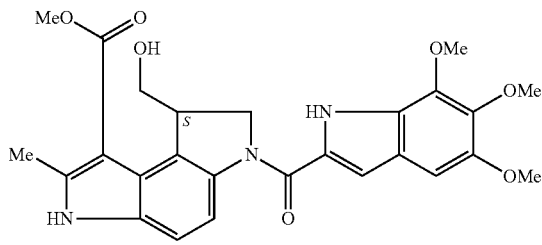

Absolute stereochemistry.

The present methods of synthesizing minor groove binder phosphoramidites are also amendable for use with diamidine phenylindole (DAPI) or some furamidine (Boykin D. W. J. Braz. Chem. Soc. (2002) V. 13, 6, 763-771.) analogs. More generally, these methods are amendable to minor groove binding ligands comprising a heteroaromatic amine.

Particularly preferred minor groove binder phosphoramidites may include compounds of the following formulas II and III:

Formula II

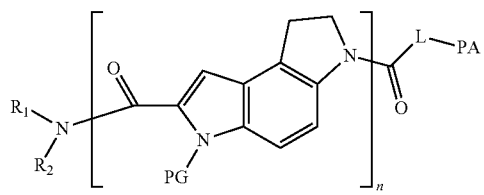

Formula III

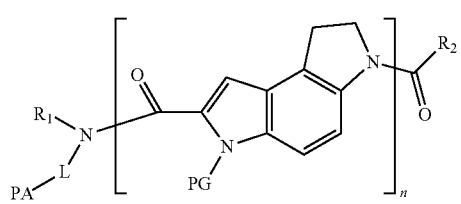

wherein $R^1$ and $R^2$ are each independently PG, L, $C_{1-8}$ alkyl, $C_{1-8}$ heteroalkyl, protected $C_{1-8}$ heteroalkyl, —($CH_2CH_2O)_nCH_2CH_3$ where n=1 to 8, or $R^1$ and $R^2$ form a 5 or 6 member ring structure which may contain 0, 1 or 2 hetero atoms selected from O, S and N; n=1 to 4; L is a linker which is acyclic, cyclic, aromatic or a combination thereof, having from 4 to 50 atoms, exclusive of hydrogens that fill available valences, selected from a group consisting of C, N, O, P, and S; PG is a protecting group; and PA is a phosphoramidite group.

Other particularly preferred minor groove binder phosphoramidites may also include compounds of the following formulas IV and V:

Formula IV

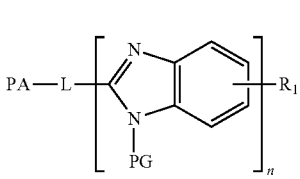

Formula V

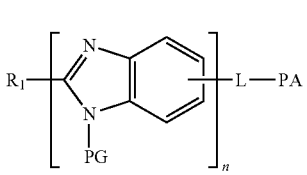

wherein $R_1$ is L, $C_{1-8}$ alkyl, $C_{1-8}$ heteroalkyl, protected $C_{1-8}$ heteroalkyl, —($CH_2CH_2O)_nCH_2CH_3$ where n=1 to 8, substituted or unsubstituted aryl and heteroaryl; n=1 to 4; L is a linker which is acyclic, cyclic, aromatic or a combination thereof, having from 4 to 50 atoms, exclusive of hydrogens that fill available valences, selected from a group consisting of C, N, O, P, and S; PG is a protecting group; and PA is a phosphoramidite group.

Minor groove binder oligonucleotide conjugates have been used as primers, probes (U.S. Pat. No. 6,312,984), miRNA antagonists (US Application Publication No. 2011/0172289), gene expression inhibitors (Kawashima et al., Nucl. Acids Symp. Ser (Oxf) 49: 327-328 (2005)), and for sequence-specific arrest of primer extension (Afonina et a PNAS, 93: 3199-3204 (1996)).

Depending on the intended application, the MGB group may be attached at the 3' end, 5' end, internally or at multiple locations within a nucleic acid sequence.

In general, conjugation of a MGB to a terminus of an oligonucleotide would provide the greatest degree of hybrid stability, since melting of an oligonucleotide duplex begins at the termini. The intended use of the MGB-oligonucleotide conjugate may also place limitations on the location of the conjugated MGB. For example, if an oligonucleotide is designed to be used as a primer, the 3'-hydroxy group must be free and capable of being elongated by a polymerizing enzyme. Alternatively, an assay that requires an oligonucleotide possessing a labeled 5'-end would require 3'-end attachment of a MGB.

The location of a MGB within a MGB-modified oligonucleotide conjugate can also affect the discriminatory properties of such a conjugate. An unpaired region within a duplex will result in changes in the shape of the minor groove in the vicinity of the mispaired base(s). Since MGBs fit best within the minor groove of a perfectly-matched DNA duplex, mismatches resulting in shape changes in the minor groove would reduce the binding strength of an MGB to a region containing a mismatch. Hence, the ability of an MGB to stabilize such a hybrid would be decreased, thereby increasing the ability of an MGB-oligonucleotide conjugate to discriminate a mismatch from a perfectly-matched duplex. On the other hand, if a mismatch lies outside of the region complementary to an MGB-oligonucleotide conjugate, discriminatory ability for unconjugated and MGB-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of MGB-oligonucleotides conjugates in this context lies in the fact that much shorter oligonucleotides (i.e. 20-mers or shorter) compared to those used in the prior art, having greater discriminatory powers, can be used, due to the pronounced stabilizing effect of MGB conjugation.

The present disclosure is generally not limited to minor groove binders; it may also be applied to phosphoramidites of molecules of various functions as long as they possess at least one heteroaromatic amine that requires proper protection.

EXAMPLES

The following examples are provided to illustrate, but not to limit, the presently claimed subject matter.

Example 1

Figure 5:
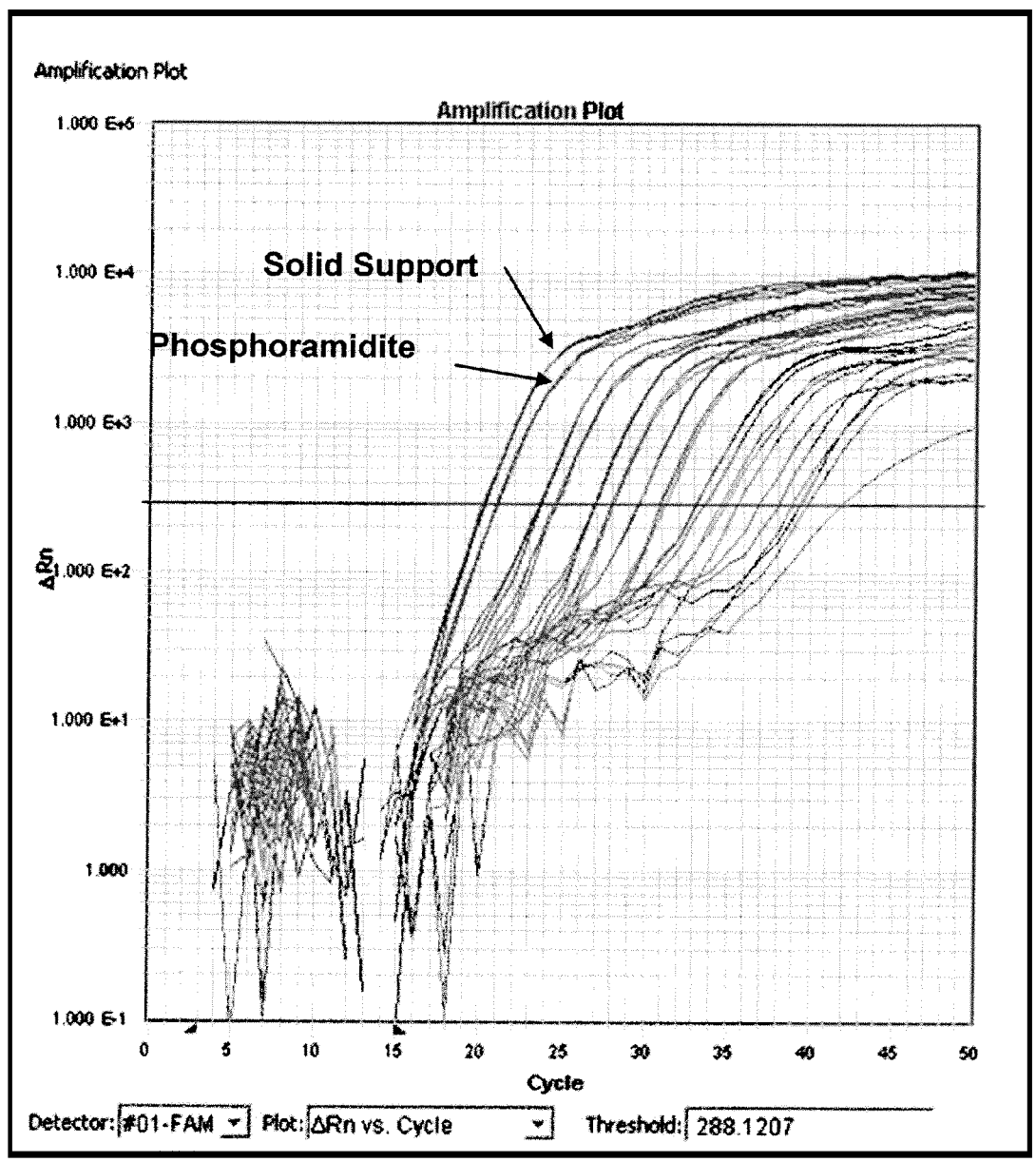
FIG. 5 shows a comparison of the performance of oligonucleotide probes synthesized with DPI$_3$ phosphoramidite and on a previously developed DPI$_3$-polystyrene solid support in a Varicella-Zoster Virus ("VZV") PCR assay.

This example compares the performance of oligonucleotide probes synthesized with $DPI_3$ phosphoramidite 5d prepared according to the present methods and on probes synthesized on a $DPI_3$-polystyrene solid support (as described in U.S. Pat. No. 7,381,818) in a Varicella-Zoster Virus ("VZV") PCR assay. The primers, probes and protocol for the VZV assay have been reported previously (Afonina et al., 2007). Briefly 10 μL of sample nucleic acid was added to 20 μL assay reagents and the assay was performed in an ABI 7900 thermocycler incubating at 50° C. for 2 min, denature at 95° C. for 2 min, using 50 cycles of 15 sec at 95° C., 30 sec at 50° C. and 30 sec at 72° C. A standard 10 fold serial dilution from $10^6$ to 10 copies was used. The $C_t$ values observed with the VZV probe synthesized on a solid support and that of the probes synthesized with the phosphoramidite of the present disclosure are very similar over the titration range, indicating similar performance as shown in FIG. 5.

Example 2

This example illustrates the synthesis of minor groove binder phosphoramidites 5a-d.

Synthesis of Compound 2a

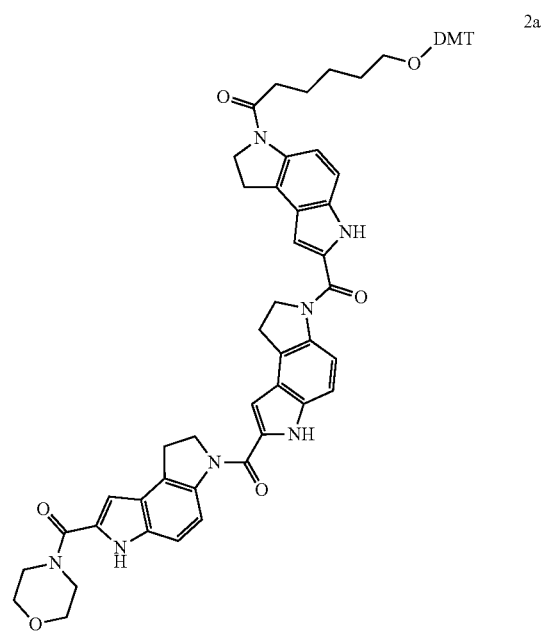

Morpholine (0.27 g, 2.60 mmol) was added to a suspension of compound 1 (2.5 g, 2.17 mmol) in DMF (35 ml) and triethylamine (0.439 g, 4.34 mmol). After being stirred for 1 h the reaction was concentrated and diluted with methanol (50 ml). The precipitated material was isolated by filtration to give a thick yellow-brownish paste, which was then washed with methanol (3×20 ml) and vacuum dried to afford compound 2a (2.0 g, 1.89 mmol, 87% yield) as a yellow-brown solid. The crude product was sufficiently pure to be used in the next step without additional purification.

Synthesis of Compound 2b

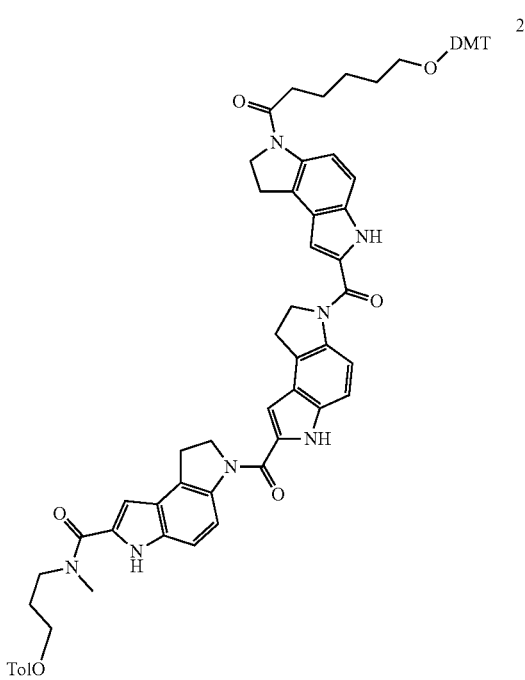

A solution of 9-fluorenylmethoxycarbonyl chloride (15.22 g, 58.85 mmol) in dichloromethane (100 ml) was added over 1 h to an ice-cooled solution of 3-methylamino-1-propanol (5.25 g, 58.85 mmol) and triethylamine (9.0 ml, 64.74 mmol) in dichloromethane (50 ml). The resultant suspension was left overnight at −18° C., and then diluted with brine. The organic phase was separated, dried over MgSO$_4$ and concentrated in vacuo. The residue was purified on silica eluting with 1:4 ethyl acetate/dichloromethane to give (9H-fluoren-9-yl)methyl 3-hydroxypropylmethylcarbamate (100% yield). p-Toluoyl chloride (4.26 g, 27.56 mmol) was added dropwise over 10 min to an ice-cooled solution of (9H-fluoren-9-yl) methyl 3-hydroxypropylmethylcarbamate (7.8 g, 25.05 mmol) in pyridine (100 ml). The resultant mixture NA as stirred for 2 h at 0° C., concentrated in vacuo and redissolved in ethyl acetate. The solution was washed with 10% citric acid and brine, then separated, dried over MgSO$_4$ and concentrated in vacuo. The residue was purified on silica eluting with 30% ethyl acetate/hexane to give (9H-fluoren-9-yl)methyl 3-(4-methylbenzoyloxy)propylmethylcarbamate (97% yield). A solution of (9H-fluoren-9-yl)methyl 3-(4-methylbenzoyloxy)propylmethylcarbamate (0.91 g, 2.12 mmol) and triethylamine (5.0 ml) in DMF (5 ml) was stirred for 1 h at +80° C. The resultant mixture was cooled to room temperature and compound 1 (2.01 g, 1.74 mmol) was added. The reaction was diluted with DMF (5), stirred for 2 days, and then diluted with ether (100 ml). The precipitated solid was isolated by filtration, washed with ether and vacuum dried to afford compound 2b (89% yield) as a pale solid, which was sufficiently pure to be used in the next step without additional purification.

Synthesis of Compound 2c

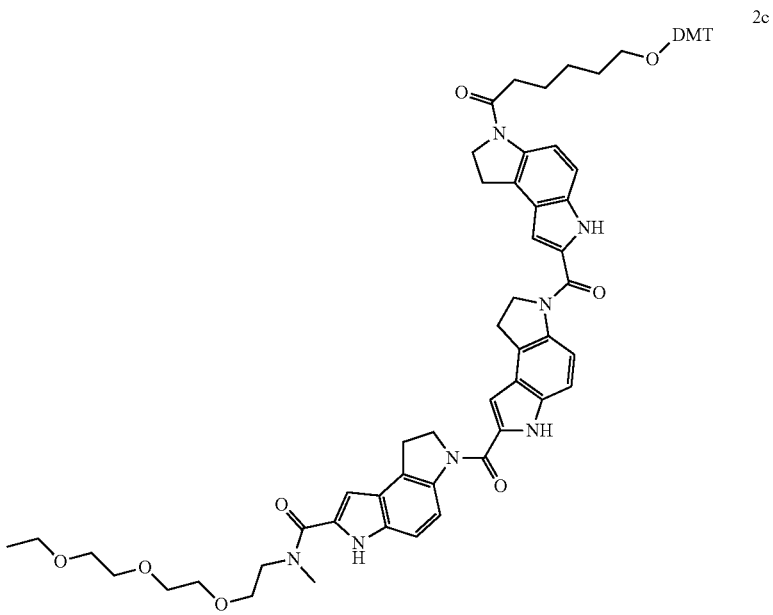

p-Toluenesulfonyl chloride (12.583 g, 66.0 mmol) was added to an ice-cooled solution of triethylene glycol monoethyl ether (10.484 ml, 10.694 g, 60.0 mmol) in pyridine (9.7 ml). After being stirred for 3.5 h the reaction was diluted with 10% hydrochloric acid and extracted with ethyl acetate. The organic phase was separated, washed with 10% hydrochloric acid, dried over MgSO$_4$ and concentrated in vacuo to afford sufficiently pure p-toluenesulfonate of triethylene glycol monoethyl ether (19.92 g, 59.9 mmol, 100%) as a reddish liquid. The obtained tosylate (19.5 g, 58.7 mmol) was dissolved in 33% solution of methylamine in methanol (24 ml) and refluxed for 18 h, cooled and concentrated in vacuo. The residue was dissolved in 5% HCl and washed 3 times with dichloromethane. The combined organic solution was back extracted with 5% HCl. All aqueous extracts were combined and mixed with a solution of sodium hydroxide (6 g) in water (14 ml). The resultant solution was extracted with dichloromethane. The combined organic solution was washed with water, dried over MgSO$_4$ and concentrated in vacuo to afford crude 2-(2-(2-ethoxyethoxy)ethoxy)-N-methylethanamine (6.50 g) as a yellowish liquid, which was then used further without additional purification. The crude 2-(2-(2-ethoxyethoxy)ethoxy)-N-methylethanamine (0.426 g, 1.86 mmol) was added to suspension of compound 1 (1.07 g, 0.928 mmol) in a mixture of triethylamine (1.293 ml, 0.939 g, 9.28 mmol) and DMF (5 ml). The reaction mixture was stirred overnight and diluted with ether. The obtained solid was collected by filtration, washed with ether, and dried in vacuo to afford the desired compound 2c (0.93 g, 0.80 mmol, 86%) as a pale solid. The crude material was used in the next step without further purification.

Synthesis of Compound 2d

Intermediate 2d was prepared in 90% yield by analogy with compound 2a starting from compound 1 and 2,2,2-trifluoro-N-methyl-N-[6-(methylamino)hexyl]-acetamide (Xu et al., 1995) and used in the next step without further purification.

Synthesis of Compound 3a

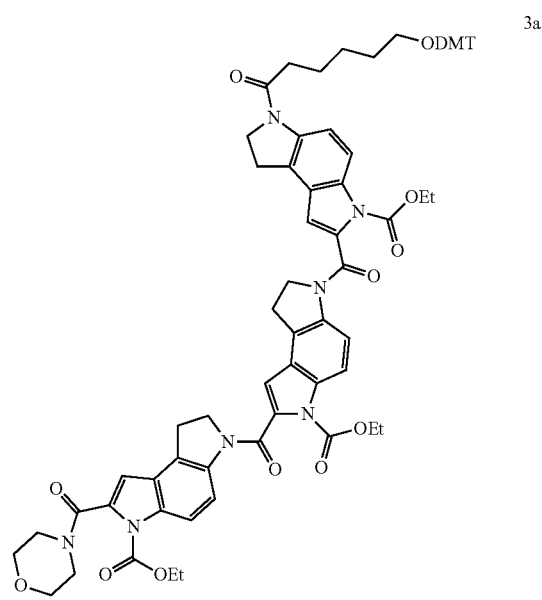

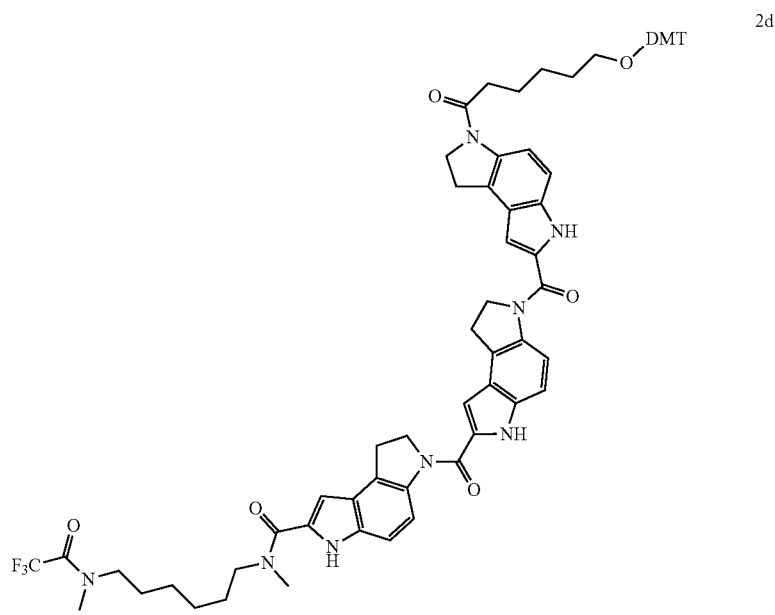

To a warm (50° C.) solution of compound 2a (1.20 g, 1.14 mmol), 4-N,N-dimethylaminopyridine (0.083 g, 0.68 mmol) and triethylamine (1.150 g, 11.36 mmol) in DMF (20 ml) was added with stirring diethyl pyrocarbonate (1.658 g, 10.23 mmol). After being stirred for 45 min the reaction was concentrated in vacuo, redissolved in dichloromethane and washed with 10% citric acid and saturated aqueous sodium chloride. The organic phase was separated, dried over $MgSO_4$ and concentrated in vacuo. The obtained material was chromatographed on silica eluting with a gradient of acetone (0-10%) in ethyl acetate to afford compound 3a (1.09 g, 0.89 mmol, yield=78%). $^1$H NMR (DMSO-d6): δ 8.31 (d, J=9.3 Hz, 1H), 8.28 (d, J=9.3 Hz, 1H), 8.28 (d, J=9.3 Hz, 1H), 8.05 (d, J=9.0 Hz, 1H), 8.00 (d, J=9.0 Hz, 1H), 7.93 (d, J=9.0 Hz, 1H), 7.40-7.18 (m, 9H), 7.07 (s, 1H), 7.03 (s, 1H), 6.87 (d, J=8.7 Hz, 4H), 6.86 (s, 1H), 4.45-4.00 (m, 12H), 3.72 (s, 6H), 3.70-3.50 (m, 6H), 3.40-3.22 (m, 8H), 2.97 (t, J=6.3 Hz, 2H), 2.45 (t, J=7.5 Hz, 2H), 1.65-1.60 (m, 4H), 1.45-1.34 (m, 5H), 1.09 (t, J=6.9 Hz, 6H).

Synthesis of Compound 3b

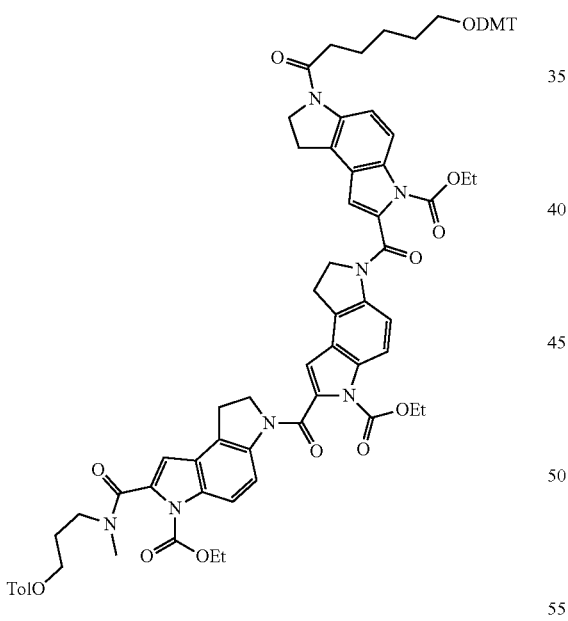

Compound 3b was prepared in 89% yield by analogy with compound 3a starting from compound 2b. $^1$H NMR (DMSO-d6): δ 8.34-8.16 (m, 3H), 8.04 (d, J=9.0 Hz, 1H), 7.90 (d, J=9.0, 1H), 7.93 (d, J=9.0 Hz, 1H), 7.90 (d, J=8.0 Hz, 1H), 7.85 (d, J=8.0 Hz, 1H), 7.42-7.18 (m, 10H), 7.08-6.96 (m, 3H), 6.88 (d, J=9.0 Hz, 4H), 6.77 (d, J=7.5 Hz, 1H), 4.45-4.00 (m, 14H), 3.72 (s, 6H), 3.70-2.90 (m, 13H), 2.46-2.25 (m, 5H), 2.05 (m, 2H), 1.65-1.50 (m, 4H), 1.50-1.25 (m, 5H), 1.25-1.00 (m, 6H).

Synthesis of Compound 3c
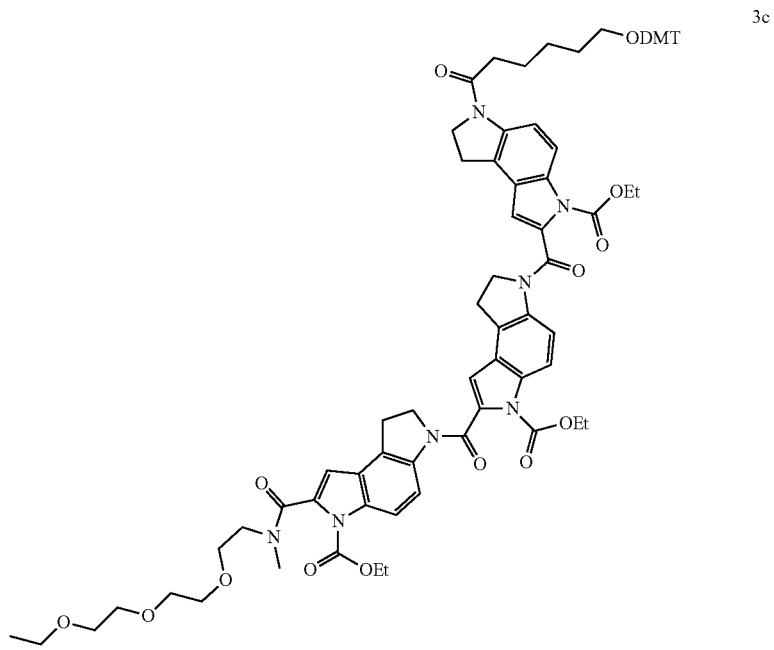
Compound 3c was prepared in 71% yield by analogy with compound 3a starting from compound 2c. $^1$H NMR (DMSO-d6): δ 8.34-8.24 (m, 3H), 8.05 (d, J=9.0 Hz, 1H), 8.0 (d, J=9.0, 1H), 7.93 (d, J=9.0 Hz, 1H), 7.40-7.18 (m, 9H), 7.07 (d, J=10.5 Hz, 1H), 7.07 (d, J=10.5 Hz, 1H), 6.87 (d, J=8.7 Hz, 4H), 6.82 (d, J=10.5 Hz, 1H), 4.45-4.00 (m, 12H), 3.72 (s, 6H), 3.70-3.20 (m, 20H), 3.05-2.90 (m, 5H), 2.46 (t, J=7.5 Hz, 2H), 1.65-1.50 (m, 4H), 1.50-1.25 (m, 5H), 1.25-1.00 (m, 9H).
Synthesis of Compound 3d
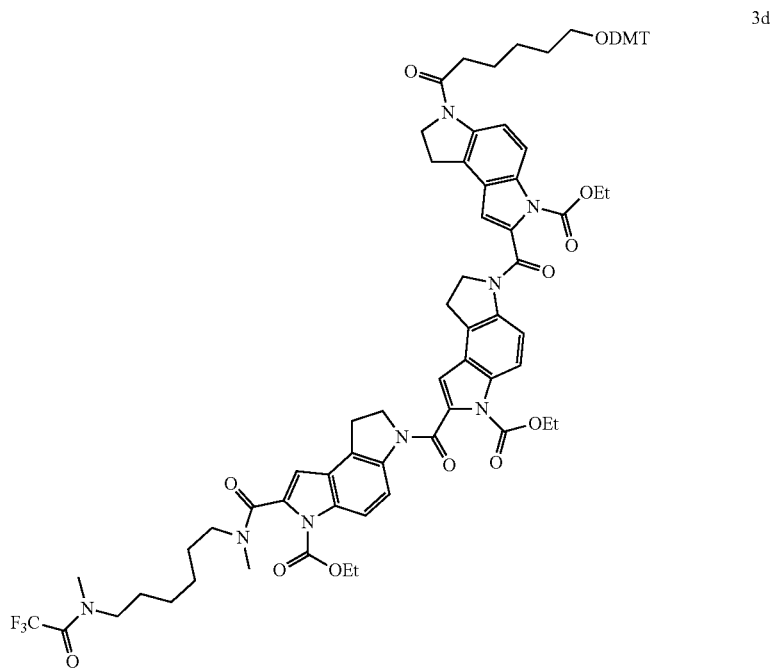

Compound 3d was prepared in 75% yield by analogy with compound 3a starting from compound 2d. $^1$H NMR (DMSO-d6): δ 8.31 (d, J=9.0 Hz, 1H), 8.28 (d, J=9.3 Hz, 1H), 8.27 (d, J=9.0 Hz, 1H), 8.04 (d, J=9.0 Hz, 1H), 7.99 (dd, J=9.3, 1.8 Hz, 1H), 7.93 (d, J=9.0 Hz, 1H), 7.40-7.18 (m, 9H), 7.07 (d, J=2.4 Hz, 1H), 7.04 (s, 1H), 6.85 (d, J=8.7 Hz, 4H), 6.81 (dd, J=2.4, 1.8 Hz, 1H), 4.45-4.00 (m, 12H), 3.72 (s, 6H), 3.50-3.20 (m, 10H), 3.15-2.85 (m, 8H), 2.45 (t, J=7.5 Hz, 2H), 1.65-1.05 (m, 23H).

was chromatographed on silica eluting with 3:2 acetone/dichloromethane to afford compound 4a (0.67 g, 0.69 mmol, 83% yield) as a light tan solid. $^1$H NMR (DMSO-d6): δ 8.36-8.23 (m, 3H), 8.05 (d, J=8.7 Hz, 1H), 7.99 (d, J=9.0 Hz, 1H), 7.93 (d, J=9.3 Hz, 1H), 7.08 (s, 1H), 7.04 (s, 1H), 6.87 (s, 1H), 4.45-4.00 (m, 12H), 3.70-3.50 (m, 6H), 3.45-3.22 (m, 10H), 2.47 (t, J=7.2 Hz, 2H), 1.65-1.55 (m, 2H), 1.50-1.30 (m, 7H), 1.09 (t. J=7.2 Hz, 6H).

Synthesis of Compound 4a

Synthesis of Compound 4b

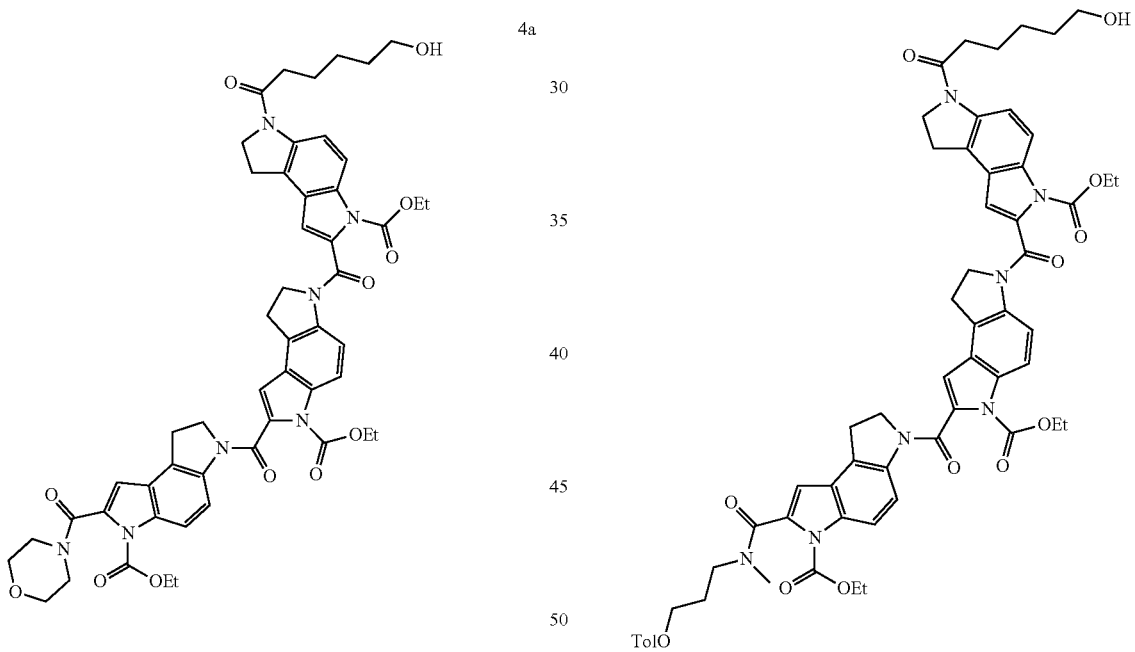

To a mixture of dichloromethane (20 ml), methanol (5 ml), and water (0.1 ml) was added compound 3a (1.05 g, 0.83 mmol) followed by trifluoracetic acid (0.305 g, 2.67 mmol). The reaction was allowed to run for 10 min, then quenched by addition of triethylamine (0.289 g, 2.86 mmol) and concentrated in vacuo. The residue was dissolved in dichloromethane (100 ml), washed with saturated NaCl, dried over MgSO$_4$, and concentrated in vacuo. The resultant material Compound 4b was prepared in 82% yield by analogy with compound 4a starting from compound 3b. $^1$H NMR (DMSO-d6): δ 8.35-8.16 (m, 3H), 8.10-7.8 (m, 4H), 7.40 (d, J=8.1 Hz, 1H), 7.35 (d, J=8.1 Hz, 1H), 7.09-6.93 (m, 3H), 6.77 (d, J=7.8 Hz, 1H), 4.45-3.95 (m, 14H), 3.65-2.90 (m, 13H), 2.49-2.25 (m, 5H), 2.05-1.95 (m, 2H), 1.70-1.55 (m, 2H), 1.55-1.20 (m, 7H), 1.20-1.00 (m, 6H).

Synthesis of Compound 4c
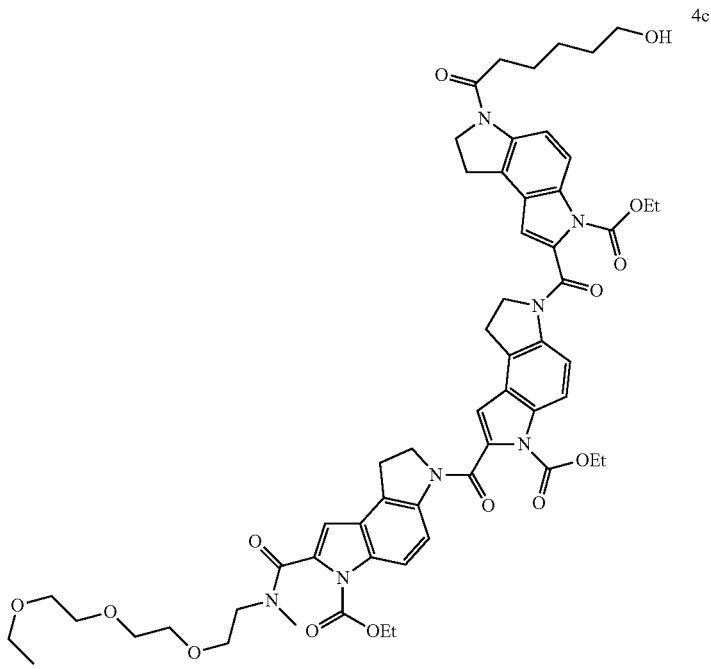 [SMILES: CCOCCOCCOCCN(C)C(=O)c1cc2c3c(ccc2n1C(=O)OCC)N(C(=O)c1cc2c4c(ccc2n1C(=O)OCC)N(C(=O)c1cc2c5c(ccc2n1C(=O)OCC)N(C(=O)CCCCCO)CC5)CC4)CC3]
Compound 4c was prepared in 100% yield by analogy with compound 4a starting from compound 3c. $^1$H NMR (DMSO-d6): δ 8.35-8.22 (m, 3H), 8.05 (d, J=9.0 Hz, 1H), 8.00 (d, J=9.0 Hz, 1H), 7.93 (d, J=9.0 Hz, 1H), 7.05 (d, J=10.5 Hz, 1H), 7.00 (m, 1H), 6.82 (d, J=10.5 Hz, 1H), 4.45-4.00 (m, 12H), 3.70-3.20 (m, 22H), 3.05-2.95 (m, 3H), 2.46 (t, J=7.5 Hz, 2H), 1.70-1.55 (m, 2H), 1.55-1.20 (m, 7H), 1.20-1.00 (m, 9H).
Synthesis of Compound 4d
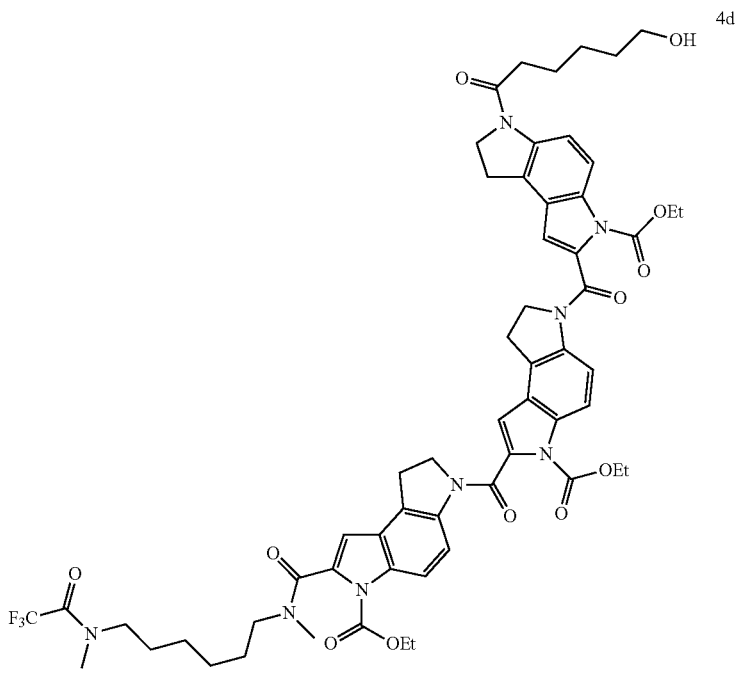 [SMILES: CCOC(=O)n1c(C(=O)N2CCc3c2ccc2c3cc(C(=O)N3CCc4c3ccc3c4cc(C(=O)N(C)CCCCCCN(C)C(=O)C(F)(F)F)n3C(=O)OCC)n2C(=O)OCC)cc2c3c(ccc21)N(C(=O)CCCCCO)CC3]

Compound 4d was prepared in 80% yield by analogy with compound 4a starting from compound 3d. $^1$H NMR (DMSO-d6): δ 8.36-8.20 (m, 3 FE), 8.04 (d, J=9.0 Hz, 1H), 8.00 (dd. J=8.8, 2.1 Hz, 1H), 7.93 (d, J=9.0 Hz, 1H), 7.07 (d, J=3.3 Hz, 1H), 7.04 (s, 1H), 6.81 (dd, J=2.1, 2.4 Hz, 1H), 4.45-4.05 (m, 12H), 3.50-3.20 (m, 10H), 3.15-2.85 (m, 8H), 2.46 (t. J=7.2 Hz, 2H), 1.65-1.05 (m, 23H)

Synthesis of Compound 5a

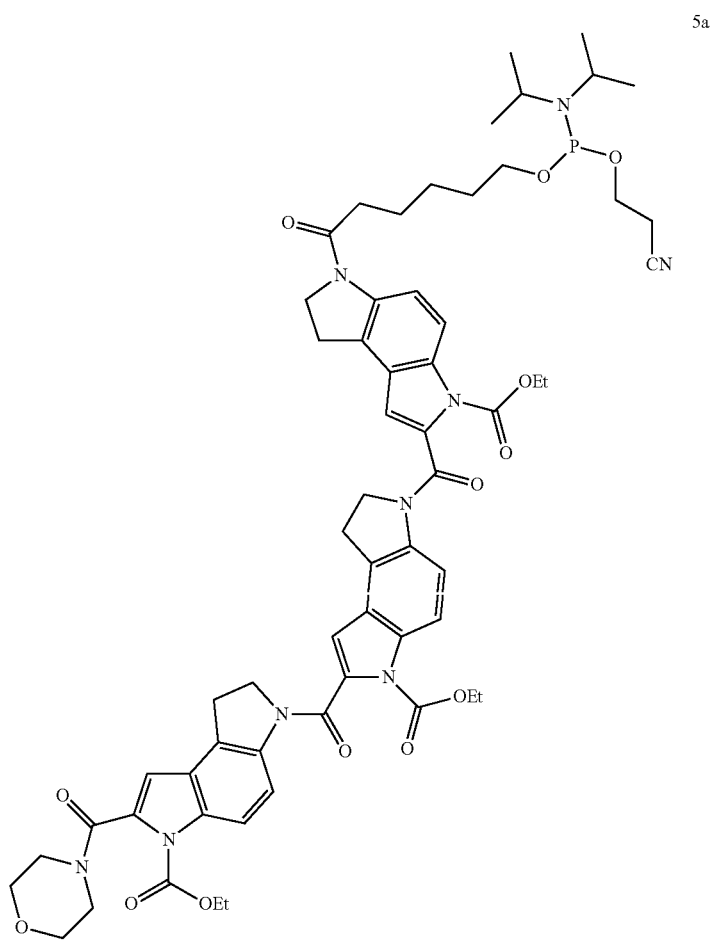 [SMILES: CCOC(=O)n1c(C(=O)N2CCc3c2ccc2c3cc(C(=O)N3CCc4c3ccc3c4cc(C(=O)N4CCOCC4)n3C(=O)OCC)n2C(=O)OCC)cc2c3c(ccc21)N(C(=O)CCCCCOP(OCCC#N)N(C(C)C)C(C)C)CC3]

Diisopropylammonium tetrazolide (0.100 g, 0.58 mmol) and 2-cyanoethyl N,N,N'N'-tetraisopropylphosphordiamidite (0.274 g, 0.91 mmol) were added to a solution of compound 4a (0.63 g, 0.65 mmol) in dichloromethane (10 ml). The resultant mixture was stirred under argon at room temperature for 1 h, and then diluted with saturated aqueous NaHCO$_3$. The organic phase was washed with saturated aqueous NaCl, dried over MgSO$_4$ and concentrated in vacuo. The residue was dissolved in a minimal amount of ethyl acetate and diluted with excess of ether. The solid material was collected by filtration, washed with ether and dried in vacuo to afford phosphoramidite 5a (0.67 g, 0.57 mmol, 88% yield) as a light tan solid. $^{31}$P NMR (CDCl$_3$): δ 146.90.

Synthesis of Compound 5b
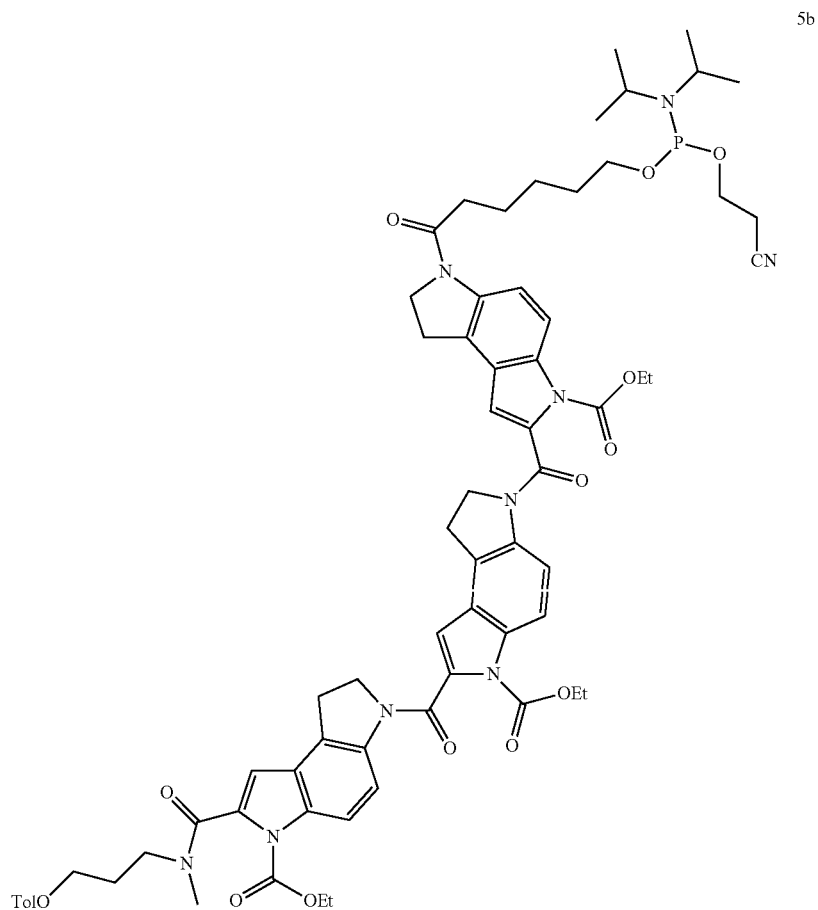
Phosphoramidite 5b was prepared in 91% yield by analogy with compound 5a starting from compound 4b. $^{31}$P NMR (CDCl$_3$): δ 147.22.

Synthesis of Compound 5c
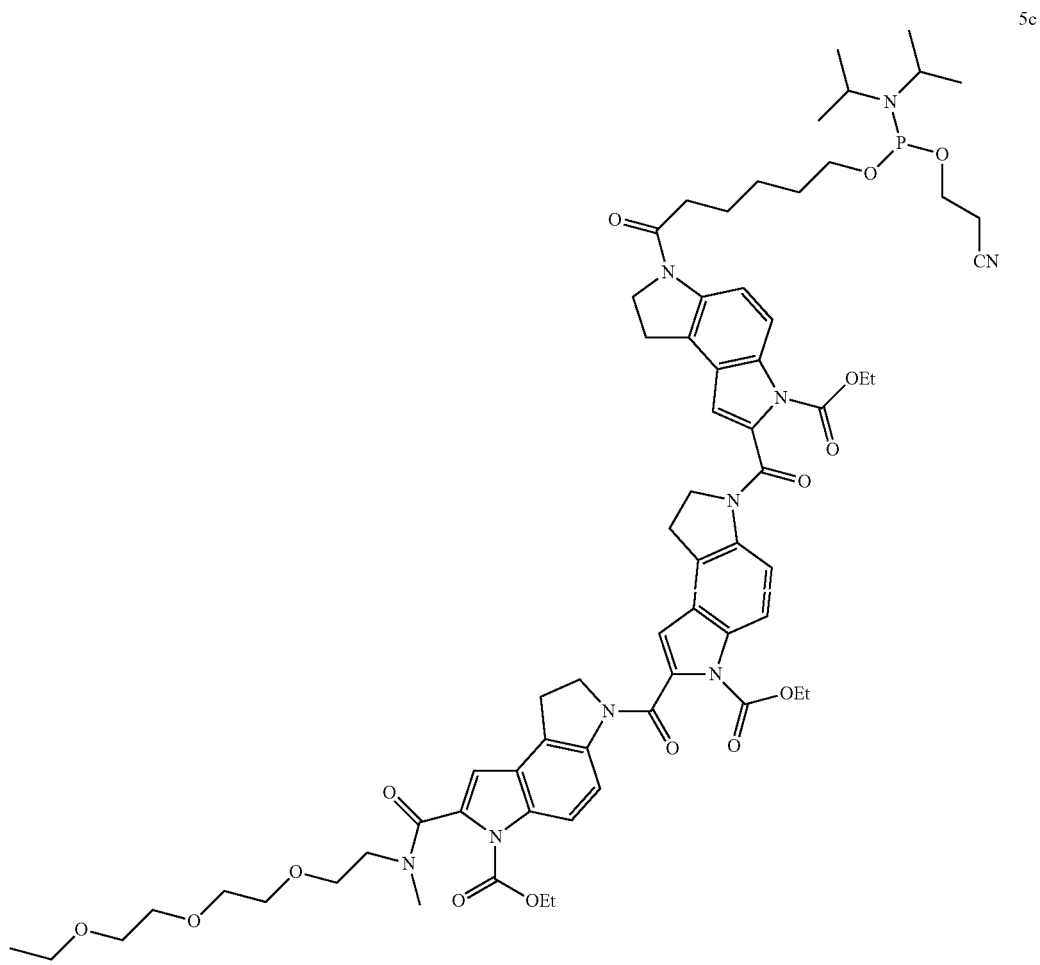 [SMILES: CCOCCOCCOCCN(C)C(=O)c1cc2c3c(ccc2n1C(=O)OCC)N(C(=O)c1cc2c4c(ccc2n1C(=O)OCC)N(C(=O)c1cc2c5c(ccc2n1C(=O)OCC)N(C(=O)CCCCCOP(OCCC#N)N(C(C)C)C(C)C)CC5)CC4)CC3]
Phosphoramidite 5c was prepared in 68% yield by analogy with compound 5a starting from compound 4c. $^{31}$P NMR (CDCl$_3$): δ147.23.

Synthesis of Compound 5d
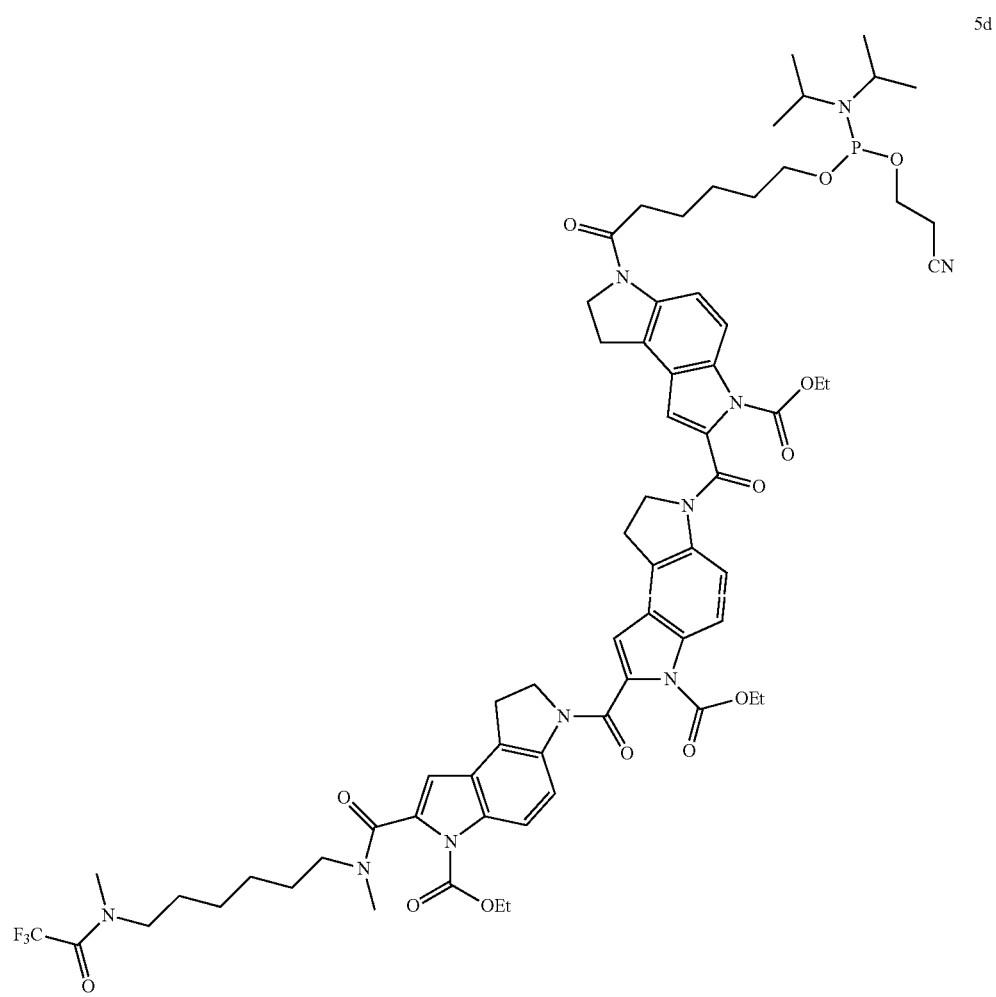 [SMILES: CCOC(=O)n1c(C(=O)N2CCc3c2ccc2c3cc(C(=O)N3CCc4c3ccc3c4cc(C(=O)N(C)CCCCCCN(C)C(=O)C(F)(F)F)n3C(=O)OCC)n2C(=O)OCC)cc2c3c(ccc21)N(C(=O)CCCCCOP(OCCC#N)N(C(C)C)C(C)C)CC3]
Phosphoramidite 5d was prepared in 69% yield by analogy with compound 5a starting from compound 4d. $^{31}$P NMR (CDCl$_3$): δ 147.23.
Example 3
This example illustrates the synthesis of minor groove binder phosphoramidites 12a,b.
Synthesis of Compound 8a
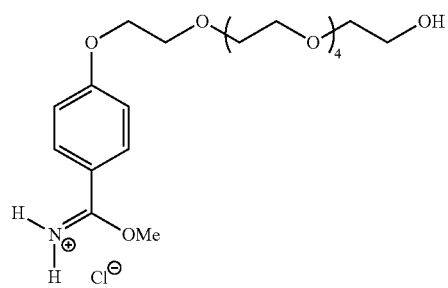
+
-continued
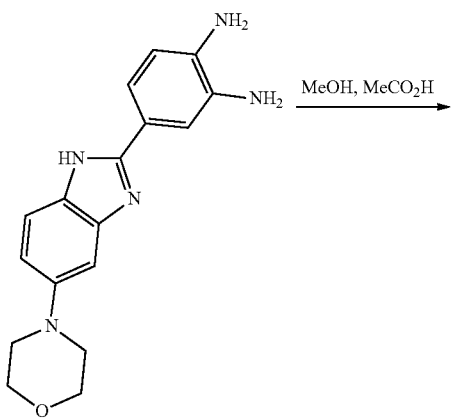

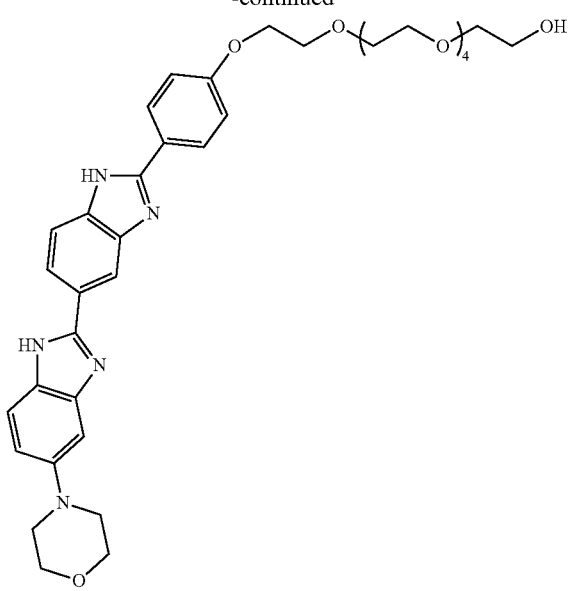

8a

To a solution of compounds 7a (PCT Int. Appl. (2011), WO 2011123890 A1.) (0.70 g, 2.26 mmol) and 6 (Hoechst 33258 Tethered by a Hexa(ethylene glycol) Linker) to the 5'-Termini of Oligodeoxynucleotide 15-Mers: Duplex Stabilization and Fluorescence Properties. Sharanabasava B. Rajur, Jordi Robles, Kristin Wiederholt, Robert G. Kuimelis, and Larry W. McLaughlin. J. Org. Chem., 1997, 62 (3), pp 523-529.) (1.81 g, 4.0 mmol) in anhydrous methanol (10 ml) was added acetic acid (0.240 g, 0.229 ml, 4.0 mmol). The reaction was refluxed with under argon for 6 h and then concentrated in vacuo. The obtained residue was chromatographed on silica eluting with 2% triethylamine, 5% methanol in dichloromethane to afford product 8a (1.55 g, 2.29 mmol, 101%) as a light yellow solid. The product contained some triethylammonium acetate as a small impurity according to $^1$H NMR. (DMSO-d6): δ 13.08 (s, 0.5H), 13.05 (s, 0.5H), 12.70 (br s, 0.5H), 12.62 (s, 0.5H), 10.0 (br s), 8.36 (s, 0.5H), 8.25 (s, 0.5H), 8.16 (dd, 2H), 8.03 (m, 1H), 7.72 (d, 0.5H), 7.61 (d, 0.5H), 7.48-7.41 (m, 1H), 7.14 (d, 2H), 6.94 (d, 2H), 4.61 (t, 1H), 4.20 (m, 2H), 3.78 (m, 6H), 3.58 (m, 4H), 3.52 (m, 14H), 3.58 (m, 3H), 3.10 (m, 4H).

Synthesis of Compound 9a

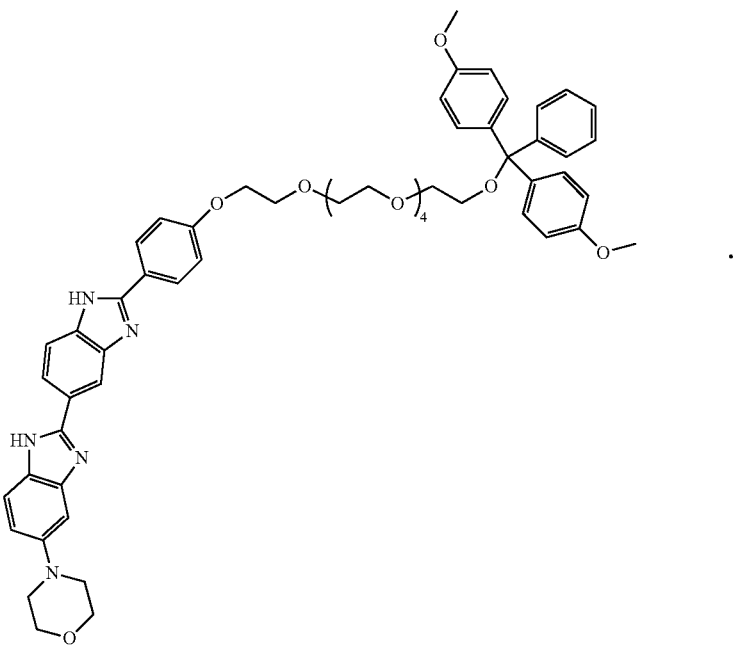

9a

To a solution of compound 8a (1.50 g, 2.20 mmol) in anhydrous pyridine (20 ml was added dimethoxytrityl chloride (0.79 g, 2.33 mmol). After being stirred for 2.5 h the reaction mixture was concentrated in vacuo, redissolved in dichloromethane, washed with 10% citric acid, saturated sodium bicarbonate, brine and dried over MgSO$_4$. The residue obtained after solvent evaporation was choromatographed on silica eluting with 7% methanol in dichloromethane to afford 1.19 g (55%) of the desired DMT derivative 9a as a light yellow amorphous solid. $^1$H NMR. (DMSO-d6): δ 12.95 (s, 1H), 12.61 (br s, 1H), 8.35 (s, 0.5H), 8.23 (s, 0.5H), 8.14 (d, 2H), 8.00 (dd, 1H), 7.72 (d, 0.5H), 7.60 (d, 0.5H), 7.39-7.35 (m, 3H), 7.35-7.12 (m, 10H), 6.94 (d, 2H), 6.86 (d, 4H), 4.18 (t, 2H), 3.77 (m, 6H), 3.72 (s, 6H), 3.62-3.48 (m, 19H), 3.11 (m, 4H), 3.03 (t, 2H).

Synthesis of Compound 9b
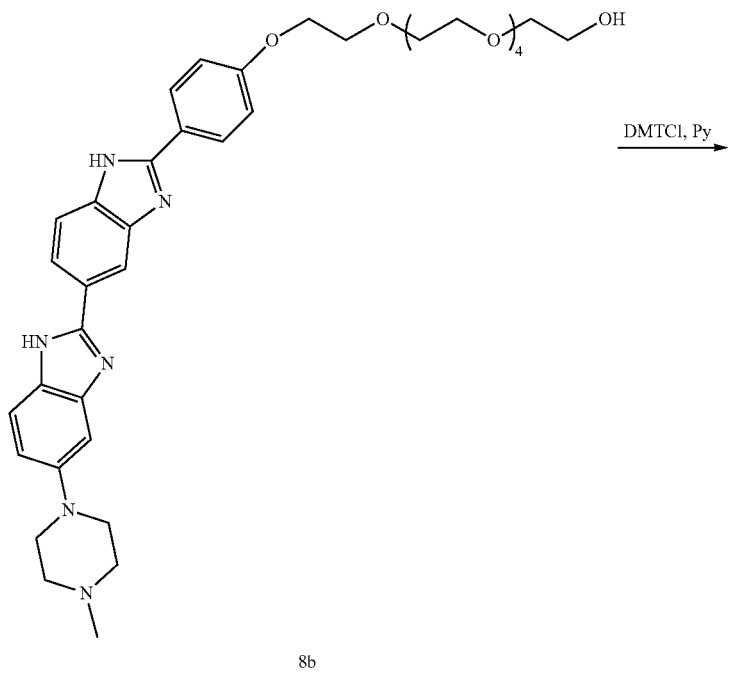
8b
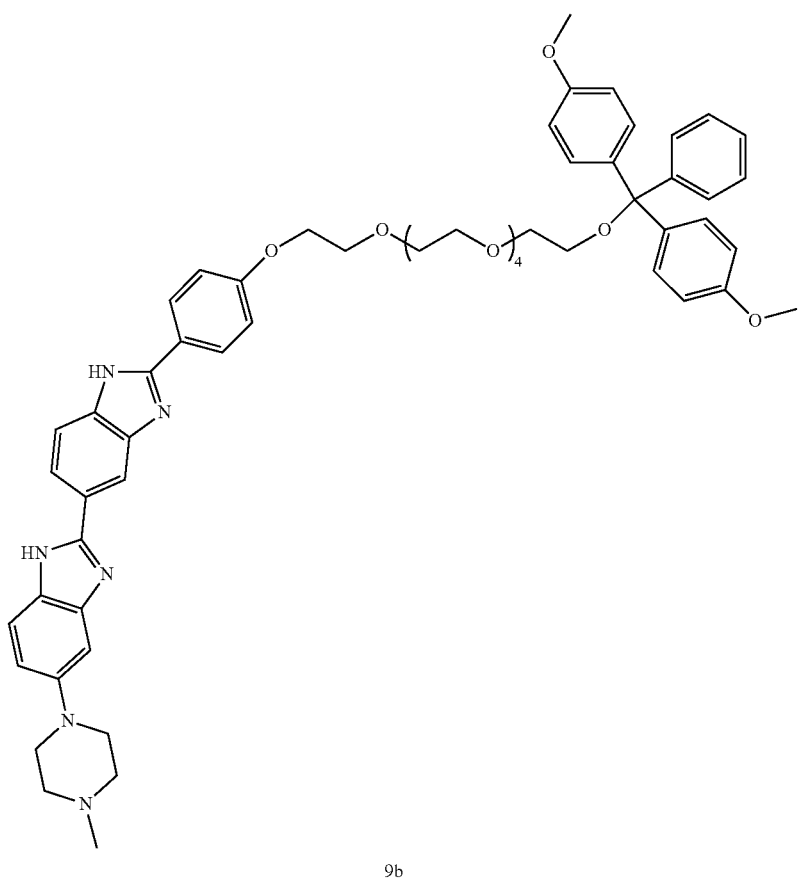
9b

To a suspension of compound 8b (Hoechst 33258 Tethered by a Hexa(ethylene glycol) Linker to the 5'-Termini of Oligodeoxynucleotide 15-Mers: Duplex Stabilization and Fluorescence Properties. Sharanabasava B. Rajur, Jordi Robles, Kristin Wiederholt, Robert G. Kuimelis, and Larry W. McLaughlin. J. Org. Chem., 1997, 62 (3), pp 523-529.) (2.30 g, 3.34 mmol) in anhydrous pyridine (30 ml) was added dimethoxytrityl chloride (1.188 g, 3.506 mmol) and the resultant solution was stirred overnight. Additional dimethoxytrityl chloride (0.3 eq.) was added to complete the reaction, which was then treated with triethylamine and concentrated in vacuo. The obtained residue was chromatographed on silica euting with 5% triethylamine, 10% methanol in dichloromethane to afford crude product 2 as a light brown amorphous solid, which still contained some triethylammonium salts. To remove the salts the crude product was dissolved in dichloromethane, washed with saturated sodium bicarbonate (slow phase separation) and dried with anhydrous MgSO$_4$. The drying agent was filtered off, washed with dichloromethane and DMF and the combined filtrates were concentrated in vacuo to give an oily residue, which was then triturated in ether. Decantation of ether and drying in vacuo afforded 3.21 g (97%) of compound 9b as a yellow solid. $^1$H NMR. (DMSO-d6): δ 12.95 (s, 1H), 12.6 (m, 1H), 8.38 (d, 0.5H), 8.25 (d, 0.5H), 8.14 (d, 2H), 8.00 (m, 1H), 7.71 (d, 0.5H), 7.60 (d, 0.5H), 7.5-7.1 (m, 12H), 7.0-6.8 (m, 6H), 4.18 (t, 2H), 3.76 (m, 2H), 3.72 (s, 6H), 3.6-3.5 (m, 19H), 3.12 (m, 4H), 3.03 (t, 2H).

Synthesis of Compound 10a

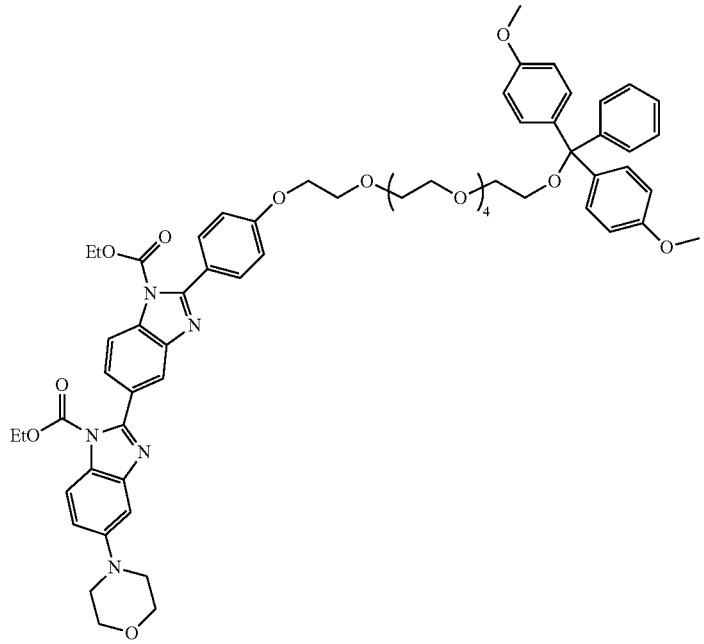

10a

To a stirred solution of compound 9a (1.07 g, 1.09 mmol) 4-N,N,-dimethylaminopyridine (0.053 g, 0.44 mmol) and triethylamine (0.996 g, 1.372 ml, 9.85 mmol)) in 5 ml of anhydrous DMF at 50° C. was added in one portion 1.064 g (6.56 mmol) of diethyl pyrocarbonate Two more portions of each diethyl pyrocarbonate (2.0 eq) and triethylamine (3.0 eq) were added in 0.5 hour intervals to complete the reaction. The reaction was concentrated, diluted with dichloromethane, washed with 10% citric acid, saturated sodium bicarbonate, dried over MgSO$_4$ and concentrated in vacuo. The crude product was chromatographed on silica eluting with 3% methanol in dichloromethane to afford 1.20 g (98%) of fully blocked intermediate 10a as a yellow viscous oil. $^1$H NMR. (DMSO-d6): δ 8.31 (d, 0.25H), 8.27 (d, 0.25H), 8.06 (m, 1H), 7.87 (s, 0.25H), 7.84 (s, 0.25H), 7.82-7.68 (m, 3H), 7.65 (d, 0.25H), 7.62 (d, 0.25H), 7.51 (t, 0.5H), 7.42-7.36 (m, 2H), 7.35-7.10 (m, 9H), 6.87 (d, 4H), 4.37 (m, 4H), 4.17 (t, 2H), 3.80 (m, 6H), 3.72 (s, 6H), 3.6-3.5 (m, 18H), 3.16 (m, 4H), 3.04 (t, 2H), 1.19 (m, 6H).

Synthesis of Compound 10b

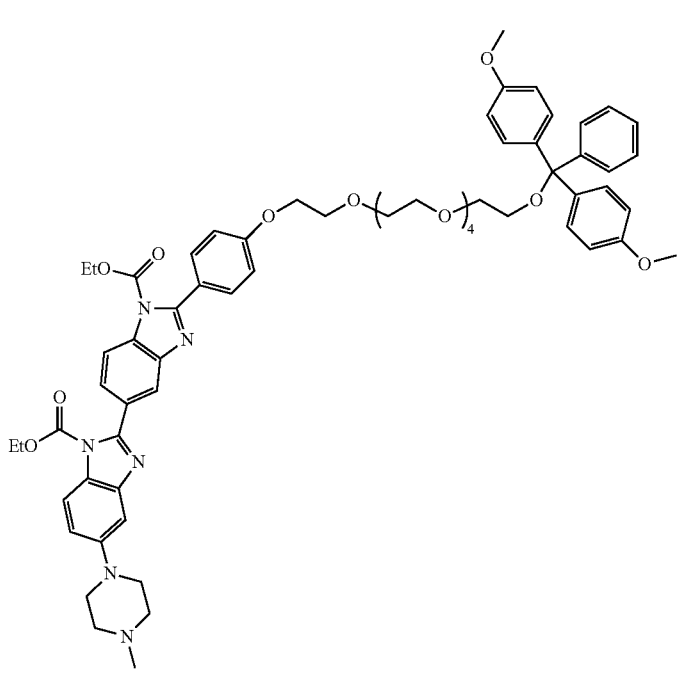

To a stirred solution of compound 9b (1.0 g, 1.0 mmol) 4-N,N,-dimethylaminopyridine (0.049 g, 0.44 mmol) and triethylamine (0.613 g, 6.05 mmol) in 5 ml of anhydrous DMF at 50° C. was added in one portion 0.654 g (4.04 mmol) of diethyl pyrocarbonate. After having been stirred for 45 min three more portions of each diethyl pyrocarbonate (1.0 eq) and triethylamine (2.0 eq) were added in 0.5 hour intervals to complete the reaction. The reaction was concentrated in vacuo, diluted with dichloromethane, washed with saturated sodium bicarbonate, saturated aqueous sodium chloride and dried over MgSO$_4$. The crude product obtained after solvent evaporation was chromatographed on silica eluting with 7% ethyl acetate, 5% triethylamine in dichloromethane. The product was a mixture of isomers and eluted in several fractions. All product-containing fractions were pooled and concentrated to afford 0.66 g (58%) of compound 10b as a light yellow-green amorphous solid. $^1$H NMR. (DMSO-d6): δ 8.27 (m, 0.5H), 8.04 (m, 1H), 7.80-(s, 0.25H), 7.77 (s, 0.25H), 7.76-7.68 (m, 3H), 7.63 (d, 0.5H), 7.60 (d, 0.5H), 7.50 (m, 1H), 7.42-7.36 (m, 2H), 7.34-7.18 (m, 7H), 7.15 (t, 0.5H), 7.11 (t, 0.5H), 7.08-7.01 (m, 2H), 6.86 (d, 4H), 4.37 (m, 4H), 4.17 (t, 2H), 3.76 (m, 2H), 3.72 (s, 6H), 3.60-3.0 (m, 4H), 3.20 (m, 4H), 3.04 (t, 2H), 1.18 (m, 6H).

Synthesis of Compound 11a

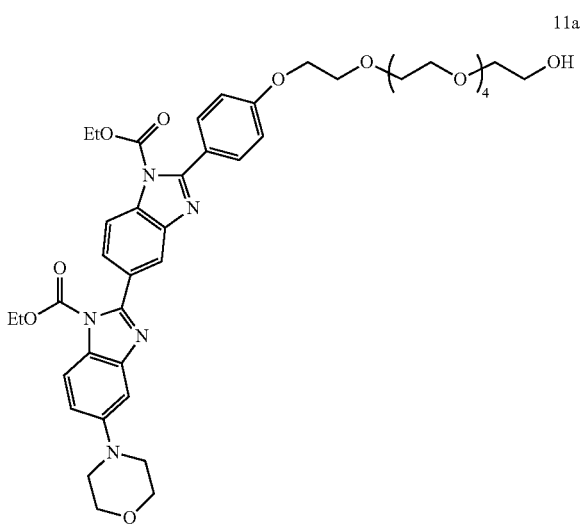

Trifluoroacetic acid (0.232 ml, 0.356 g, 3.12 mmol) was added to a solution of compound 10a (1.08 g, 0.96 mmol) in mixture of dichloromethane (12 ml), methanol (3 ml), and water (0.06 ml). The reaction was allowed to run for 45 min and then quenched by addition of triethylamine (0.463 ml, 0.337 g, 3.33 mmol). Dichloromethane was removed by evaporation in vacuo and the residue re-dissolved in 75 ml of dichloromethane. After having been washed with saturated sodium bicarbonate, and dried over MgSO$_4$, the solution was concentrated and the residue chromatographed on silica eluting with 8% methanol in dichloromethane to afford compound 11a as a mixture of isomers (0.71 g, 90%, light yellow viscous oil: $^1$H NMR. (DMSO-d6): δ 8.30 (d, 0.25H), 8.27 (d, 0.25H), 8.08-8.02 (m, 1H), 7.87 (s, 0.25H), 7.84 (s, 0.25H), 7.82-6.68 (m, 3H), 7.64 (d, 0.25H), 7.63 (d, 0.25H), 7.51 (t, 0.5H), 7.27 (t, 0.5H), 7.20-7.10 (m, 1H), 7.10-7.00 (m, 2H), 4.52 (m, 1H), 4.36 (m, 4H), 4.20 (m, 2H), 3.78 (m, 6H), 3.65-3.45 (m, 18H), 3.38 (m, 2H), 3.16 (m, 4H), 1.19 (m, 6H).

Synthesis of Compound 11b

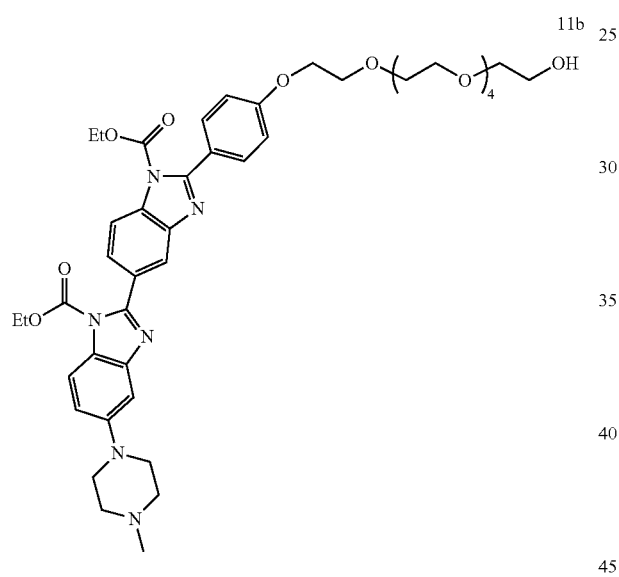

Trifluoroacetic acid (0.134 ml, 0.205 g, 1.80 mmol) was added to a solution of compound 10b (0.63 g, 0.56 mmol) in mixture of dichloromethane (8), methanol (2 ml), and water (0.04 ml). The reaction was allowed to run for 45 min and then quenched by addition of triethylamine (0.267 ml, 0.194 g, 1.92 mmol). Dichloromethane was removed by evaporation in vacuo and the residue re-dissolved in 50 ml of dichloromethane. After having been washed with saturated sodium bicarbonate, and dried over MgSO$_4$, the solution was concentrated and the residue chromatographed on silica eluting with 5% triethylamine, 2% methanol in dichloromethane to afford compound 11b as a mixture of isomers (0.42 g, 90%, light yellow viscous oil. $^1$H NMR. (DMSO-d6): δ 8.30 (d, 0.25H), 8.27 (d, 0.25H), 8.08-8.02 (m, 1H), 7.86-7.65 (m, 3.5H), 7.62 (d, 0.25H), 7.60 (d, 0.25H), 7.50 (t, 0.5H), 7.25 (t, 0.25H), 7.18-7.10 (m, 1H), 7.10-7.04 (m, 2H), 4.57 (t, 1H), 4.36 (m, 4H), 4.19 (m, 2H), 3.79 (m, 2H), 3.65-3.45 (m, 18H), 3.45-3.30 (m, 5H), 3.19 (m, 4H), 1.19 (m, 6H).

Synthesis of Compound 12a

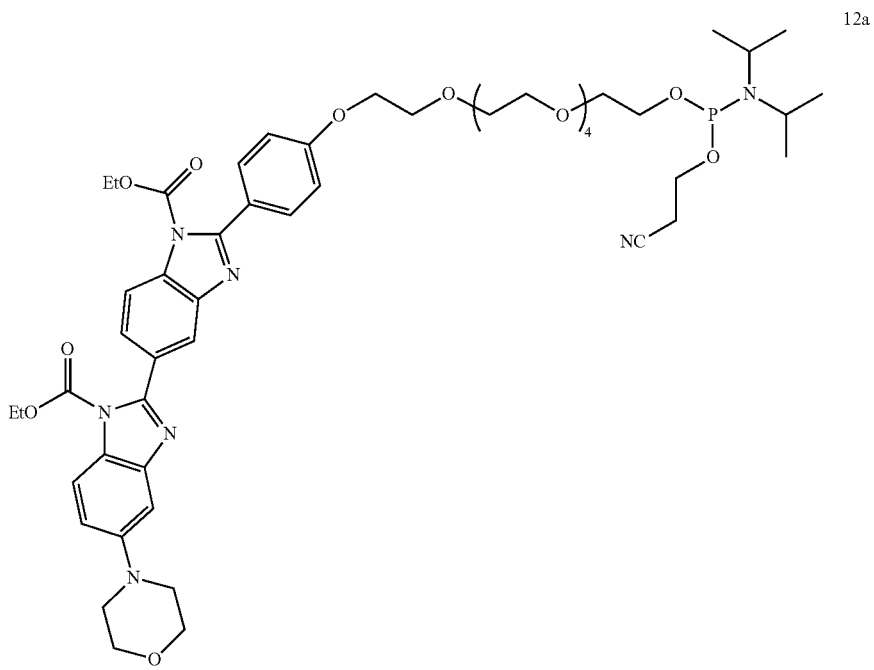

To a solution of compound 11a (0.62 g, 0.86 mmol) in anhydrous dichloromethane (10 ml) was added diisopropylammonium tetrazolide (0.133 g, 0.78 mmol) followed by 2-cyanoethyl N,N,N'N'-tetraisopropylphosphordiamidite (0.299 g, 0.315 ml, 0.99 mmol). The reaction mixture was stirred under argon at room temperature for 2.5 h and then diluted with dichloromethane and saturated sodium bicarbonate. The organic phase was separated, dried over MgSO$_4$ and concentrated in vacuo. The resulting material was chromatographed on silica eluting with 5% ethyl acetate, 3% triethylamine in dichloromethane to give the desired phosphoramidite 12a (0.67 g, 76%) as a yellow-green viscous oil. $^{31}$P NMR. (CDCl$_3$): δ 148.4.

Synthesis of Compound 12b

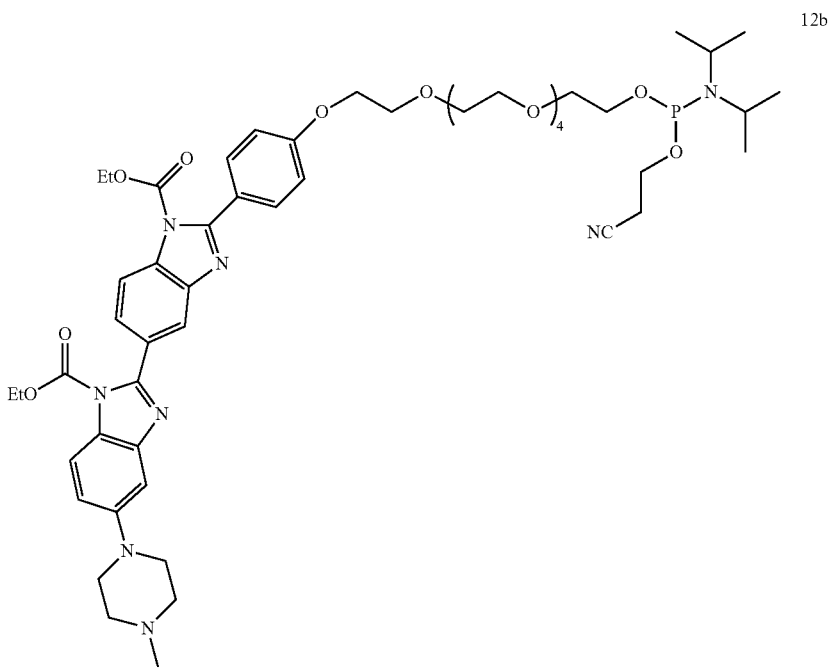

To a solution of compound 11b (0.40 g, 0.48 mmol) in anhydrous dichloromethane (10 ml) was added diisopropylammonium tetrazolide (0.074 g, 0.43 mmol) followed by 2-cyanoethyl N,N,N'N'-tetraisopropylphosphordiamidite (0.261 g, 0.275 ml, 0.86 mmol). The reaction mixture was stirred under argon at room temperature for 2.5 h and then diluted with dichloromethane and saturated sodium bicarbonate. The organic phase was separated, dried over $MgSO_4$ and concentrated in vacuo. The resulting material was chromatographed on silica eluting with 20% acetone, 5% triethylamine in dichloromethane to give the desired phosphoramidite 12b (0.43 g, 87%) as a yellow-green viscous oil. $^{31}P$ NMR. ($CDCl_3$): δ 148.4.

Example 4

This example illustrates the synthesis of minor groove binder PFP ester 18.

Synthesis of Compound 13

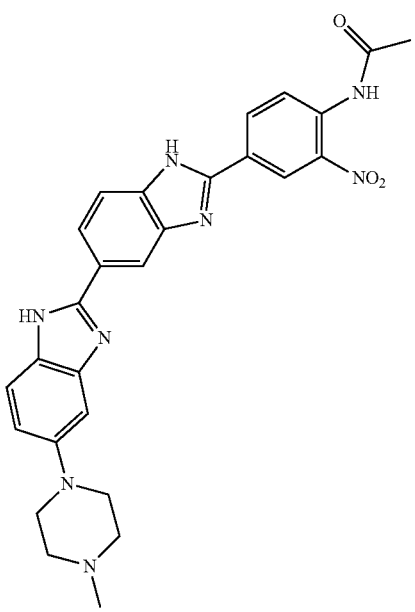

A solution of diamine 7b (3.39 g, 10.5 mmol) and N-(4-formyl-2-nitrophenyl)acetamide (2.19 g, 10.5 mmol) in DMF (70 ml) solution was stirred for 1 h at 90° C. A solution of anhydrous $FeCl_3$ (17 mg, 0.11 mmol) in DMF (5 ml) was added and the reaction was stirred for 23 h at 90° C. with a continuous light air flow over stirred mixture. The reaction mixture was cooled to room temperature and concentrated in vacuo. Residue was diluted with acetonitrile, triturated and refluxed for 0.5 h. Solid material was collected by filtration, washed with acetonitrile (3×20 ml) and dried in vacuo to afford crude product 13 (3.93 g, purity 77% by C18 HPLC) as dark brown solid. Resultant solid was refluxed one more time for 0.5 h in acetonitrile (150 ml), filtered and dried to give 3.40 g of more pure (81% by C18 HPLC) as a dark brown solid.

Synthesis of Compound 14

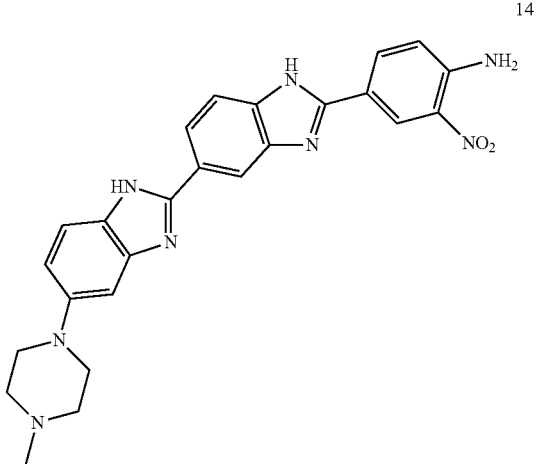 [SMILES: CN1CCN(c2ccc3[nH]c(-c4ccc5[nH]c(-c6ccc(N)c([N+](=O)[O-])c6)nc5c4)nc3c2)CC1]

A suspension of compound 13 (3.30 g, 6.46 mmol) and sodium hydroxide (0.323 g, 8.08 mmol) in a mixture of methanol (83 mL) and water (21 mL) was stirred at 70° C. for 4 h. The reaction mixture was cooled to room temperature and concentrated in vacuo to a solid, which was dried by co-evaporation with acetonitrile, and then chromatographed on silica eluting with 5% triethylamine, 20% methanol in dichloromethane to afford 2.15 g (71%) of compound 14 as an orange solid. $^1H$ NMR (DMSO-d6): δ 13.1 (br s, 1H), 12.58 (br s, 1H), 8.87 (s, 1H), 8.27 (m, 2H), 8.00 (m, 1H), 7.86 (s, 2H), 7.8-7.5 (m, 1H), 7.5-7.3 (m, 1H), 7.2-7.0 (m, 2H), 6.92 (m, 2H), 3.12 (br s, 4H), 2.24 (s, 3H).

Synthesis of Compound 15

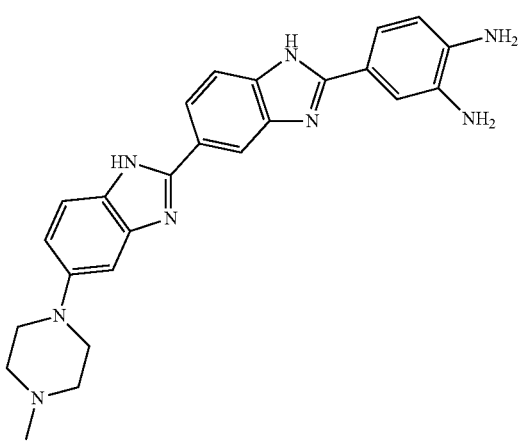

Compound 14 (0.20 g, 0.43 mmol) was hydrogenated at 50 psi overnight in methanol (50 ml) in the presence of 10% Pd/C (0.050 g). The catalyst was filtered off through a fiber-glass filter, washed with methanol and concentrated in vacuo to afford 0.180 g (96%) of the desired diamine 15 as a light brown solid. $^1H$ NMR (DMSO-d6): δ 12.55 (br s, 1H), 8.24 (br s, 0.5H), 8.13 (br s, 0.5H), 7.92 (m, 1H), 7.6-7.0 (m, 6.91 (br s, 2H), 6.60 (d, 1H), 3.12 (br s, 4H), 2.42 (s, 3H).

Synthesis of Compound 16

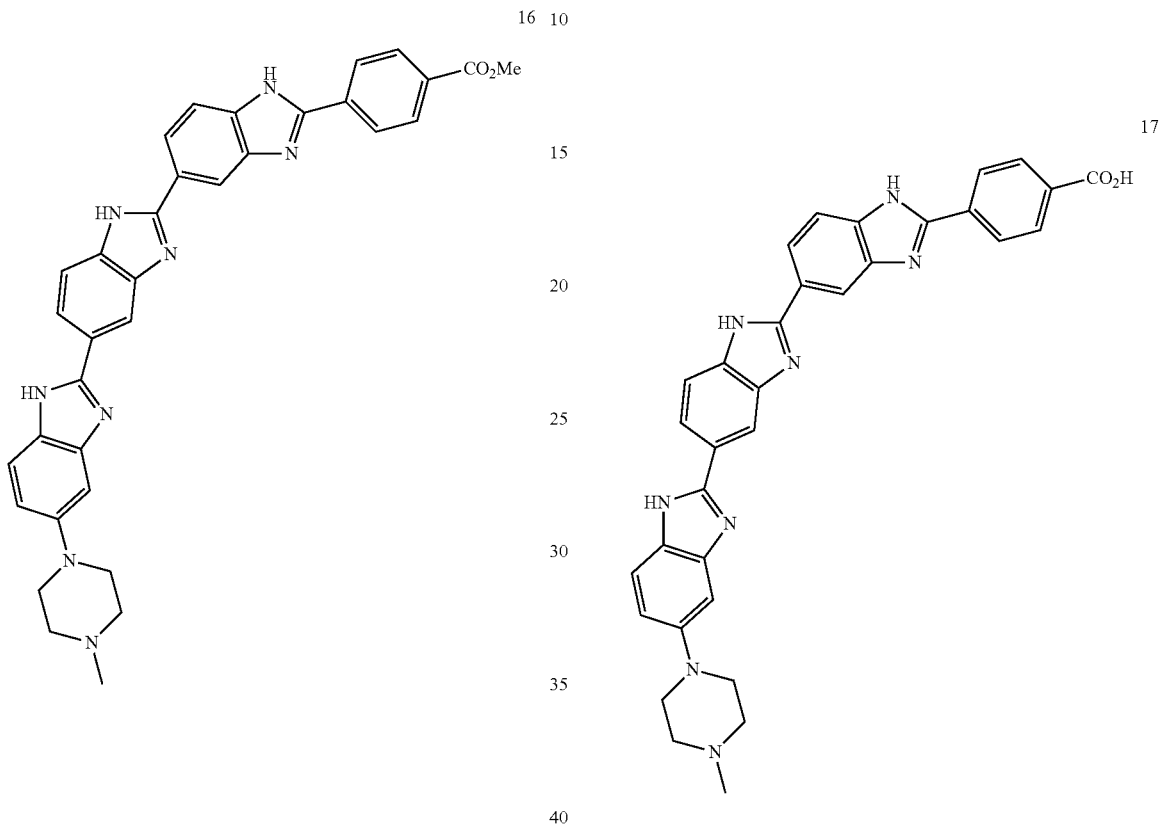

A solution of diamine 15 (0.168 g, 0.383 mmol) and methyl 4-formylbenzoate (0.063 g, 0.383 mmol) in DMF (3 mL) was stirred for 1 h at +90° C. and then concentrated in vacuo. Residue was dissolved in dichloromethane (3 ml) and transferred into 3-neck flask. A solution of anhydrous $FeCl_3$ (1 mg, 0.004 mmol) in DMF (0.1 ml) was added and the resultant mixture was heated for 20 h at 90° C. with continuous light flow of air over the stirred mixture. The reaction was cooled to room temperature and concentrated in vacuo. The obtained residue was diluted with acetonitrile and sonicated for 10 min which generated solid which was collected by filtration and washed with acetonitrile (3×5 ml). Drying in vacuo afforded 0.190 g (85%) of tri-benzimidazole 16 as a dark brown solid. $^1$H NMR (DMSO-d6): δ 13.44 (br s, 1H), 13.2-13.0 (br d, 1H), 13.61 (m, 1H), 8.8-7.0 (m, 12H), 6.93 (br s, 1H), 3.89 (s, 3H), 3.14 (br s, 4H), 2.56 (s, 3H).

Synthesis of Compound 17

A suspension of compound 16 (0.160 g, 0.28 mmol) and sodium hydroxide (0.014 g, 0.343 mmol) in a mixture of methanol (4 mL) and water (1 mL) was stirred at 70° C. for 4.5 h. The reaction was cooled to room temperature and concentrated in vacuo to give a solid material, which was dried by co-evaporation with acetonitrile and then chromatographed on silica eluting with 5% triethylamine, 5% methanol in ethanol. Concentration of the product-containing fractions and drying in vacuo afforded 0.074 g (47%) of the desired acid 17 as a yellow solid. $^1$H NMR (DMSO-d6): δ 13.40 (br s, 1H), 13.2-13.0 (br d, 1H), 12.61 (m, 1H), 8.6-7.0 (m, 12H), 6.93 (d, 2H), 3.17 (br s, 4H), 2.36 (br s, 3H).

Synthesis of Compound 18

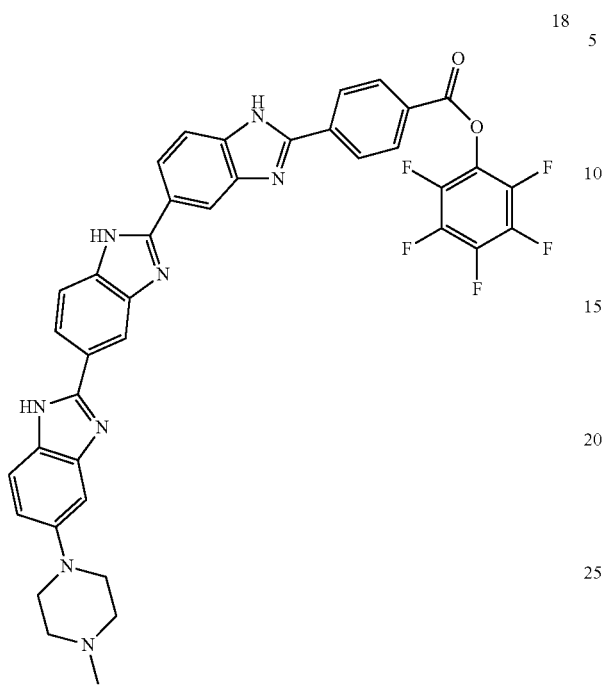

To a solution of compound 17 (0.065 g, 0.11 mmol) and triethylamine (0.0.035 g, 0.048 ml, 0.34 mmol) in DMF (2 ml) was added pentafluorophenyl trifluoroacetate (0.048 g, 0.029 ml, 0.17 mmol). After being stirred for 30 min the reaction was treated with two more portions of triethylamine and pentafluorophenyltrifluoroacetate (1 eq. each) with 1 h intervals then DMF was removed in vacuo and the residue triturated in ether. The resulting solid was collected by filtration, washed with ether and dried in vacuo to afford 0.10 g (120%) as a yellow solid. This material contained some salts but otherwise was suitable for subsequent reactions with amine-containing substrates.

Example 5

This example illustrates the synthesis of minor groove binder phosphoramidite 25.

Synthesis of Compound 20

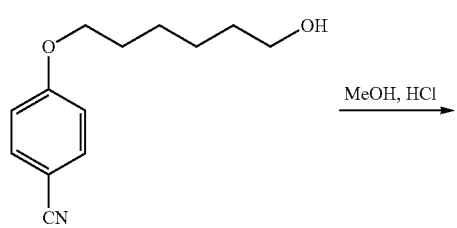

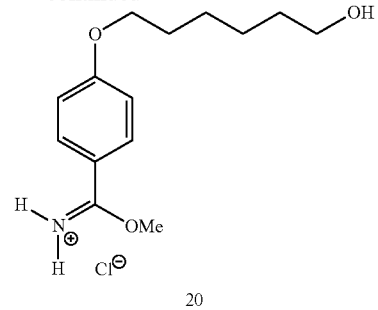

Hydrogen chloride gas was slowly bubbled through a cold (ice/water bath) solution of compound 19 (Fixed or Invertible Calixarene-Based Directional Shuttles. Teresa Pierro, Carmine Gaeta, Carmen Talotta, Agostino Casapullo, and Placido Neri Org. Lett. 2011, 13(10), 2650-2653.) (3.0 g, 13.68 mmol) and methanol (1.32 g, 41 mmol) in ether (100 ml) for 3 hrs. A second portion of methanol (6 eq) was added and resultant solution was kept at 4° C. for 2 days. Argon was bubbled through the solution to remove excess hydrogen chloride, and the precipitated solid was collected by filtration. Washing with ether (2×15 ml) and drying in vacuo afforded 2.86 (73%) of compound 20 as a white solid. $^1$H NMR (DMSO-d6): δ 8.12 (d, 2H), 7.16 (d, 2H), 4.37 (br s, 2H), 4.26 (s, 3H), 4.10 (t, 2H), 3.85 (t, 2H), 1.73 (m, 2H), 1.40 (m, 6H).

Synthesis of Compound 21

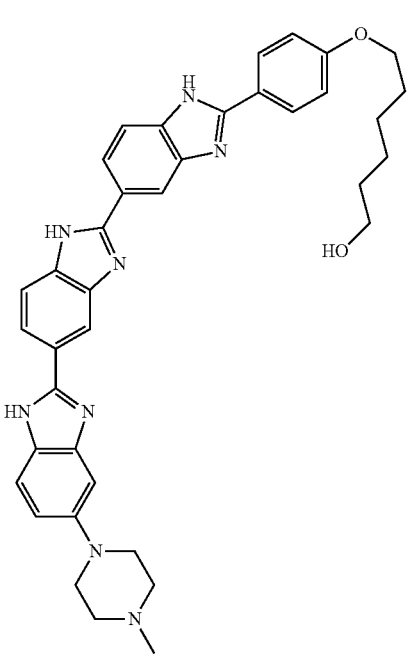

To a solution of compound 20 (1.951 g, 6.78 mmol) in anhydrous methanol (20 ml) was added 1.68 g (3.83 mmol) of compound 15 followed by acetic acid (0.407 g, 0.388 ml, 6.78 mmol). The resultant solution was refluxed with stirring at 70° C. under argon for 8 h, then overnight room temperature and was concentrated in vacuo. The obtained solid was triturated with aqueous triethylamine, collected by filtration, washed with water and dried in vacuo. An additional washing with ether and drying in vacuo afforded 2.41 g (98%) of compound 21 as a brown solid.

Synthesis of Compound 22

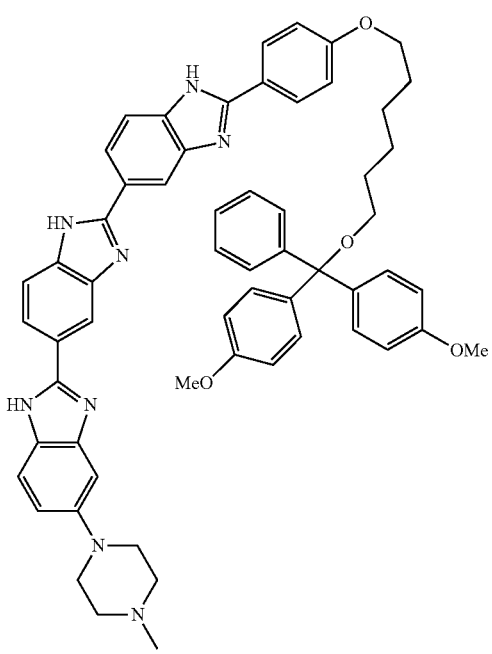

Dimethoxytrityl chloride (1.333 g, 3.933 mmol) was added to a solution of compound 21 (2.40 g, 3.745 mmol) in a mixture of triethylammine (1.5 ml), anhydrous DMF (20 ml) and anhydrous pyridine (30 ml). After being stirred for 1 h another portion of dimethoxytrityl chloride (3.7 mmol) was added followed by three more portions over 3 days to complete tritylation. The reaction was concentrated, diluted with dichloromethane, washed with 10% citric acid, then with saturated sodium bicarbonate (slow phase separation) and dried over $Na_2SO_4$. The drying agent was filtered off, washed with dichloromethane. Concentration of the filtrates and trituration in methanol produced a solid, which was then collected by filtration, washed with methanol and dried in vacuo to afford 2.61 g (74%) of compound 22 as a greenish-brown solid. $^1$H NMR (DMSO-d6): δ 13.03 (br s, 1H), 8.45-8.30 (m, 2H), 8.20-8.00 (m, 4H), 7.72 (m, 2H), 7.60-6.90 (m, 13H), 6.87 (m, 4H), 4.06 (t, 2H), 3.72 (s, 6H), 3.65-2.50 (m, 10H), 1.73 (m, 2H), 1.58 (m, 2H), 1.40 (m, 2H).

Synthesis of Compound 23

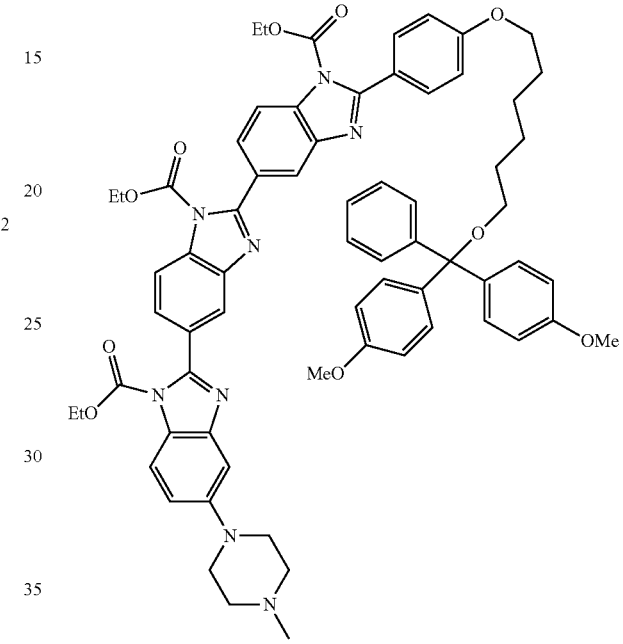

To a stirred solution of compound 22 (1.0 g, 1.06 mmol) 4-N,N,-dimethylaminopyridine (0.052 g, 0.424 mmol) and triethylamine (0.644 g, 6.36 mmol)) in 5 ml of anhydrous DMF at 50° C. was added in one portion 0.688 g (4.24 mmol) of diethyl pyrocarbonate. After having been stirred for 10 min 12 more portions of each diethyl pyrocarbonate (2.0 eq) and triethylamine (3.0 eq) were added in 0.5 hour intervals to complete the reaction. The reaction was concentrated in vacuo, diluted with dichloromethane, washed with saturated sodium bicarbonate, saturated aqueous sodium chloride and dried over $MgSO_4$. The crude product obtained after solvent evaporation was chromatographed on silica eluting with 10% ethyl acetate, 5% triethylamine in dichloromethane. The product was a mixture of isomers and eluted in several fractions. All product-containing fractions were pooled and concentrated to afford 0.65 g (53%) of compound 23 as a brown semi-solid. $^1$H NMR (DMSO-d6): δ 8.4-8.3 (m, 1H), 8.2-8.05 (m, 2H), 7.90-7.68 (m, 5H), 7.65-7.45 (m, 1H), 7.40-7.10 (m, 11H), 7.02 (d, 2H), 6.88 (d, 4H), 4.38 (m, 6H), 4.03 (t, 2H), 3.72 (s, 6H), 3.20 (m, 4H), 2.97 (t, 2H), 2.51 (m, 4H), 2.26 (s, 3H), 1.75 (m, 2H), 1.58 (m, 2H), 1.39 (m, 4H), 1.20 (m, 9H).

Synthesis of Compound 24

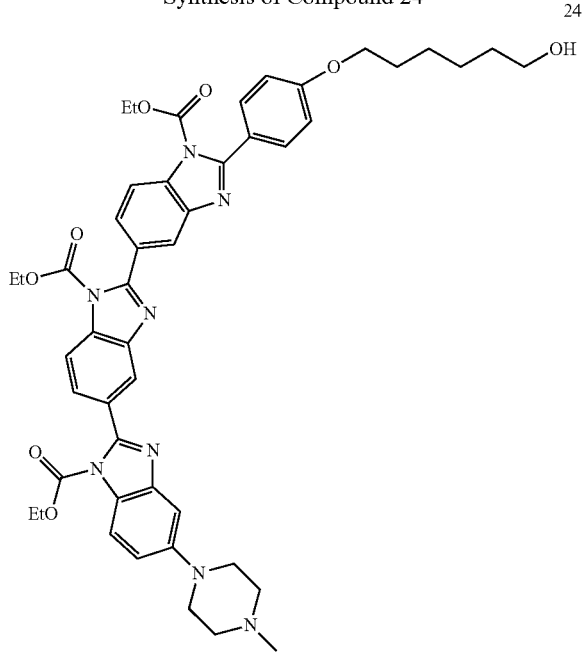 [SMILES: CCOC(=O)n1c(-c2ccc(OCCCCCCO)cc2)nc2cc(-c3nc4cc(-c5nc6cc(N7CCN(C)CC7)ccc6n5C(=O)OCC)ccc4n3C(=O)OCC)ccc21]

Trifluoroacetic acid (0.187 ml, 0.127 g, 1.70 mmol) was added to a solution of compound 10b (0.61 g, 0.53 mmol) in mixture of dichloromethane (4 ml), methanol (1 ml), and water (0.02 ml). The reaction was allowed to run for 1 hr and then quenched by addition of triethylamine (0.506 ml, 0.368 g, 3.64 mmol). Dichloromethane was removed by evaporation in vacuo and the residue chromatographed on silica eluting with 5% triethylamine, 2% methanol in dichloromethane to afford crude compound 24 as a mixture of isomers (0.408 g, light yellow solid). To remove some remaining triethylammonium salts the solid was dissolved in dichloromethane (50 ml), washed with saturated sodium bicarbonate, dried over MgSO$_4$, and concentrated in vacuo to give 0.340 g, (75%) of compound 24 as a light yellow solid. $^1$H NMR (DMSO-d6): δ 8.4-8.3 (m, 1H), 8.2-8.05 (m, 2H), 7.9-7.6 (m, 6H), 7.51 (m, 1H), 7.26-7.10 (m, 2H), 7.04 (dd, 2H), 4.36 (m, 7H), 4.07 (t, 2H), 3.42 (m, 2H), 3.20 (m, 4H), 2.50 (m, 4H), 2.42 (s, 3H), 1.76 (m, 2H), 1.42 (m, 6H), 1.21 (m, 9H).

Synthesis of Compound 25

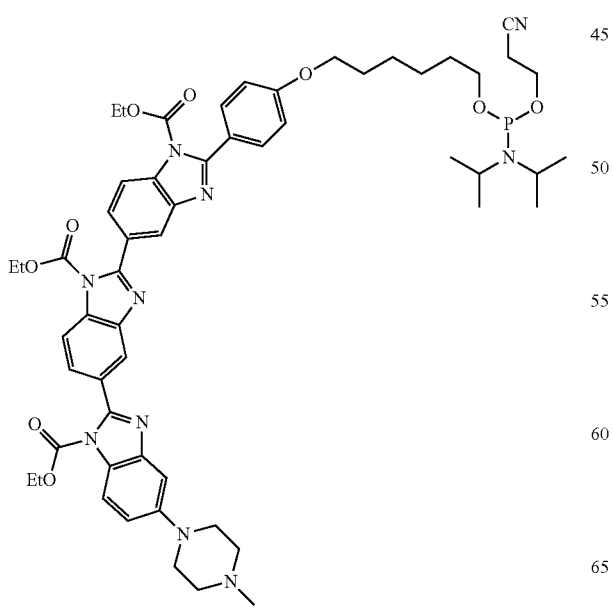

To a solution of compound 24 (0.30 g, 0.35 mmol) in dry dichloromethane (6 ml) was added diisopropylammonium tetrazolide (0.30 g, 0.35 mmol) followed by 2-cyanoethyl N,N,N',N'-tetraisopropylphosphordiamidite (0.116 g, 0.122 ml, 0.39 mmol). After being stirred for 2.5 h the reaction was treated with another portion of the phosphoramidite reagent (0.2 eq, 21 mg, 0.07 mmol), stirred for 1 h and diluted with dichloromethane and saturated aqueous NaHCO$_3$. The organic phase was separated, dried over Na$_2$SO$_4$ and concentrated in vacuo. The resultant residue was rinsed with 1:1 mixture of ether/pentane, dried twice by co-evaporation with dry acetonitrile and to afford the desired phosphoramidite 25 (0.320 g, 0.30 mmol, 85%) as a yellow-greenish semi-solid. $^{31}$P NMR (CDCl$_3$): δ 147.3.

Example 6

Oligonucleotide synthesis using MGB phosphoramidites. MGB phosphoramidite coupling efficiency and structure confirmation.

Test octathymidylates were synthesized on an ABI 3900 DNA synthesizer using thymidine-5'- or 3'-phosphoramidites and a DMT-O-hexylsuccinate solid support. Standard coupling cycle with ethylthiotetrazole as the activating agent was used for all incorporations, whereas all MGB couplings were repeated twice. All but one of the MGB phosphoramidites were used as solutions in acetonitrile. Phosphoramidite 25, which is only sparingly soluble in acetonitrile, was used as a solution in a 3:1 (by volume) mixture of acetonitrile and dichloromethane. All MGB-modified oligonucleotides were cleaved from the solid support and deprotected in a 25%/EtOH/conc. NH$_4$OH mixture at 70° C. for 2 hrs. Crude reaction mixtures were concentrated in a SpeedVac evaporator and analyzed by mass spectroscopy to confirm molecular weight and determine purity of crude MGB-oligonucleotide conjugates. It was assumed that the MGB coupling efficiency was equal or greater than the purity of crude conjugates.

| R | Sequence | MW Calculated. | MW Observed | Purity/MGB Coupling efficiency |
|---|---|---|---|---|
| 5d | 3'-hexanol-TTTTTTTT-R | 3424.6 | 3424.6 | >93% |
| 9a | 5'-hexanol-TTTTTTTT-R | 3289.5 | 3289.1 | >94% |
| 9b | 5'-hexanol-TTTTTTTT-R | 3302.5 | 3302.1 | >97% |
| 25 | 5'-hexanol-TTTTTTTT-R | 3254.4 | 3254.2 | >90% |

REFERENCES

U.S. Patent Documents

U.S. Pat. No. 4,835,263
U.S. Pat. No. 5,419,966
U.S. Pat. No. 5,512,677
U.S. Pat. No. 5,585,481
U.S. Pat. No. 5,696,251
U.S. Pat. No. 5,736,626
U.S. Pat. No. 5,801,155
U.S. Pat. No. 5,942,610
U.S. Pat. No. 5,955,590
U.S. Pat. No. 6,084,102
U.S. Pat. No. 6,312,984
U.S. Pat. No. 6,949,367
U.S. Pat. No. 7,045,610
U.S. Pat. No. 7,381,818

U.S. Pat. No. 7,582,739
U.S. Pat. No. 7,799,926
U.S. Patent Publication No. 2006/166223
U.S. Patent Publication No. 2011/0172289

International Patent Documents

International Patent Publication No. WO 2005/082894
International Patent Publication No. WO 20070/16455
Canadian Patent No. 261104

Other Publications

Afonina et al., Biotechniques, 43: 770, 772, 774 (2007)
Afonina et al PNAS, 93: 3199-3204 (1996)
Amishiro et al., J. Med. Chem., 42: 669-676 (1999)
Ausubel, et al., Current Protocols In Molecular Biology, John Wiley & Sons 1987, 1988, 1989, 1990, 1991, 1992, 1993, 1994, 1995, 1996)
Basel, Yochai and Alfred Hassner. *J. Org. Chem.,* 2000, 65 (20), pp 6368-6380
Beaucage and Iyer, Tetrahedron 48:2223-2311 (1992)
Boger et al., J. Org. Chem., 66: 6654-6661 (2001)
Boger et al. Chem. Rev., 97, 787-828 (1997)
Boger et al., JACS., 116: 7996 (994)
Boger et al., J. Org. Chem., 57:12771284 (1992)
Boger et al., *J. Org. Chem.,* 52: 1521-1530 (987)
Bostock-Smith & Searle, Nucl. Acids. Res., 27: 1619-1624 (1999)
Boyle, A. L. (Editor), Current Protocols In Nucleic Acid Chemistry, John Wiley and Sons, New York, Volume 1, 2000
Dasari et al., Org. Letters, 12: 3300-3303 (2010)
Eckstein (ed.), Oligonucleotides and Analogues: A Practical Approach, IRL Press (1991)
Gait (ed.), Oligonucleotide Synthesis: A Practical Approach, IRL Press (1984)
Greene, T. W. and P. G. Wuts, Protective Groups In Organic Chemistry, (Wiley, 2nd ed. 1991)
Harrison and Harrison et al., Compendium Of Synthetic Organic Methods, Vols. 1-8 (John Wiley and Sons. 1971-1996)
Howard et al., Bioorg. & Medicin. Chem., 10: 2941-2952 (2002)
Ichumura et al., The J. of Antibiot., 43: 1037-1038 (1990)
Jan et al., Bioorganic & Molecular Chemistry, 14: 6444-6452 (2006)
Kawashima et al., Nucl. Acids Symp. Ser (Oxf) 49: 327-328 (2005)
Levina et al., Antisense & Nucleic Acid Drug Dev., 6: 75 (1996)
MacMillan et al., JACS., 130: 16521-16523 (2008)
McGall, G. H. and Fidanza. J. A., Photolithographic synthesis of high-density olignucleotide arrays, in DNA Arrays Methods And Protocols, Edited by Rampal J. B., Methods In Molecular Biology, 170:71-101 (2001). Humana Press, Inc., NY
O'Donnell et al., Bioorg. & Med. Chem., 6: 743 (1995)
Rajur et al., 62: 523 (1997)
Reddy et al, Pharmacology & Pharmaceuticals, 84: 1-111 (1999)
Robertson, et al, Bioorg. & Med. l Chem. Letters, 20: 2722-2725 (2010)
Robles et al., J. Am. Chem. Soc., 118:5820-5821 (1996)
Sandmeyer, Ber. 17, 1633, 2650 (1884), Hodgson, Chem. Rev., 40: 2-277 (1947)
Sando et al., ChemBioChem., 8: 1795-1803 (2007)
Smith et al., J. Mol. Biol., 300: 1195-1204 (2000)
Tanada et al. J. Org. Chem., 71: 125-134 (2006)
Tichenor et al., JACS., 129(35), 10858-10869 (2007)
Tichenor et al, JACS., 129: 14092-14099 (2007)
Tichenor et al, JACS., 128: 15683-15696 (2006)
Walker, W. L., Kopka, J. L. and Goodsell, D. S., Biopolymers, 44:323-334 (1997)
Wemmer, D. E., and Dervan P. B., Current Opinon in Structural Biology, 7:355-361 (1997)
Wiederbolt et al., Bioconjug. Chem. 8: 119 (1997)
Wiederholt et al. J. Am. Chem. Soc., 118: 7055-7062 (1996)
Xu et al., *Tetrahedron Lett.,* 1995, 36(41), 7357-7360
Yamada et al., JACS., 125: 6630-6631 (2003)
Zimmer. C & Wahnert, U. Prog. Biophys. Molec. Bio. 47:31-112 (1986)

What is claimed is:
1. A minor groove binder phosphoramidite having Formula II or Formula III:

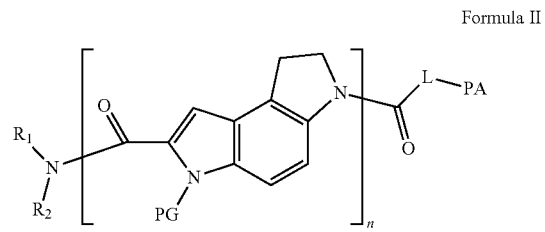

Formula II

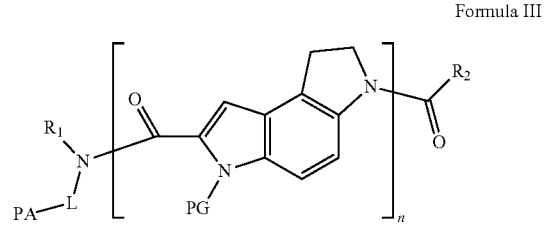

Formula III wherein $R^1$ and $R^2$ are each independently PG, L, $C_{1-8}$ alkyl, $C_{1-8}$ heteroalkyl, protected $C_{1-8}$ heteroalkyl, $-(CH_2CH_2O)_yCH_2CH_3$ where y is 1 to 8, or $R^1$ and $R^2$ form a 5 or 6 member ring structure containing 0, 1 or 2 hetero atoms selected from O, S and N;

n is 1 to 4;

L is a linker which is an acyclic, a cyclic, or an aromatic divalent moiety or a combination thereof, having from 4 to 50 atoms, exclusive of hydrogens that fill available valences, selected from a group consisting of C, N, O, P, and S;

PG is a protecting group; and

PA is a phosphoramidite group.

2. The minor groove binder phosphoramidite of claim 1 having the following formula:

3. A method for synthesizing an oligonucleotide-minor groove binder conjugate, comprising the steps of:

(a) synthesizing an oligonucleotide sequence with nucleoside phosphoramidites;

(b) incorporating the minor groove binder phosphoramidite of claim 1 into the oligonucleotide sequence to form a protected oligonucleotide-minor groove binder conjugate; and (c) deprotecting the protected oligonucleotide-minor groove binder conjugate to form an oligonucleotide-minor groove binder conjugate.

4. A minor groove binder phosphoramidite having Formula IV or V:

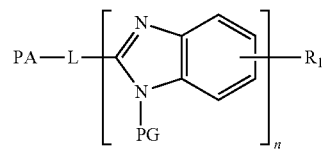

Formula IV

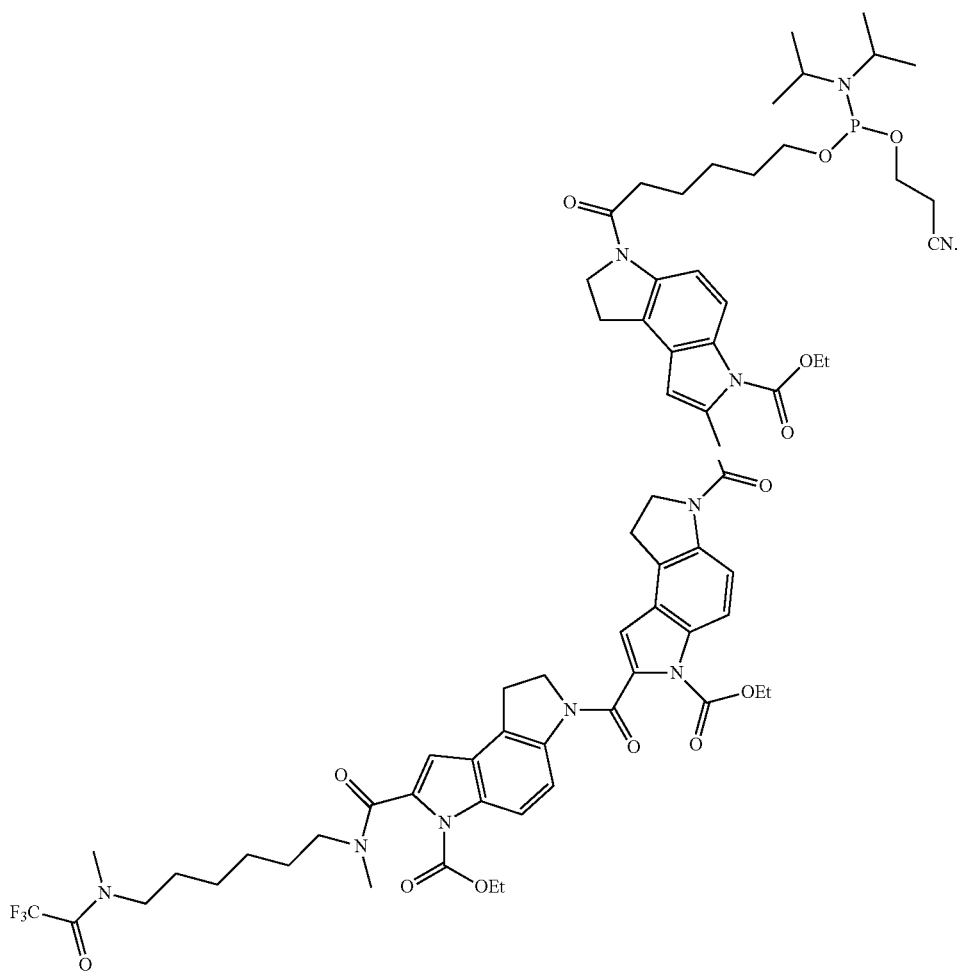 [SMILES: CCOC(=O)n1c(C(=O)N2CCc3c2ccc2c3cc(C(=O)N3CCc4c3ccc3c4cc(C(=O)N(C)CCCCCCN(C)C(=O)C(F)(F)F)n3C(=O)OCC)n2C(=O)OCC)cc2c3c(ccc21)N(C(=O)CCCCCOP(OCCC#N)N(C(C)C)C(C)C)CC3]

-continued

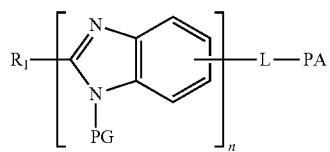

Formula V wherein R₁ is L, $C_{1-8}$ alkyl, $C_{1-8}$ heteroalkyl, protected $C_{1-8}$ heteroalkyl, —$(CH_2CH_2O)_yCH_2CH_3$ where y is 1 to 8, or substituted or unsubstituted aryl or heteroaryl;

n is 1 to 4;

L is a linker which is an acyclic, a cyclic, or an aromatic divalent moiety or a combination thereof, having from 4 to 50 atoms, exclusive of hydrogens that fill available valences, selected from a group consisting of C, N, O, P, and S;

PG is a protecting group; and

PA is a phosphoramidite group.

5. The minor groove binder phosphoramidite of claim 4 having the following formula:

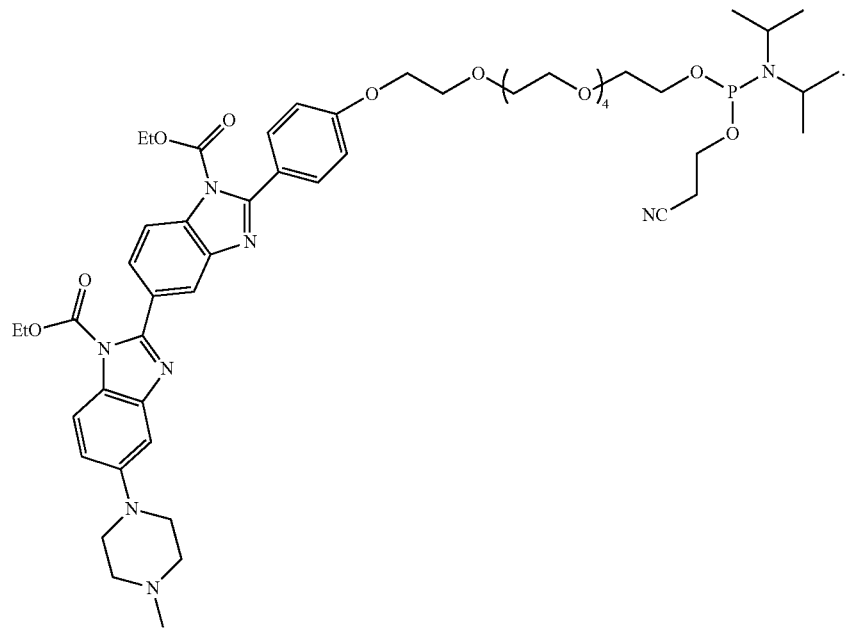

6. The minor groove binder phosphoramidite of claim 4 having the following formula:

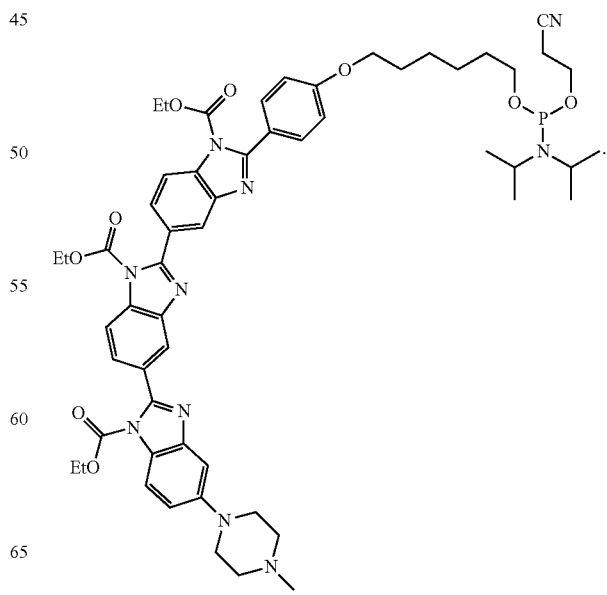

7. A method for synthesizing an oligonucleotide-minor groove binder conjugate, comprising the steps of:
- (a) synthesizing an oligonucleotide sequence with nucleoside phosphoramidites;
- (b) incorporating the minor groove binder phosphoramidite of claim 4 into the oligonucleotide sequence to form a protected oligonucleotide-minor groove binder conjugate; and
- (c) deprotecting the protected oligonucleotide-minor groove binder conjugate to produce an oligonucleotide-minor groove binder conjugate.

* * * * *